US007858095B2

(12) United States Patent
Vaishnaw

(10) Patent No.: US 7,858,095 B2
(45) Date of Patent: Dec. 28, 2010

(54) METHOD FOR TREATING OR PREVENTING SCLEROTIC DISORDERS USING CD-2 BINDING AGENTS

(75) Inventor: Akshay K. Vaishnaw, Arlington, MA (US)

(73) Assignee: Astellas US LLC, Deerfield, IL (US)

( * ) Notice: Subject to any disclaimer, the term of this patent is extended or adjusted under 35 U.S.C. 154(b) by 576 days.

(21) Appl. No.: 10/484,329

(22) PCT Filed: Jul. 10, 2002

(86) PCT No.: PCT/US02/21631

§ 371 (c)(1),
(2), (4) Date: Jun. 21, 2004

(87) PCT Pub. No.: WO03/009740

PCT Pub. Date: Feb. 6, 2003

(65) Prior Publication Data

US 2004/0265305 A1    Dec. 30, 2004

Related U.S. Application Data

(60) Provisional application No. 60/307,688, filed on Jul. 24, 2001, provisional application No. 60/382,459, filed on May 22, 2002.

(51) Int. Cl.
*A61K 38/17* (2006.01)
(52) U.S. Cl. .................... 424/185.1; 424/886
(58) Field of Classification Search ............ None
See application file for complete search history.

(56) References Cited

U.S. PATENT DOCUMENTS

| | | |
|---|---|---|
| 4,579,844 A | 4/1986 | Rovee et al. |
| 4,681,760 A | 7/1987 | Fathman |
| 4,738,297 A | 4/1988 | Taniguchi et al. |
| 4,738,927 A | 4/1988 | Taniguchi et al. |
| 4,816,397 A | 3/1989 | Boss et al. |
| 4,816,567 A | 3/1989 | Cabilly et al. |
| 4,833,092 A | 5/1989 | Geysen |
| 4,956,281 A | 9/1990 | Wallner et al. |
| 5,047,336 A | 9/1991 | Cate et al. |
| 5,116,964 A | 5/1992 | Capon et al. |
| 5,122,514 A | 6/1992 | Boger et al. |
| 5,185,441 A | 2/1993 | Wallner et al. |
| 5,190,859 A | 3/1993 | Dustin et al. |
| 5,225,538 A | 7/1993 | Capon et al. |
| 5,336,603 A | 8/1994 | Capon et al. |
| 5,547,853 A | 8/1996 | Wallner et al. |
| 5,556,943 A | 9/1996 | Yamashita et al. |
| 5,565,335 A | 10/1996 | Capon et al. |
| 5,728,677 A | 3/1998 | Wallner et al. |
| 5,730,979 A | 3/1998 | Bazin et al. |
| 5,817,311 A | 10/1998 | Bazin et al. |
| 5,914,111 A | 6/1999 | Wallner et al. |
| 5,928,643 A | 7/1999 | Wallner et al. |
| 5,951,983 A | 9/1999 | Bazin et al. |
| 5,952,499 A | 9/1999 | Whittaker et al. |
| 6,117,655 A | 9/2000 | Capon et al. |
| 6,162,432 A | 12/2000 | Wallner et al. |
| 6,270,766 B1 | 8/2001 | Feldman et al. |
| 6,337,337 B1 | 1/2002 | Buck |
| 6,384,198 B1 | 5/2002 | Diegel et al. |
| 6,764,681 B2 | 7/2004 | Wallner et al. |
| 2002/0009446 A1 | 1/2002 | Magilavy |
| 2003/0044406 A1 | 3/2003 | Dingivan |
| 2003/0068320 A1* | 4/2003 | Dingivan ............ 424/144.1 |
| 2003/0185824 A1 | 10/2003 | Vaishnaw et al. |

FOREIGN PATENT DOCUMENTS

| | | |
|---|---|---|
| CA | 2120500 | 4/1993 |
| CA | 1326940 | 2/1994 |
| CA | 1338078 | 2/1996 |
| EP | 0 200 412 A2 | 12/1986 |
| EP | 0 260 880 A2 | 3/1988 |
| EP | 0 280 578 A2 | 8/1988 |
| EP | 0 314 317 B1 | 3/1989 |
| EP | 0 325 266 A2 | 7/1989 |
| EP | 0 345 466 A2 | 12/1989 |
| EP | 0 368 684 B2 | 5/1990 |
| EP | 0 503 646 A1 | 9/1992 |
| EP | 0 503 648 A1 | 9/1992 |
| EP | 0 517 174 B1 | 12/1992 |
| EP | 0 325 262 B1 | 3/1994 |
| EP | 0 626 447 A1 | 11/1994 |
| EP | 0 607 332 B1 | 12/1997 |
| EP | 1 637 155 A1 | 3/2006 |

(Continued)

OTHER PUBLICATIONS

Selman et al., Ann Intern Med. Jan. 16, 2001;134(2):136-51.*
Troughton et al., Baillieres Clin Rheumatol. May 1994;8(2):439-63.*
Ball et al., Angew Chem Int Ed Engl. May 3, 2005;44(19):2852-2869.*
Ziwei Huang, Pharmacol Ther. Jun. 2000;86(3):201-15.*

(Continued)

*Primary Examiner*—Zachary Skelding
(74) *Attorney, Agent, or Firm*—Leydig, Voit & Mayer, Ltd.

(57) ABSTRACT

Methods and compositions for treating or preventing fibrotic disorders, e.g., sclerotic disorders, for example scleroderma, using CD2-binding agents, e.g., LFA-3/IgG fusion polypeptides or LFA-3-binding agents, are provided.

49 Claims, No Drawings

FOREIGN PATENT DOCUMENTS

| | | |
|---|---|---|
| JP | 63-233917 T2 | 9/1988 |
| JP | 2-501113 T2 | 4/1990 |
| JP | 1-502875 T2 | 10/1990 |
| JP | 2-503269 T2 | 10/1990 |
| JP | 7-502495 T2 | 3/1995 |
| WO | WO 88/06592 A1 | 9/1988 |
| WO | WO 88/07089 A1 | 9/1988 |
| WO | WO 88/09820 A1 | 12/1988 |
| WO | WO 89/02922 A1 | 4/1989 |
| WO | WO 89/07452 A1 | 8/1989 |
| WO | WO 90/02181 A1 | 3/1990 |
| WO | WO 90/07517 A1 | 7/1990 |
| WO | WO 90/08187 A1 | 7/1990 |
| WO | WO 90/09195 A1 | 8/1990 |
| WO | WO 90/12099 A1 | 10/1990 |
| WO | WO 91/07987 A1 | 6/1991 |
| WO | WO 91/10741 A1 | 7/1991 |
| WO | WO 91/11194 A1 | 8/1991 |
| WO | WO 91/11461 A1 | 8/1991 |
| WO | WO 92/07581 A1 | 5/1992 |
| WO | WO 93/06852 A2 | 4/1993 |
| WO | WO 93/06866 A2 | 4/1993 |
| WO | WO 95/24217 A1 | 9/1995 |
| WO | WO 98/05357 A1 | 2/1998 |
| WO | WO 02/060480 A1 | 8/2002 |
| WO | WO 03/009740 A3 | 2/2003 |

OTHER PUBLICATIONS

The Merriam-Webster Online, http://www.m-w.com/cgi-bin/dictionary?interstitial as accessed on Dec. 27, 2007, 1 page. Mavilia et al., Am J Pathol. Dec. 1997;151(6):1751-8.*

The Merck Manual of Diagnosis and Therapy, Mark Beers and Robert Berkow, eds., Published by Merck Research Laboratories, 17th ed., 1999, pp. 431-433.*

Mayes et al., Environ Health Perspect. Oct. 1999;107 Suppl 5:743-8.*

Mavilia et al., Am J Pathol. Dec. 1997;151(6):1751-8.*

Jefferis et al., Immunol Rev. Jun. 1998;163:59-76.*

Janeway et al., Immunobiology, 3rd Ed., Garland Science, pp. 7:4-7:7, (1997).*

Sato et al., Curr Opin Rheumatol. Nov. 1999;11(6):503-7.*

Denton et al., Clin Exp Immunol 1998; 114:293-300.*

John Varga, Curr Rheumatol Rep. Dec. 2000;2(6):481-5.*

Abraham et al. (1990) "Interactions between lymphocytes and dermal fibroblasts: An in vitro model of cutaneous lymphocyte trafficking," Experimental Cell Research 190, 118-126.

Abraham, et al., (1991) "Expression and Function of Surface Antigens on Scleroderma Fibroblasts" Arthritis and Rheumatism 34(9):1164-1172.

Actis, et al., "Continuously Infused Cyclosporine at Low Dose Is Sufficient to Avoid Emergency Colectomy in Acute Attacks of Ulcerative Colitis Without the Need for High-Dose Steroids", Journal of Clinical Gastroenterology, vol. 17,No. 1, pp. 10-13, 1993.

Adams, "How the Immune System Works and Why it Causes Autoimmune Diseases" Immunology Today, Jul. 1996;17(7):300-2.

Albert-Wolf, et al., "Immunomodulatory Properties of Soluble Recombinant Human CD58 (LFA-3) Molecules", Dev. Biol. Standard 77:87-92 (1992).

Alberts et al., Molecular Biology of the Cell, 1994, Garland Publishing, Inc., New York; NY, pp. 1243, 1994.

Alcover, et al., "Interdependence of CD3-Ti and CD2 Activation Pathways in Human T Lymphocytes", The EMBO Journal, vol. 7, No. 7, pp. 1973-1977, 1988.

Alora, et al., "Narrow-band (311 nm) UVB Phototherapy: An Audit of the First Year's experience at the Massachusetts General Hospital", Photodermatology Photoimmunology &Photomedicine,vol. 13, pp. 82-84, 1997.

Altman et al. (1990) "Transfection of genes for cell surface products involved in antigen presentation-applications to the understanding of autoimmunity" Autoimmunity 7:213-220.

Altmeyer, et al. "Traitement Systemique Du Psoriasis Par Les Derives De L'Acide Fumarique", Ann. Dermatol. Venereol, vol. 123, pp. 838-841, 1996.

Altshuler, "Implications of Psoriasis as a New Disease", Dermatology, vol. 199, pp. 1-2, 1999.

Ameen, "Genetic basis of psoriasis vulgaris and its pharmacogenetic potential", Pharmacogenomics 4(3); 297-308 (2003).

Arbuckle, et al., "Psoriasis" Pediatrics in Review, Mar. 1998;19(3):106-7.

Arellano, "Risk of Cancer with Cyclosporine in Psoriasis" International Journal of Dermatology, vol. 36, No. 1, pp. 15-17, 1997.

Arend, "The Pathophysiology and Treatment of Rheumatoid Arthritis" Arthritis & Rheumatism, vol. 40, No. 4, pp. 595-597, 1997.

Armitage, "Tests for Linear Trends in Proportions and Frequencies" Biometrics, 11, 375-386, 1955.

Arthos, et al., "Identification of the Residues in Human CD4 Critical for the Binding of HIV", Cell, 57(3):469-481 (1989).

Asadullah, et al., "IL-10 Is a Key Cytokine in Psoriasis", Journal of Clinical Investigation, vol. 101, No. 4, pp. 783-794, 1998.

Ashcroft, et al., "Clinical Measures of Disease Severity and Outcome in Psoriasis:A Critical Appraisal of their Quality" British Journal of Dermatology, vol. 141, pp. 185-191, 1999.

ATCC Cell Lines and Hybridomas 8th Edition 1994 p. 420 only.

Baadsgaard et al. (1989) "Psoriac Epidermal Cells Demonstrate Increased Nos. and Function of Non-Langerhans Antigen-presenting Cells" J. Invest. Dermatol. 92:190-195.

Bangha et al., "Evaluation of Topical Antipsoriatic Treatment by Chromametry, Visiometry and 20-MHz Ultrasound in the Psoriasis Plaque Test", Skin Pharmacology, vol. 9, pp. 298-306, 1996.

Bansil, et al. "Multiple Sclerosis: Immune Mechanism and Update on Current Therapies" Annals of Neurology, 37 (S1): 87-101, 1995.

Barbosa et al. (1986) "Gene Mapping and Somatic Cell Hybrid Analysis Of the Role Of Human Lymphocyte Function-Associated Antigen-3 (LFA-3) in CTL-Target Cell Interactions" J. Immunol. 136 (8):3085-3091.

Bardolph et al., "Psoriasis: A Review of Present and Future Manangement", Nursing Standard, vol. 12, No. 21, pp. 43-47, 1998.

Barker, "Psoriasis" Journal of the Royal College of Physicians of London, vol. 31, No. 3, pp. 238-240, 1997.

Barker, "The Pathophysiology of Psoriasis", The Lancet, vol. 338, pp. 227-230, 1991.

Barker, et al., "Leukocyte-Endothelium Interactions in Cutaneous Inflammatory Processes", Springer Seminars in Immunopathology, vol. 13, pp. 355-367, 1992.

Barker, et al., "Topical Maxacalcitol for the Treatment of Psoriasis Vulgaris: A Placebo-Controlled, Double-Blind, Dose-Finding Study with Active Comparator", British Journal of Dermatology, vol. 141, pp. 274-278, 1999.

Barsoum, "Introduction of Stable High-Copy-Number DNA into Chinese Hamster Ovary Cells by Electroporation" DNA and Cell Biology, vol. 9, No. 4, pp. 293-300, 1990.

Barthels et al., "Isolation and Nucleotide Sequence of Mouse NCAM cDNA that Codes for a M.sub.r 79000 Polypeptide Without a Membrane-Spanning Region," EMBO Journal, 6 (4), pp. 907-914 (1987).

Bay, et al., "Psoriasis Patients have T-cells with Reduced Responsiveness to Common Mycobacterial Antigens", FEMS Immunology and Medical Microbiology, vol. 21, pp. 65-70, 1998.

Bell, et al, "CD2 and the Regulation of T Cell Anergy", J Immunol. Sep. 15, 1995;155(6):2805-7.

Benjamin, et al., "MAb to cell interaction antigens block human T-dependent B cell activation", J. Cell. Biochem. Keystone Symposia on Molecular & Cellular Biology Supp. 17B:172 (1993).

Bennet, "Cyclosporine Nephrotoxicity: Implications for Dermatology", International Journal of Dermatology, vol. 36(Supp. 1), pp. 11-14, 1997.

Benton et al., "Screening the Recombinant Clones by Hybridization to Single Plaques in situ", Science, 196, 180-182 (1977).

Berth-Jones, et al., "Treatment of Psoriasis with Intermittent Short Course Cyclosporin (Neoral.RTM.). A Multicentre Study", British Journal of Dermatology, vol. 136, 'pp. 527-530, 1997.

Bieber et al. (1981) "Complications in long-term survivors of cardiac transplantation", Transplant Proc. 8(1): 207-211.

Bierer, et al. (1988) "T Cell Adhesion Molecules" FASEB J. 2:2584-2590.

Bierer et al. (1988) "Expression of the T-Cell Surface Molecule CD2 and an Epitope-Loss CD2 Mutant to Define the Role of Lymphocyte Function-Associated Antigen 3 (LFA-3) in T-Cell Activation" Proc. Natl. Acad. Sci. USA 85:1194-1198.

Bierer et al. (1989) "A Monoclonal Antibody to LFA-3, the CD2 Ligand, Specifically Immobilizes Major Histocompatibility Complex Proteins" Eur. J. Immunol. 19:661-665.

Bierer, B. et al. "Synergistic T cell activiation via the physiological ligands for CD2 and the T cell receptor", J. Exp. Med. 168: 1145-1156, Sep. 1988.

Bjerke, et al., "Acitretin Versus Etretinate in Severe Psoriasis. A double-blind Randomized Nordic Multicenter Study in 168 Patients", Acta Derm Venereol Suppl (Stockh), Vool. 146, pp. 206-207, 1989.

Bjerring, et al., "Topical Treatment of Psoriatic Skin with Methotrexate Cream: A Clinical, Pharmacokinetic, and Histological Study", Acta Derm Venereol (Stockh), vol. 66, pp. 515-519, 1986.

Bockenstedt et al. (1988) "The CD2 Ligand LFA-3 Activates T Cells But Depends on the Expression and Function of the Antigen Receptor" J. Immunol. 141:1904-1911.

Boehncke, et al., "Differential Expression of Adhesion Molecules on Infiltrating Cells Inflammatory Dermatoses", Journal of American Academy of Dermatology, vol. 26, No. 6, pp. 907-913, 1992.

Bonifati, et al., "Recognition and Treatment of Psoriasis: Special Considerations in Elderly Patients" Drugs & Aging, vol. 12, No. 3, pp. 177-190, 1998.

Bonnerjea, et al. "Protein Purification: The Right Step at the Right Time" Bio/Technology 4:955 (1986).

Borroni, et al., "Evidence for CD8+ Cell Increase in Long-Term PUVA-Treated Psoriatic Patients after PUVA Discontinuation", Dermatology, vol. 185, pp. 69-71, 1992.

Bos, et al., "Immunologie in de Medische Praktijk. VII. Psoriasis", Ned Tijdschr Geneeskd, vol. 141, No. 48, pp. 2334-2338, 1997.

Bouhnik, et al., "Long- term Follow-up of Patients with Crohn's Disease Treated with Azathioprine or 6-Mercaptopurine", The Lancet, vol. 347, pp. 215-219, 1996.

Bovenschen, et al., "Explorative immunohistochemical study to evaluate the addition of a topical corticosteroid in the early phase of alefacept treatment for psoriasis", Arch. Dermatol. Res. 298: 457-463 (2007).

Bowie et al. Deciphering the messages in protein sequences: Tolerance to amini acid substitutions. Science 240:1306-1310, Mar. 1990.

Bressler, P., et al., "Anti-CD2 Receptor Antibodies Activate the HIV Long Terminal Repeat in T Lymphocytes," J. Immunol, 147(7), pp. 2290-2294 (Oct. 1, 1991).

Brod, S. A. et al., "T-T Cell Interactions Are Mediated by Adhesion Molecules," Eur. J. Immunol., 20, pp. 2259-2268 (1990).

Bromberg et al. (1991) "Anti-CD2 Monoclonal Antibodies Alter Cell-Mediated Immunity In Vivo" Transplantation 51:219-225.

Brottier, et al., "T Cell Activation Via CD2 [T, gp50] Molecules: Accessory Cells are Required to Trigger T Cell Activation via CD2-D66 Plus CD2-9.6/T11.sub.I Epitopes.sup.I", The Journal of Immunology, vol. 135(3), pp. 1624-1631, 1985.

Brown et al. (1987) "T2.2 Characterization of CD2 Epitopes by Western Blotting" in Leukocyte Typing III, A.J. McMichael (ed.) Oxford, England: Oxford University Press, 110-112.

Brown et al. (1989) "The CD2 Antigen Associates With the T-Cell Antigen Receptor CD3 Antigen Complex on the Surface of Human T Lymphocytes" Nature 339: 551-553.

Bucherri, et al., "Acitretin Therapy is Effective for Psoriasis Associated with Human Immunodeficiency Virus Infection", Archives of Dermatology, vol. 133, pp. 711-715, 1997.

Burden, "Management of Psoriasis in Childhood", Clinical and Experimental Dermatology, vol. 24, pp. 341-345;1999.

Burns, et al., "Intralesional Cyclosporine for Psoriasis", Archives of Dermatology, vol. 128, pp. 786-790, 1992.

Camisa, Psoriasis , Blackwell Scientific Publications, 1994, 1.sup.st Ed.

Capon, et al., "Designing CD4 immunoadhesins for AIDS therapy", Nature 337(9): 525-531(1989).

Carrera, et al. "Triggering of co-mitogenic signals in T cell proliferations by anti-LFA-1 (CD18, CD11a), CLA-3, and CD7 monoclonal antibodies", J. Immunol. 141(6):1919-1924 (1988).

Cate, et al., "Isolation of the Bovine and Human Genes for Mullerian Inhibiting Substance and Expression of the Human Gene in Animal Cells", Cell, 45, 685-698 (1986).

Cerdan, et al., "Prolonged IL-2 receptor α/CD25 expression after T cell activation via the adhesion molecules CD2 and CD28", J. Immunol. 149(7):2255-2261 (1992).

Chandraratna, "Tazarotene: The First Receptor-Selective Topical Retinoid for the Treatment of Psoriasis", American Academy of Dermatology, vol. 37, No. 2, pp. S12-S17, 1997.

Chang et al. (1992) "T-Cell Activation Is Potentiated by Cytokines Released by Lesional Psoriatic, but Not Normal, Epidermis" Arch. Dermatol. 128:1479-1785.

Chavin, et al., "Prolongation of allograft and xenograft survival in mice by anti-CD2 monoclonal antibodies", Transplantation, 54(2):286-291 (1992).

Chin, Y.H. et al. "Lymphocyte Recognition of Psoriatic Endothelium: Evidence for a Tissue-Specific Receptor/Ligand Interaction",J. Invest. Dermatol. 93(2) Supplemental: 82S-87S (1989).

Chisholm et al. (1994) "The effects of an immunodulatory LFA3-IgG.sub.I fusion protein on nonhuman primates," Therapeutic Immunology 1: 205-216.

Christiansen, et al., "Etretinate (Tigason.RTM.) and Betamethasone Valerate (Celeston Valerate.RTM.) in the Treatment of Psoriasis", Dermatologica, vol. 165, pp. 204-207, 1982.

Christophers, et al., "The Inflammatory Infiltrate in Psoriasis", Clinics in Dermatology, vol. 13, pp. 131-135, 1995.

Christophers, et al., "Cyclosporine in Psoriasis: A Multicenter Dose-Finding Study in Severe Plaque Psoriasis", Therapy, Journal of the American Academy of Dermatology, vol. 26, No. 1, pp. 876-890, 1992.

Church, et al., "Genomic Sequencing", Proc. Natl. Acad. Sci. U.S.A., 81, 1991-1995 (1984).

Clayton et al. (1987) "Murine and Human T11 (CD2) cDNA Sequences Suggest A Common Signal Transduction Mechanism" Eur. J. Immunol. 17: 1367-1370.

Cohen, et al., "Immunomodulatory Agents and Other Medical Therapies in Inflammatory Bowel Disease" Current Opinion in Gastroenetrology, vol. 11, pp. 321-330, 1995.

Colten, "Pulmonary Inflammation-A Balancing Act", N Engl J Med. Apr. 10, 1997;336(15):1094-6.

Colvin, et al., "Cellular and Molecular Mechanisms of Allograft Rejection", Ann Rev Med 41:361-375 (1990).

Conti et al., (1990) "Effect of Monoclonal Antibodies on Primate Allograft Rejection" Crit. Rev. Immunol. 10(2): 113-130.

Conzelmann et al. (1986) "Anchoring of membrane proteins via phosphatidylinositol is deficient in two classes of Thy-1 negative mutant lymphoma cells", The EMBO J., vol. 5, No. 12, pp. 3291-3296.

Cooper (1990) "Immunoregulation in the Skin" Current Problems in Dermatology 19:69-80.

Cooper (1992) "Skin-infiltrating Lymphocytes in Normal and Disordered Skin: Activation Signals and Functional Roles in Psoriasis and Mycosis Fungoides-types Cutaneous T Cell Lymphoma" J. Dermatol. 19:731-737.

Cooper et al. (1985) "Effects of ultraviolet radiation on human epidermal cell alloantigen presentation: initial depression of langerhans cell-dependent function is followed by appearance of T6-Dr+ cells that enhance epidermal alloantigen presentation" J. Immunol. 134(1):129-137.

Cosimi et al.; "In Vivo Effects of Monoclonal Antibody to ICAM-1 (CD54) in Nonhuman Primates with Renal Allografts.sup.1" (The Journal of Immunology—Jun. 15, 1990 pp. 4604-4612).

Cosimi et al.; "Prolonged survival of nonhuman primate renal allograft recipients treated only with anti-CD4 monoclonal antibody" Surgery, 108 (2): 1990 pp. 406-414).
Cosimi, et al. "Immunosuppression of Cynomolgus Recipients of Renal Allografts . . . " Leukocyte Adhesion Molecules (Springer-Verlog 1988) pp. 275-281.
Cosimi, et al., "Anti-T-Cell Monoclonal Antibodies in Transplantation Therapy", Transplantation Proc. 15(3):1889-1892 (1983).
Crispe, and Mehal, "Strange Brew: T Cells in the Liver" Immunology Today, vol. 17, No. 11, pp. 522-525, 1996.
Cronstein, "The Mechanism of Action of Methotrexate", Rheumatic Disease Clinics of North America, vol. 23, No. 4, pp. 739-755, 1997.
Cuellar, et al., "Psoriatic Arthritis Current Developments" J. Florida M.A. 82(5):338-342 (1995).
Cunningham and Harris (1992) "Antibody engineering—how to be human" TIBTECH 10.
Cunningham et al., "Neural Cell Adhesion Molecule: Structure, Immunoglobulin-Like Domains, Cell Surface Modulation, and Alternative RNA Splicing," Science, 236, pp. 799-806 (1987).
Curtis, et al. (1992) "The Nature of Science" in Biology, 5.sup.th ed. (Worth Publishers, Inc.): 14-15.
Dailey, et al., "Sequences in the Polyomavirus DNA Regulatory Region Involved in Viral DNA Replication and Early Gene Expression," J. Virology, 54 (3), pp. 739-749 (Jun. 1985).
Damle, et al., "Costimulation of T lymphocytes with integrin ligands inttercellular adhesion molecule 1 or vascular cell adhesion molecule 1 induces functional expression of CTLA-4, a second receptor for B7" J. Immunol (1994).
Damle, et al., "Stimulation of cloned human T lympocytes via the CD3 or CD28 molecules induces enhancement in vascular endothelial permeability to macromolecules with participation of type -1 and type-2 intercellular adhesion pathways" Eur. J. Immunol. 20 (9):1995-2003 (1990).
Damle, N., et al., "Differential Costimulatory Effects of Adhesion Molecules B7, ICAM-1, LFA-3, and VCAM-1 on Resting and Antigen-Primed CD4.sup.+ T Lymphocytes" The Journal of Immunology, vol. 148, 1985-1992, No. 7 (Apr. 1, 1992);.
Danielian, et al., "The Tyrosine Kinase Activity of p56.sup.kk is Increased in Human T Cells Activated via CD2", European Journal of Immunology, vol. 21, pp. 1967-1970, 1991.
Davies, and Morris, "Physiological Parameters in Laboratory Animals and Humans" Pharmaceutical Research, vol. 10, No. 7, pp. 1093-1095, 1993.
Dawe, et al., "Narrow-Band (TL-01) Ultraviolet B Phototherapy for Chronic Plaque Psoriasis: Three Times of Five Times Weekly Tratment?" British Journal of Dermatology, vol. 1, No. 38, pp. 833-839, 1998.
Deckert, et al., "CD59 molecule: A second ligand for CD2 in T cell adhesion", Eur. J. Immunol. 22:2943-2947 (1992).
Denning et al. (1987) "Monoclonal Antibodies to CD2 and Lymphocyte Function Associated Antigen 3 Inhibit Human Thymic Epithelial Cell-Dependent Mature Thymocyte Activation" J. Immunol. 139(8):2573-2578.
Denning et al. (1988) "Purified Lymphocyte Function-Associated Antigen-3 (LFA-3) Activates Human Thymocytes Via the CD2 Pathway" J. Immunol. 141(9): 2980-2985.
Dente, L., et al., "pEMBL: a New Family of Single Stranded Plasmids," Nucleic Acids Research, 11(6), pp. 1645-1655 (1983).
Department of Health & Human Services, "International Conference on Harmonisation" Federal Register, vol. 62, No. 222, pp. 61515-61519, 1997.
Ding et al. (1996) "A novel murine model for the assessment of human CD2-related reagents In Vivo," J. Immunol. 157(5): 1863-1869.
Dinowitz, et al., "Recent Studies on Retrovirus-Like Particles in Chinese Hamster Ovary Cells", Developments in Biological Standardizations, vol. 76, pp. 201-207, 1991.
Drake, et al., "Guidelines of Care for Psoriasis", Journal of American Academy of Dermatology, vol. 28, No. 4, pp. 632-637, 1993.
Driscoll, et al., "Structure of Domain 1 of Rat T Lymphocyte CD2 Antigen", Nature, vol. 353, pp. 762-765, 1991.

Dustin et al. (1987) "Purified Lymphocyte Function-Associated Antigen 3 Binds to CD2 and Mediates T Lymphocyte Adhesion" J. Exp. Med. 165(3): 677-692.
Dustin et al. (1987) "T Cell Activation by LFA-3 and CD2 Antibodies" FASEB J. 45:A1239 (Abstract No. 5484).
Dustin, and Springer, "Role of Lymphocyte Adhesion Receptors in Transient Interaction and Cell Locomotion" Annual Review of Immunology, vol. 9, pp. 27-66, 1991.
Dustin, and Springer, "T-Cell Receptor Cross-Linking Transiently Stimulates Adhesiveness Through LFA-1" Nature, vol. 341, pp. 619-624, 1989.
Dustin, et al., "Anchoring Mechanisms for LFA-3 Cell Adhesion Glycoprotein at Membrane Surface", Nature, vol. 329, 846-848, 1987.
Dustin, et al., "Low Affinity Interaction of Human or Rat T Cell Adhesion Molecule CD2 with Its Ligand Aligns Adhering Membranes to Achieve High Physiological Affinity", The Journal of Biological Chemistry vol. 272, No. 49, pp. 30889-30898,1997.
Dustin, M. L., et al., "Correlation of CD2 Binding and Functional Properties of Multimeric and Monomeric Lymphocyte Function-Associated Antigen 3," J. Exp. Med., 169, pp. 503-517 (Feb. 1989).
Duvic, et al., "Molecular Mechanisms of Tazarotene Action in Psoriasis", Journal of American Academy of Dermatology, vol. 37, No. 2, pp. S18-S24, 1997.
Economidou, et al., "Effects of Cyclosporin A on Immune Activation Markers in Patients with Active Psoriasis", Dermatology, vol. 199, pp. 144-148, 1999.
Edelhoch, "Spectroscopic Determination of Tryptophan and Tyrosine in Proteins" Biochemistry, vol. 6, No. 7, pp. 1948-1954, 1967.
Ehmann, and Voorhees, "Effect of Oral Synthetic Retinoids on Keratinizing Disorders", Journal of American Academy of Dermatology, vol. 6, No. 4, pp. 692-696, 1982.
Ekborn, et al., "Crohn's Disease After In-Utero Measles Virus Exposure", The Lancet, vol. 348, pp. 515-517, 1996.
Elder, et al., "Efficacy and Pharmacokinetics of Two Formulations of Cyclosporine A in Patients with Psoriasis" Journal of Clinical Pharmacology, vol. 35, pp. 865-875, 1995.
Ellis, "Quality of Life Results from a Randomized Double Blind Multi Center Dose Response study of LFA3TIP in patients with Chronic Plaque Psoriasis" Am Acad Dermatol. 58th Ann Meeting Mar. 10-15, 2000. (Abstract).
Ellis, et al., "Cyclosporine for Plaque-Type Psorisis: Results of a Multidose, Double-Blind Trial", The New England Journal of Medicine vol. 324, No. 5, pp. 276-284, 1991.
Ellis, et al., "Treatment of chronic plaque psoriasis by selective targeting of memory effector T lymphocytes", The New England J. Med. 345(4):248-255 (2001).
Enea, V. and N. D. Zinder, "Interference Resistant Mutants of Phage f1," Virology, 122, pp. 222-226 (1982).
Ewe,et al., "Azathioprine and Prednisolone for Active Crohn Disease", ACP Journal Club, 1994, Annals of Internal Medicine 120/2 Suppl. 1 (13).
Ezekowitz, et al., "The Interferons: Basic Biology and Therapeutic Potential" in Therapeutic Immunology, edited by Austen et al., (Blackwell Science, Cambridge, MA, 1996) 249-263.
Farber, "Juvenile Psoriasis: Early Interventions Can Reduce Risks for Problems Later" Postgraduate Medicine vol. 103, No. 4, pp. 89-100, 1998.
Farber, et al. "Psoriasis: A Disease of the Total Skin" Journal of American Academy of Dermatology, vol. 12(1), pp. 150-156, 1985.
Faulds, et al., "Cyclosporin: A Review of its Pharmacodynamic and Pharmacokinetic Properties, and Therapeutic Use in Immunoregulatory Disorders", Drugs, vol. 45, No. 6, pp. 953-1040, 1993.
Feagan, et al., "Methotrexate for the Treatment of Crohn's Disease" The New England Journal of Medicine, vol. 332(5), pp. 292-297, 1995.
Feagan, et al., "Methotrexate Improved Symptoms in Chronic Active Crohn Disease", ACP Journal Club, Jul.-Aug. 1995;123(1) 9.
Feagan, et al., "Therapeutics and Inflammatory Bowel Disease: A Guide to the Interpretation of Randomized Controlled Trials" Gastroenterology, vol. 110, pp. 275-283, 1996.

Feldman, et al., "The Economic Impact of Psoriasis Increases with Psoriasis Severity" Journal of American Academy of Dermatology, vol. 37(4), pp. 564-569, 1997.

Feldman, et al., "The Self-Administered Psoriasis Area and Severity Index Is Valid and Reliable", Journal of Investigative Dermatology, vol. 106, pp. 183-186, 1996.

Ferguson et al. (1988) "Cell-surface anchoring of proteins via glycosyl-phosphatidylinositol structures", Ann. Rev. Biochem., vol. 57, pp. 285-320.

Ferracciolli, et al., "Effects of cyclosporine on joint damage in rheumatoid arthritis", Clin Exp. Rheum. 15 (Supp 17):S83-S89 (1997).

Ffrench-Constant, "Pathogenesis of Multiple Sclerosis", The Lancet, vol. 343, pp. 272-278, 1994.

Findlay "Purification of Membrane Proteins" Ch. 4 in Protein Purification Applications, A Practical Approach (Harris and Angel, eds) 1990 (cited for argument).

Findlay, and Khan, "Dermatology Life Quality Index (DLQI): A Simple Practical Measure for Routine Clinical Use", Clinical and Experimental Dermatology, vol. 19, pp. 210-216, 1993.

Finzi, et al., "A Clinical Survey of Psoriasis in Italy: 1.sub.st AISP Report" Journal of the European Academy of Dermatology and Venereology, vol. 10,pp. 125-129, 1998.

Finzi, et al., "Cyclosporin versus Etretinate: Italian Multicenter Comparative Trial in Severe Plaque-Form Psoriasis", Dermatology, vol. 187(suppl 1), pp. 8-18, 1993.

First, "Transplantation in the Nineties", Transplantation 53(1):1-11 (1992).

Fischel, et al. "The cellular response to xenotransplantation", Curr. Surg. 47(5):345-347 (1990).

Fischer, "T cell adhesion", J. Exp. Clin. Hematol. 32:49-51 (1990).

Fleischer, Jr., et al., "Disease Severity Measures in a Population of Psoriasis Patients: The Symptoms of Psoriasis Correlate with Self-Administered Psorisis Area Severity Index Scores", Journal of Investigative Dermatology, vol. 107, No. 1, pp. 26-29, 1996.

Fleischer, Jr., et al., "Patient Measurement of Psoriasis Disease Severity with a Structured Instrument" Journal of Investigative Dermatology, vol. 102, No. 6, pp. 967-969, 1994.

Fortune, et al., "Quality of Life in Patient with Psoriasis: the Contribution of Clinical Variables and Psoriasis-Specific Stress", British Journal of Dermatology, vol. 137, pp. 755-760, 1997.

Fox, "The Role of T Cells in the Immunopathogenesis of Rheumatoid Arthritis", Arthritis & Rheumatism, vol. 40, No. 4, pp. 598-609, 1997.

Gamache et al. (1996) "Pharmacokinetics of LFA3TIP, an immunoglobulin fusion protein, in male and female baboons," Pharmaceutical Research 13 (9 Sup.): s399 (Abstract).

Geider, K., et al., "A Plasmid Cloning System Utilizing Replication and Packaging Functions of the Filamentous Bacteriophage fd," Gene, 33, pp. 340-349 (1985).

Genmab Press release 48/2002 "HuMAX CD-4 in combination therapy not effective in Rheumatoid Arthritis".

Georgouras, et al. "Systemic Treatment of Severe Psoriasis", Australasian Journal of Dermatology, vol. 38, pp. 171-182, 1997.

Gimenez-Arnau, et al., "Psoriasis: bases de actuacion terapeutica", Act. Dermatolog.3:159-171(1998).

Giorgi, et al, "Immunosuppressive Effect and Immunogenicity of OKT11A monoclonal antibody in monkey allograft recipients", Transplantation Proc. 15(1):639-642 (1983).

Gismondi, et al., "Triggering through CD16 or Phorbol Esters Enhances Adhesion of NK Cells to Laminin via Very Late Antigen 6", Journal of Experimental Medicine, vol. 176,pp. 1251-1257,1992.

Goebell, et al., "Drug Trials in Inflammatory Bowel Diseases 1993-1995: A Survey Conducted by the IOIBD", Inflammatory Bowel Diseases, vol. 2, pp. 265-267, 1996.

Goedkoop et al., "Alefacept therapy reduces the effector T-cell population in lesional psoriatic epidermis", Arch. Dermatol. Res. 295:465-473 (2004).

Goldman, et al., "OKT3-Induced Cytokine Release Attenuation by High-Dose MethilPrednisolone", Lancet. Sep. 30, 1989;2(8666):802-3.

Gollnick, et al., "Acitretin* versus Etretinate in Psoriasis: Clinical and Pharmacokinetic Results of a German Multicenter Study", Journal of American Academy of Dermatology, vol. 19, No. 3, pp. 458-468, 1988.

Gollob, et al., "CD2 Regulates Responsivenes of Activated T Cells to Interleukin 12", Journal of Experimental Medicine, vol. 182, pp. 721-731, 1995.

Gonzales-Ramos et al. (1992) "APC-Targeted Immunointervention in Psoriasis: Blockade of LFA-3-CD2 and ICAM 1-LFAI Ligand Pairing Blocks Autoreactivity to Lesional Epidermis" Clinical Research 40(2):500A. •.

Gordon, et al., "Treatment of psoriasis with alefacept", Arch. Dermatol. 139: 1563-1570 (2003).

Gottlieb, "The Challenges of Treating Moderate to Severe Psoriasis", International Journal of Dermatology, vol. 36(suppl 1), pp. 41-44, 1997.

Greaves, and Weinstein, "Treatment of Psorisis", The New England Journal of Medicine, vol. 332, No. 9, pp. 581-588, 1995.

Greenberg, et al., "Oral Budesonide for Active Chrohn's Disease", The New England Journal of Medicine, vol. 331, No. 13, pp. 836-845, 1994.

Gregersen, et al., "A CD4: immunoglobulin fusion protein with antiviral effects against HIV", Arch. Virol. 111:29-43 (1990).

Grossman, et al., "A Novel Therapeutic Approach to Psoriasis with Combination Calcipotriol Ointment and Very-Low-Dose Cyclosporine: Results of a Multicenter Placebo-Controlled Study", Journal of American Academy of Dermatology, vol. 31, No. 1, pp. 68-74, 1994.

Grossman et al., "Long-term Safety of Cyclosporine in the Treatment of Psoriasis", Archives of Dermatology, vol. 132, pp. 623-629, 1996.

Grosveld, et al., "The Construction of Cosmid Libraries Which Can Be Used to Transform Eukaryotic Cells", Nucl. Acids. Res., 10(21), 6715-6732 (1982).

Gubler, et al., "A Simple and Very Efficient Method for Generating cDNA Libraries", Gene, 25, 263-269 (1983).

Guckian, et all., "Immunomodulation at the Initiation of Phototherapy and photochemotherapy", Photodermatology, Photoimmunology & Photomedicine, vol. 11, pp. 163-169, 1995.

Gulliver, et al., Increased Bioavailability and Improved Efficacy, in Severe Psoriasis, of a New Microemulsion Formulation of Cyclosporin*, British Journal Of Dermatology, vol. 135(suppl 48), pp. 35-39, 1996.

Guzzo, "Recent Advances in the Treatment of Psoriasis", Dermatologic Clinics, vol. 15, No. 1, pp. 59-68, 1997.

Hafler, et al., "Anti-CD4 and anti-CD2 monoclonal antibody infusions in subjects with multiple sclerosis", J. Immunol. 141(1):131-138 (1988).

Hale, et al. "Bromelain treatment of human T cells removes CD44, CD45RA, E2/MIC2, CD6, CD7, CD8, and Leu 8/LAM1 surface molecules and markedly enhances CD2- mediated T cell activation", J. Immunol. 149(12):3809-3816 (1992).

Hamblin, "From Dendritic Cells to Tumour Vaccines", The Lancet, vol. 347, pp. 705-706, 1996.

Hanauer, "Inflammatory Bowel Disease", Drug Therapy, vol. 334, No. 13, pp. 841-848,1996.

Hanauer, "Medical Therapy of Ulcerative Colitis" The Lancet, vol. 342, pp. 412-417, 1993.

Hardman, et al., "Active Psoriasis and Profound CD4.sup.+ Lymphocytopenia", British Journal Of Dermatology, vol. 136, pp. 930-932, 1997.

Harris and Emery (1993) "Therapeutic antibodies—the coming of age" TIBTECH 11: 42-44.

Hawke, et al., "Autoimune T Cells in *Myasthenia gravis*: Heterogeneity and Potential for Specific lmmunotargeting", Immunology Today, vol. 17, No. 7, pp. 307-311, 1996.

Hawkes, et al., "A Dot-Immunobinding Assay for Monoclonal and Other Antibodies", Anal. Biochem., 119, 142-147 (1982).

Haynes, B.F. et al. "Synovial microenvironment-T cell interactions", Arthritis and Rheum. 31 (8): 947-955 (1988).

He et al., "Phosphatidylinositol is Involved in the Membrane Attachment of NCAM-120, the Smallest Component of the Neural Cell Adhesion Molecule," EMBO Journal, 5, (10), pp. 2489-2494 (1986).

Hebel, et al., "Suppression of the immune response by a soluble complement receptor of B lymphocytes", Science 254(5028):102-105 (1991) (cited for argument).

Heij (La Heij), et al., "Adhesion molecules in iris biopsy specimens from patients with uveitis", Br. J. Opthamol. 82(4):432-437 (1998).

Henseler, "The Genetics of Psoriasis", Journal of American Academy of Dermatology, vol. 37, No. 2, pp. S1-S11, 1997.

Henseler, and Christophers, "Disease Concomitance in Psoriasis", Journal of American Academy of Dermatology, vol. 32, pp. 982-986, 1997.

Henseler, and Christophers, "Psoriasis of Early and Late Onset: Characterization of Two Types of Psoriasis Vulgaris", Journal of American Academy of Dermatology, vol. 13, No. 3, pp. 450-456, 1995.

Herbin, et al., "Automated Registration of Dissimilar Images: Application to Medical Imagery", Computer Vision, Graphics, and Image Processing, vol. 47, pp. 77-88, 1989.

Hewick, et al., "A Gas-Liquid Solid Phase Peptide and Protein Sequentor", J. Biol. Chem., 256(15), 7990-7997 (1981).

Hiramine, et al., "Differential Effect of Cyclosporine in Vivo on the Distribution of T cell Subsets in the Thymus, Spleen, and Lymph Nodes", Transplatation, vol. 47, No. 3, pp. 499-503, 1989.

Hirano, et al., "Individual Pharmacodynamics Assessed by Antilymphocyte Action Predicts Clinical Cyclosporine Efficacy in Psoriasis", Clinical Pharmacology & Therateutics, vol. 63, No. 4, pp. 465-470, 1998.

Ho, et al., "Intermittent Short Courses of Cyclosporin (Neoral.RTM.) for Psoriasis Unresponsive to Topical Therapy: A 1-Year Multicentre, Randomized Study", British Journal of Dermatology, vol. 141, pp. 283-291, 1999.

Hoffmann, et al., "Initiation and perpetuation of rat adjuvant arthritis is inhibited by the anti-CD2 monoclonal antibody (mAb) OX34", Annals of Rheumatic Diseases, 56 (12) : 716-722 (1997).

Hollsberg, et al., "Increased protein kinase C activity in human memory T cells", Cell. Immunol. 149(1):170-179 (1993).

Honeyman, et al., "Low-Dose Cyclosporine a Improves Severe Disabling Psoriasis in Latin America", International Journal of Dermatology, vol. 34, pp. 583-588, 1995.

Hooks et al., "Muromonab CD-3: A review of its pharmacology, pharmacokinetics, and clinical use in transplantation", Pharmacotherapy 11(1):25-37 (1991).

Hopkins, et al., "A double-Blind Controlled Trial of Etretinate (Tigason) and Ibuprofen in Psoriatic Arthritis", Annals of the Rheumatic Diseases, vol. 44, pp. 189-193, 1985.

Howard et al. (1981) A human T lymphocyte differentiation marker defined by monoclonal antibodies that block E-rosette formation: J. Immunol. 126(6):2117-2122.

Hughes et al. (1990) "Endothelial Cells Augment T Cell Interleukin 2 production by a Contact-Dependent Mechanism involving CD2/LFA-3 Interaction" J. Exp. Med. 171:1453-1467.

Hughes et al. (1990) "The Endothelial Cell as a Regulator of T-Cell Function" Immunol. Rev. 117, 85-102.

Hugot, et al., "Mapping of a Susceptibility Locus for Crohn's Disease on Chromosome 16", Nature, vol. 379, pp. 821-823, 1996.

Hunt, et al., "Generalized Pustular Psoriasis Responsive to PUVA and Oral Cyclosporin Therapy", Australasian Journal of Dermatology, vol. 38, pp. 199-201, 1997.

Hyman (1985) "Cell-surface-antigen mutants of haematopoietic cells",Biochem J., vol. 225, pp. 27-40.

Ieiri et al., "Evaluation of the Therapeutic Range of Whole Blood Cyclosporin Concentration in the Treatment of Psoriasis", International Journal of Clinical Pharmacology and Therateutics, vol. 34, No. 3, pp. 106-111, 1996.

Ikemizu, et al., "Crystal Structure of the CD2-Binding Domain of CD58 (Lymphocite Function-Associated Antigen 3) at 1.8-.ANG. Resolution", Proceedings of the National Academy of Science, vol. 96, pp. 4289-4294, 1999.

Inoue, et al., "Anti-adhesion molecule therapy in Theiler's murine encephalomyelitis virus-induced demyelinating disease", Int. Immunol. 9(12):1837-1847 (1997).

International Searching Authority, International Search Report for International Application No. PCT/US88/01924, dated Oct. 7, 1988.

International Searching Authority, International Search Report for International Application No. PCT/US89/03652, dated Feb. 7, 1990.

International Searching Authority, International Search Report for International Application No. PCT/US92/02050, dated Aug. 12, 1992.

International Searching Authority, International Search Report for International Application No. PCT/US92/08754, dated Jun. 28, 1993.

International Searching Authority, International Search Report for International Application No. PCT/US92/08755, dated Jul. 8, 1993.

International Searching Authority, International Search Report for International Application No. PCT/US99/20026, dated May 8, 2000.

International Searching Authority, International Search Report for International Application No. PCT/US02/02314, dated Jun. 11, 2002.

International Searching Authority, International Search Report for International Application No. PCT/US02/21631, dated Jun. 25, 2003.

International Searching Authority, International Search Report for International Application No. PCT/US05/16265, dated Oct. 26, 2005.

International Searching Authority, International Search Report for International Application No. PCT/US05/15531, dated Feb. 24, 2006.

International Searching Authority, International Search Report for International Application No. PCT/US05/03907, dated Oct. 3, 2005.

International Searching Authority, International Search Report for International Application No. PCT/US05/39070, dated Apr. 27, 2007.

Ip, et al., Structural Characterization of the N-Glycans of a Humanized Anti-CD18 Murine Immunoglobulin G, Archives of Biochemistry and.Biophysics, vol. 308, No. 2, pp. 387-399, 1994.

Isaacs, et al., "Humanized Anti-CD4 Monoclonal Antibody Therapy of Autoimmune and Inflammatory Disease", Clinical and Experimental Immunology, vol. 110, pp. 158-166, 1997.

Jefferis, and Lund, "Glycosylation of Antibody Molecules: Structural and Functional Significance", Chemical Immunology, vol. 65, pp. 111-113, 1997.

Jemec, and Wulf, "The Applicability of Clinical Scoring Systems: SCORAD and PASI in Psoriasis and Atopic Dermatitis", Acta Derm Venereol (Stockholm), vol. 77, pp. 392-393, 1997.

Jenkins, et al., "CD28 Delivers a Constimulatory Signal Involved in Antigen-Specific IL-2 Production by Human T Cells", The Journal of Immunology, vol. 147(8), pp. 2461-2466, 1991.

Johnson, "On Teaching Dermatology to Nondermatologists", Arch Dermatol, vol. 130, pp. 850-852, 1994.

Jones, et al., "Crystal Structure at 2.8.ANG. Resolution of a Soluble Form of the Cell Adhesion Molecule CD2" Nature, vol. 360, pp. 232-239, 1992.

Jonker, "Immunosuppressive Therapy by monoclonal anti-T lymphocyte subset antibodies", Leukocyte Typing III (Oxford Univ. Press 1987) pp. 923-927.

Jonker, et al., "The Influence of OKT8F Treatment on Allograft Survival in Rhesus Monkeys", Transplantation 41(4): 431-435 (1986).

Jonker, et al., "Effects of in vivo administration of monoclonal antibodies specific for human T cell subpopulations on the immune system in a rhesus monkey model", Transplantation 35(6): 521-526 (1983).

June, "Increases in Tyrosine Phosphorylation are Detectable Before Phospholipase C Activation After T Cell Receptor Stimulation", The Journal of Immunology, vol. 144, No. 5, pp. 1591-1599, 1990.

Kang, et al., "Calcipotriene-Induced Improvement in Psoriasis is Associated with Reduced Interleukin-8 and Increased Interleukin-10 levels within Lesions", British Journal of Dermatology, vol. 138, pp. 77-83, 1998.

Kanner, et al., "CD2/LFA-3 Ligation Induces Phospholipase-C. gamma.1 Tyrosine Phosphorylation and Regulates CD3 Signaling", The Journal of Immunology, vol. 148, No. 7, pp. 2023-2029, 1992.

Kantor, et al., "Double-Blind Bilateral Paired Comparison of 0.05% Halobetasol Propionate Cream and its Vehicle in Patients with Chronic Atopic Dermatitis and Other Eczematous Dermatoses", Journal of the American Academy of Dermatology, vol. 25, No. 6, pp. 1184-1186. 1991.

Kaplan et al. (1987) "Distribution and Turnover of Langerhans Cells During Delayed Immune Responses in Human Skin" J. Exp. Med. 165:763-776.

Kaplon et al. (1996) "Short course single agent therapy with an LFA-3-IgG.sub.I fusion protein prolongs primate cardiac allograft survival." Tranplantation 61(3): 356-363.

Kasahara, et al., "Role of interleukin 6 for differential responsiveness of naive and memory CD4+ T cells in CD2-mediated activation", J. Exp. Med. 172 (5):1419-1424 (1990).

Kato, et al., "CD48 is a Counter-Receptor for Mouse CD2 and is Involved in T Cell Activation", Journal of Experimental Medicine, vol. 176, pp. 1241-1249, 1992.

Kaufman, and Sharp, "Amplification and Expression of Sequences of Cotransfected with a Modular Dihydrofolate Reductase Complementary DNA Gene", Journal of Molecular Biology, vol. 159, pp. 601-621, 1982.

Kaufman, and Sharp, "Construction of a Modular Dihydrofolate Reductase cDNA Gene: Analysis of Signals Utilized for Efficient Expression", Molecular and Cellular Biology, vol. 2, No. 11, pp. 1304-1319, 1982.

Kawai, et al., "Intrathecal administration of antibodies against LFA-1 and against ICAM-1 suppresses experimental allergic encephalomyelitis in rats", Cell Immunol. 171(2):262-268 (1996).

Kelso, Th1 and Th2 Subsets: Paradigms Lost?, Immunology Today, vol. 16, No. 8, pp. 374-379, 1995.

Kent, S. B. H., "Chemical Synthesis of Peptides and Proteins," Ann. Rev. Biochem., 57, pp. 957-989 (1988).

Killeen et al., "The MRC OX-45 Antigen of Rat Leukocytes and Endothelium is in a Subset of the Immunoglobulin Superfamily with CD2, LFA-3 and Carcinoembryonic Antigens", The EMBO Journal, vol. 7, No. 10, pp. 3087-3091, 1988.

Kimball ,Introduction to Immunology, 1983, (Ed.), Macmillan Publishing Co., New York, NY, 1983.

Kingston, et al., "Etretin Therapy for Severe Psoriasis", Arch Dermatol, vol. 123, pp. 55-58, 1987.

Kirkham, et al., "Chimeric CD7 monoclonal antibody therapy in Rheumatoid arthritis", J. Rheumatol. 19(9) 1348-1352 (1992).

Knox, et al., "Observations on the effect of chimeric anti-CD4 monoclonal antibody in patients with mycosis fungoides", Blood 77(1):20-30 (1991).

Kohler, G. and C. Milstein, "Continuous Cultures of Fused Cells Secreting Antibody of Predefined Specificity," Nature, 256, pp. 495-497 (Aug. 7, 1975).

Kollias, "Letter to the Editor: Simple Changes to PUVA Phototherapy May Minimize to the Photocarcinogenic Risks", Photodermatology, Photoimmunology, & Photomedicine, vol. 15, pp. 205, 1999.

Koo, "Neoral in Psoriasis Therapy: Toward a New Perspective", International Journal of Dermatology, vol. 36, pp. 25-29, 1997.

Koo, "Population-Based Epidemiological Study of Psoriasis with Emphasis on Quality of Life Assessment", Psychodermatology, vol. 14, No. 3, pp. 485-496, 1996.

Koo, "Systematic Sequential Therapy of Psoriasis: A New Paradigm for Improved Therapeutic Results", Journal of the American Academy of Dermatology, vol. 41, No. 3, pp. S25-S28, 1999.

Koo, et al., "Mometasone Furoate 0.1%-Salicylic Acid 5% Ointment Versus Mometasone Furoate 0.1% Ointment in the Treatment of Moderate-to-Severe Psoriasis: A Multicenter Study", Clinical Therapeutics, vol. 20, No. 2, pp. 283-291, 1998.

Koshy, et al., "Increased Expression of CD40 Ligand on Systemic Lupus Erythematosus Lymphocytes", Journal of Clinical Investigation, vol. 98, No. 3, pp. 826-837, 1996.

Koyasu et al. (1990), "Role of Interaction of CD2 Molecules With Lymphocyte Function-Associated Antigen 3 in T-Cell Recognition of Nominal Antigen" Proc. Natl. Acad. Sci. USA 87: 2603-2607.

Kraan et al., "Alefacept Treatment in Psoriatic Arthritis" Arthritis Rheum. 46(10):2776-2784 (2002).

Kragballe, et al., "A Double-Blind Comparison of Acitretin and Etretinate in the Treatment of Severe Psoriasis", Acta Derm Venereol (Stockh), vol. 69, pp. 35-40, 1989.

Kranz et al., "Immunoprecipitation of Cell Surface Structures of Cloned Cytotoxic T Lymphocytes by Clone-Specific Antisera," Proc. Natl. Acad. Sci. U.S.A., vol. 81, pp. 573-77 (1984).

Krensky (1990) "The Human Cytolytic T Lymphocyte Response to Transplantation Antigens" Pediatric Res. 19(12):1231-1234.

Krensky et al. (1983) "The Functional Significance, Distribution, and Structure of LFA-1, LFA-2, and LFA-3: Cell Surface Antigens Associated With CTL-Target Interactions" J. Immunol. 131(2):611-616.

Krensky et al. (1984) "Human Lymphocyte Function Associated Antigens" Surv. Immunol. Res. 3:39-44.

Krueger, et al., "Anti-CD11a treatment for psoriasis concurrently increases circulating T-cells and decreases plaque T-cells, consistent with inhibition of cutaneous T-cell trafficking", J. Inves. Derm. 115:333 (2000) (Abstract).

Krueger "Efficacy and Safety results of a phase II trial with LFA3TIP in patients with chronic plaque psoriasis." Am Acad Dermatol. 58th Ann Meeting Mar. 10-15, 2000. (Abstract).

Krueger, and Duvic, "Epidemiology of Psoriasis: Clinical Issues", The Journal of Investigative Dermatology, vol. 102, No. 6, pp. 14S-18S, 1994.

Krueger, Efficacy and Safety results of a phase II trial with LFA3TIP in patients with chronic plaque psoriasis. From Gene to Clinic Congress. AMEVIVE™ Breakfast Meeting Dec. 3, 1999 p. 1.

Krueger, et al., "The Safety and Efficacy of Tazarotene Gel, a Topical Acetylenic Retinoid, in the Treatment of Psoriasis", Arch Dermatol, vol. 134, pp. 57-60, 1998.

Kullavanijaya, and Kulthanan, "Clinical Efficacy and Side Effects of Acitrctin on the Disorders of Keratinization: A One-Year Study", The Journal of Dermatology, vol. 20, pp. 501-506, 1993.

Kumar, et al., "Methotrexate in Childhood Psoriasis", Pediatric Dermatology, vol. 11, No. 3, 271-273, 1994.

Kumar, et al., "Short Term Methotrexate Therapy in Psoriasis", Indian J Med Res, vol. 100, pp. 277-280, 1994.

Kupper, "Immune and inflammatory processes in cutaneous tissues: mechanisms and speculations", J.Clin. Invest. 86:1783-1789 (1990).

Laburte, et al., "Efficacy and Safety of Oral Cyclosporin A (CyA; Sandimmun.RTM.) for Long-Term Treatment of Chronic Severe Plaque Psoriasis", British Journal of Dermatology, vol. 130, pp. 366-375, 1994.

Lai et al., "Two Forms of TB236/Myelin-Associated Glyco Protein, a Cell Adhesion Molecule for Postnatal Neural Development, are Produced by Alternative Splicing," Proc. Natl. Acad. Sci. U.S.A., 84, pp. 4337-4441 (1987).

Lai et al., "Solid-State Chemical Stability of Proteins and Peptides", Journal of Pharmaceutical Sciences, vol. 88, No. 5, pp. 489-500, 1999.

Lambert, et al., "Safety and Pharmacokinetics of Hyperimmune Anti-Human Immunodeficiency Virus (HIV) Immunoglobulin Administered to HIV-Infected Pregnant Women and Their Newborns", The Journal of Infectious Diseases, vol. 175, pp. 283-291, 1997.

Lambert, J. M. et al., "Purified Immunotoxins That Are Reactive With Human Lymphoid Cells," J. Biol. Chem., 260(22), pp. 12035-12041 (1985).

Langford, et al., "Use of Cytotoxic Agents and Cyclosporine in the Treatment of Autoimmune Disease", Annals of Internal Medicine, vol. 129, No. 1, pp. 49-58, 1998.

Lanigan, "Treatment of Psoriasis with the Pulsed Dye Laser", Journal of the American Academy of Dermatology, vol. 37, No. 2, pp. 288-289, 1997.

Larson and Springer (1990) "Structure and function of leukocyte integrins" Immunol. Revs. 114:181-217.

Lauharanta, and Geiger, "A Double-Blind Comparison of Acitretin and Eretinate in Combination with Bath PUVA in the Treatment of Extensive Psoriasis", British Journal of Dermatology, vol. 121, 107-112, 1989.

Lauharanta, et al., "A Clinical Evaluation of the Effects of an Aromatic Retinoid (Tigason), Combination of Retinoid and PUVA, and PUVA Alone in Severe Psoriasis", British Journal of Dermatology, vol. 104, pp. 325-332, 1981.

Le et al. (1987) "Anti-LFA-3 Monoclonal Antibody Induced Interteukin 1 (IL 3) Release by Thymic Epithelial (TE) Cells and Monocytes" FASEB J. 46(3):447 Abstract 761.

Le et al. (1990) "Ligan Binding to the LFA-3 Cell Adhesion Molecule Induces Il-1 Production by Human Thymic Epithelial Cells" J. Immunol. 144:4541-4547.

Lebwohl, et al., "Interactions Between Calcipotriene and Ultraviolet Light", Journal of the American Academy of Dermatology, vol. 37, No. 1, pp. 93-95, 1997.

Lebwohl, et al., "Once-Daily Tazarotene Gel Versus Twice-Daily Flucinonide Cream in the Treatment of Plaque Psoriasis", Journal of the American Academy of Dermatology, vol. 38, No. 5, pp. 705-711, 1998.

Ledo, et al., "Acitretin (Ro 10-1670) in the Treatment of Severe Psoriasis: A Randomized Double-Blind Parallel Study Comparing Acitrecin and Eretinate", International Journal of Psoriasis, vol. 27, No. 9, pp. 656-659, 1988.

Lemster, et al., "FK 506 Inhibits Cytokine Gene and Adhesion Molecule Expression in Psoriatic Skin Lesions", Annals of New York Academy of Sciences, vol. 696, pp. 250-256, 1993.

Lennard-Jones, "Defining Ulcer Depth in Colitis", The Lancet, vol. 347, pp. 1708, 1996.

Letvin, et al., "T Lymphocyte Surface Antigens in Primates", European Journal of Immunology, vol. 13, pp. 345-347, 1983.

Ley, et al., "The T Cell Receptor/CD3 Complex and CD2 Stimulate the Tyrosine Phosphorylation of Indistinguishable Patterns of Polypeptides in the Human T Leukemic Cell Line Jurkat", European Journal of Immunology, vol. 21, pp. 2203-2209, 1991.

Li, et al., "Enhancement of B cell responses by the interaction of CD2 with LFA-3", J. Tongji Med. Univ. 12(2):71-74 (1992).

Liao, T., et al., "Modification of Sialyl Residues of Sialoglycoprotein(s) of the Human Erythrocyte Surface," J. Biol. Chem., 248(23), pp. 8247-8253 (Dec. 10, 1973).

Lichtiger, et al., "Cyclosporine in Severe Ulcerative Colitis Refractory to Steroid Therapy", The New England Journal of Medicine, vol. 330, No. 26, pp. 1841-1845, 1994.

Lindelof, "Risk of Melanoma with Psoralen/Ultraviolet A Therapy for Psoriasis", Drug Safety, vol. 20, No. 4, pp. 289-297, 1999.

Llewellyn-Smith, et al., "Effects of Anti-CD4 Antibody Treatment on Lymphocyte Subsets and Stimulated Tumor Necrosis Factor Alpha Production: A Study of 29 Multiple Sclerosis Patients Entered into a Clinical Trial of cM-T412", Neurology, vol. 48, pp. 810-816, 1997.

Lorincz, "Cutaneous T-Cell Lymphoma (Mycosis Fungoides)", The Lancet, vol. 347, pp. 871-876, 1996.

Lotti, et al., "Neuropeptides and Skin Disorders. The New Frontiers of Neuro-Endocrine-Cutaneous Immunology", International Journal of Dermatology, vol. 38(9), pp. 673-675, 1999.

Low, "Biochemistry of the Glycosyl-Phosphatidylinositol Membrane Protein Anchors," Biochem. J., 244, pp. 1-13 (1987).

Lowe, "Initiating Neoral.RTM. Therapy", International Journal of Dermatology, vol. 36(suppl. 1), pp. 30-33, 1997.

Ludden, "Population Pharmacokinetics", Journal of Clinical Pharmacology, vol. 28, pp. 1059-1063, 1998.

Mackay, et al., "Naive and Memory T Cells Show Distinct Pathways of Lymphocyte Recirculation", J Exp Med. Mar. 1, 1990;171(3):801-17,.

Magilavy, et al., "Targeting CD2 for immunotherapy: results of a phase 1 trial with a LFA-3/IgG Fe fusion protein", Arthritis Rheum. 40(9-suppl.): S176 (1997) (Abstract).

Magilavy, et al., "Pharmacodynamic effects of LFA3TIP (Amevive) in patients with chronic plaque psoriasis (CPP) : Selective modulation of CD45RO+lymphocytes", J. Invest. Dermatol 112(4):609 (1999) (Abstract).

Mahrle, et al., "Anti-lnflamatory Efficacy of Low-Dose Cyclosporin A in Psoriatic Arthritis. A Prospective Multicentre Study", British Journal of Dermatology, vol. 135, pp. 752-757, 1996.

Majeau et al. (1994), "Mechanism of lymphocyte function-associated molecule 3-Ig fusion proteins inhibition of T cell responses," J. of Immunol. 152 (6): 2753-2767 (1994).

Majeau, et al., "Low Affinity Binding of an LFA-3/IgG1 Fusion Protein to CD2+ T Cells is Independent of Cell Activation", Cell Adhesion and Communication, vol. 7, No. 3, pp. 267-279, 1999.

Majewski, et al., "Papillomavirus and Autoimmunity in Psoriasis", Immunology Today, vol. 20, No. 10, pp. 475-476, 1999.

Makgoba et al. (1989) "The CDA2-LFA-3 and LFA-1-ICAM Pathways: Relevance to T-Cell Recognition" Immunol. Today 10(12):417-422.

Makgoba et al., "Human T Cell Rosetting is Mediated by LFA-3 on Autologous Erythrocytes," Journ. Immunol., vol. 138(11), pp. 3587-3589 (1987).

Maniatis, et al., "Extraction, Purification, and Analysis of mRNA from Eukaryotic Cells", Molecular Cloning, A Laboratory Manual 187-209 (Cold Spring Harbor Laboratory, 1982).

March, et al., "A Simplified Method for Cyanogen Bromide Activation of Agarose for Affinity Chromatography", Anal. Biochem., 60, 149-152 (1974).

Martz and Gromkowski (1985) "Lymphocyte Function-Associated Antigens: Regulation of Lymphocyte Adhesions in Vitro and immunity in Vivo" Mechanisms of Cell-Mediated Cytotoxicity II (Plenium Press, 1985) pp. 291-310.

Matis (1990) "The molecular basis of T-cell specificity" Ann. Rev. Immunol. 8:65-82.

Matsuyama, et al., "The Quantitative and Qualitative Defect of CD4+CD45RO+ Memory-Type T Cells are Involved in the Abnormality of TH1 Immunity in Atopic Dermatitis Patients", Clinical and Experimental Allergy, vol. 29, pp. 687-694, 1999.

Maxam et al., "Sequencing End-Labeled DNA with Base-Specific Chemical Cleavages", Methods in Enzymology, 65:499-560 (Academic Press,1980).

Maxam, et al., "A New Method for Sequencing DNA", Proc. Natl. Acad. Sci., 74, 560-564 (1977).

Mazzanti, et al., "Methotrexate and Cyclosporin Combined Therapy in Severe Psoriatic Arthritis. A Pilot Study", Acta Derm Venereol (Stockh), Suppl. 186, pp. 116-117, 1994.

McFarland, "Complexities in the Treatment of Autoimmune Disease", Science, vol. 274, pp. 2037-2038, 1996.

Meffert, and Sonnichsen, "Acitrecin in the Treatment of Severe Psoriasis: A Randomized Double-Blind Study Comparing Acitrecin and Etretinate", Acta Derm Venereol (Stockh), Suppl.146, pp. 176-177, 1989.

Meffert, et al., "Low-Dose (1.25 mg/kg) Cyclosporin A: Treatment of Psoriasis and Investigation of the Influence on Lipid Profile", Acta Derm Venereol (Stockh), vol. 77, pp. 137-141, 1997.

Meier et al (1995) "Immunomodulation by LFA3TIP, an LFA-3/IgG.sub.I fusion protein: cell line dependent glycosylation effects on pharmacokinetics and pharmacodynamic markers," Therapeutic Immunology 2(2): 159-171.

Meingassner, et al., "A Novel Anti-Inflamatory Drug, SDZ ASM 981, for the Topical and Oral Treatment of Skin Diseases: in Vivo Pharmacology", British Journal of Dermatology, vol. 137, pp. 568-576, 1997.

Menter, and Barker, "Psoriasis Practice", The Lancet, vol. 338, pp. 231-234, 1991.

Merck Manual, Seventeenth Ed. pp. 303-313, 448, 725-729, 1474-1476.

Mesalamine Study Group, "An Oral Preparation of Mesalamine as Long-Term Maintenance Therapy for Ulcerative Colitis: A Randomized Placebo-Controlled Trial", Annals of Internal Medicine, vol. 124, pp. 204-211, 1996.

Meuer et al. (1984) "An Alternative Pathway of T Cell Activation: A Functional Role for the 50 kd TII Sheep Erythrocyte Receptor Protein" Cell 36:897-906.

Meuer et al. (1984) "The human T-cell receptor" Ann. Rev. Immunol. 2:23-50.

Meuer et al. (1989) "The Alternative Pathway of T Cell Activation: Biology, Pathophysiology, and Perspectives for Immunopharmacology" Clin. Immunol. Immunopath. 50:S133-S138.

Michler, et al. "Pretransplant blood transfusion in a primate cardiac xenograft model", Curr. Surg. 44(1):42-45 (1987).

Michler, et al., "Technique for primate heterotopic cardiac xenotransplantation", J. Med. Primatol. 14:357-362 (1985).

Michler, et al., "Prolongation of primate cardiac xenograft survival with cyclosporine", Transplantation 44(5):632-636 (1987).

Mikayama, et al., "Molecular cloning and functional expression of a cDNA encoding glycosylation-inhibiting factor", PNAS 90:10056-10060 (1993).

Miller et al. (1993) "Specific interaction of lymphocyte function associated antigen 3 with CD2 can inhibit T cell responses," J. Exp. Med. 178: 211-222.

Moingeon et al. (1989) "The Structural Biology of CD2" Immunol. Rev. 111:111-144.

Moingeon et al. (1989), "CD2-mediated adhesion facilitates T lymphocyte antigen recognition function," Nature 339: 312-339.

Moingeon et al. (1991) "Complementary Roles for CD2 and LFA-1 Adhesion Pathways During T Cell Activation" Eur. J. Immunol. 21:605-610.

Mordenti, "Forecasting Cephalosporin and Monobactam Antibiotic Half-Lives in Humans from Data Collected in Laboratory Animals", Antimicrobial Agents and Chemotherapy, vol. 27, No. 6, pp. 887-891, 1985.

Moreland, et al. "Use of a chimeric monoclonal anti-CD4 antibody in patients with refractory rheumatoid arthritis", Arthritis and Rheumatism 36(3) (1993).

Moreland, et al., "Biological Agents for Treating Rheumatoid Arthritis", Arthritis and Rheumatism, vol. 40, No. 3, pp. 397-409, 1997.

Morison, et al., "Consensus Workshop on the Toxic Effects of Long-Term PUVA Therapy" Arch Dermatol, vol. 134, pp. 595-598, 1998.

Moroney, S. E., et al., "Modification of the Binding Site(s) of Lectins by an Affinity Column Carrying an Activated Galactose-Terminated Ligand," Biochemistry, 26, pp. 8390-8398 (1987).

Morrison, S. L., "Transfectomas Provide Novel Chimeric Antibodies," Science, 229, pp. 1202-1207 (Sep. 20, 1985).

Mosmann, et al., "The Expanding Universe of T-Cell Subsets: Th1, Th2 and More", Immunology Today, vol. 17, No. 3, pp. 138-145, 1996.

Mrowietz, et al., "Long-Term Maintenance Therapy with Cyclosporine and Posttreatment Survey in Severe Psoriasis: Results of a Multicenter Study", Journal of the American Academy of Dermatology, vol. 33, No. 3, pp. 470475, 1995.

Muchenberger, et al., "The Combination of Oral Acitrecin and Bath PUVA for the Treatment of Severe Psoriasis", British Journal of Dermatology, vol. 137, pp. 587-589, 1997.

Mulligan, et al., "Selection for Animal Cells that Express the *Escherichia coli* Gene Coding for Xanthine-Guanine Phophoribosyltransferase", Proc. Natl. Acad. Sci. U.S.A., 78:2072-2076 (1981).

Murray, et al., "A 12-Month Treatment of Severe Psoriasis with Acitrecin: Results of a Canadian Open Multicenter Study", Journal of the American Academy of Dermatology, vol. 24, No. 4, pp. 598-602, 1991.

Mussi, et al., "Serum TNF-Alpha Levels Correlate with Disease Severity and are Reduced by Effective Therapy-in Plaque-Type Psoriasis", J Biol Regul Homeost Agents, vol. 11, No. 3, pp. 115-118, 1997.

Nair, et al., "Evidence for Two Psoriasis Susceptibility Loci (HLA and 17q) and Two Novel Candidate Regions (16q and 20p) by Genome-Wide Scan", Human Molecular Genetics, vol. 6, No. 8, pp. 1349-1356, 1997.

Nakakura, et al., "Potent and effective prolongation by anti-LFA-1 monoclonal antibody monotherapy of non-primarily vascularized heart allograft survival in mice without T cell depletion", Transplantation 55(2):412-417 (1993).

Naldi, et al., "Analytical Epidemiology in Psoriasis", Journal of Investigative Dermatology, vol. 102, No. 6, pp. 19S-23S, 1994.

Nathan et al. (1986) "Local and Systemic Effects of Intradermal Recombinant Interferon-gamma in Patients with Lepromatous Leprosy" New Eng. J. Med. 315(1):6-15.

Ngo et al. "Computational complexity, protein structure prediction, and the Levinthal paradox" in the Protein Folding Problem and Tertiary Structure Prediction, 1994, Merz et al. (Ed.), Birkhauser, Boston, MA, pp. 433 and 492-495, 1994.

Nicolas, et al., "CD4 antibody treatment of severe psoriasis", Lancet 338:321 (1991).

Nickoloff, "The Cytokine Network in Psoriasis", Arch Dermatol, vol. 127, pp. 871-884, 1991.

Nickoloff, et al., "Accessory Cell Function of Keratinocytes for Superantigens: Dependence on Lymphocyte Function-Associated Antigen-1/Intercellular Adhesion Molecule-1 Interaction", The Journal of Immunology, vol. 150, No. 6, pp. 2148-2159, 1993.

Nickoloff, et al., "Cytokine Networks: Immunobiology Surfaces", The Journal of NIH Research, vol. 3, pp. 71-74, 1991.

Nishibu, et al., "Overexpression of Monocyte-Derived Cytokines in Active Psoriasis: A Relation to Coexistent Arthropathy", Journal of Dermatological Science, vol. 21, pp. 63-70, 1999.

Nouri et al. (1990) "Selective and non-selective loss of immunoregulatory molecules (HLA-A,B,C antigens and LFA-3) in transitional cell carcinoma" J. Br. Cancer 62:603-606.

O'Gorman, et al., "Genetic Polymorphisms associated with clinical improvement of chronic plaque psoriasis after treatment with alefacept", J. Inves. Derm. 124(4): A40 (2005) (Abstract).

Okayama, et al., "High-Efficiency Cloning of Full-Length cDNA", Mol. Cell. Biol., 2(2): 161-170 (1982).

Olivieri, et al., "Therapy with Cyclosporine in Psoriatic Arthritis", Seminars in Arthritis and Rheumatism, vol. 27, No. 1, pp. 36-43, 1997.

Osband et al. (1990) "Problem in the investigational Study and Clinical Use of Cancer Immunotherapy" Immunology today 11(6): 193-195.

Osborn et al. (1995), "Amino acid residues required for binding of lymphocyte function-associated antigen 3 (CD58) to its counter-receptor CD2," J. Exp. Med. 181(1): 429-434.

Park, and Youn, "Factors Influencing Psoriasis: An Analysis Based upon the Extent of Involvement and Clinical Type", The Journal of Dermatology, vol. 25, pp. 97-102, 1998.

Patel, et al., "Compatibility of Calcipotriene with Other Topical Medications", Journal of the American Academy of Dermatology, vol. 38, No. 6, pp. 1010-1011, 1998.

Pavli, et al., "Inflammatory Bowel Disease: Germs or Genes?", The Lancet, vol. 347, pp. 1198, 1996.

Pearson, et al., "Azathioprine and 6-Mercaptopurine in Crohn Disease: A Meta-Analysis", Annals of Internal Medicine, vol. 122, pp. 132-142, 1995.

Peckham, et al., "The Treatment of Severe Psoriasis", Arch Dermatol, vol. 123, pp. 1303-1307, 1987.

Peng, et al., "Ligation of CD2 provides a strong helper signal for the production of the type 2 cytokines", Cell. Immunol., 181(1):76-85 (1997).

Pepino et al. (1989) "Primate Cardiac Alto- and Xenotransplantation: Modulation of the Immune Response with Photochemotherapy" Eur. Surg. Res. 21:105-113.

Pepinsky et al. (1991), "The increased potency of cross-linked lymphocyte function-associated antigen-3 (LFA-3) multimers is a direct consequence of changes in valency," J. Biol Chem. 266(27): 18244-18249.

Pepinsky, et al., "Purification and Partial Sequence Analysis of a 37-kDA Protein that Inhibits Phospholipase $A_2$ Activity from Rat Peritoneal Exudates", J. Bio. Chem., 261(9), 4239-4246 (1986).

Peterson (1987) "Monoclonal Antibody and Ligand Binding Sites of the T Cell Erythrocyte Receptor (CD2)" Nature 329:842-846.

Peterson, A. S., "Genetic and Biochemical Analysis of CD2, LFA-3 Interation," in Genetic Analysis of CD2/LFA and CD4/HIV Interactions, Chapter 1, pp. 1-13, Figure 1A (Harvard University, Cambridge, Massachusetts 1988).

Pettit, "Oral Retinoid for Psoriasis: A Report of a Double Blind Study", Acta Derm Venereol Suppl (Stockh). 1979;59(85):133-6.

Petzelbauer, et al., "Cyclosporin A Suppresses ICAM-1 Expression by Papillary Endothelium in Healing Psoriatic Plaques", The Journal of Investigative Dermatology, vol. 96, No. 3, pp. 362-386, 1991.

Picker et al. (1990) "A Unique Phenotype of Skin-associated Lymphocytes in Humans" Am. J. Path. 136(5):1053-1068.

Pitzalis, "Skin and joint disease in psoriatic arthritis: What is the link?" Br. J. Rheum. 37(5): 480-483 (1998).

Pitzalis, et al., "Selective Migration of the Human Helper-Inducer Memory T Cell Subset: Confirmation by in Vivo Cellular Studies", European Journal of Immunology, vol. 21, pp. 369-376, 1991.

Platt, et al. "Transplantation of discordant xenografts: a review of progress", Immunol. Today 11(12):450-456 (1990).

Podolsky, "Inflammatory Bowel Disease", The New England Journal of Medicine, vol. 325, No. 13, pp. 928-1014, 1991.

Poikolainen, et al., "Excess Mortality Related to Alcohol and Smoking Among Hospital-Treated Patients with Psoriasis", Arch Dermatol, vol. 135, pp. 1490-1493, 1999.

Poizot-Martin et al. (1991) "Are CD4 antibodies and peptide T new treatments for psoriasis" The Lancet 337:1477.

Polito, et al., "Preliminary Evidence for Genetic Anticipation in Crohn's Disease", The Lancet, vol. 347, pp. 798-800, 1996.

Prens, et al., "T Lymphocytes in Psoriasis", Clinics in Dermatology, vol. 13, pp. 115-129, 1995.

Prentice "Deaths Linked to Growth Hormone" The Times (London), Apr. 6, 1991 (Cited for argument).

Prince (1989) "Requirement for Both the CD3/T Cell Receptor Complex and the CD2/Lymphocyte Function-Associated Antigen-3 Adhesion System in Monocyte-Independent T Cell Activation by Oxidized Erythrocytes" Immunol. Investigations 18:1081-1093.

Prinz et al. (1991) "Chimaeric CD4 monoclonal antibody in treatment of generalised pustular psoriasis" The Lancet 338:320-321.

Prinz, "Which T Cells Cause Psoriasis?", Clinical and Experimental Dermatology, vol. 24, pp. 291-295, 1999.

Qin et al, "Induction of classical transplantation tolerance in the adult", J. Exp. Med. 169(3):779-794 (1989).

Queen et al, "A humanized antibody that binds to the interleukin 2 receptor", PNAS 86:10029-10033 (1989).

Ramakrishnan, S. and L. L. Houston, "Comparison of the Selective Cytotoxic Effects of Immunotoxins Containing Ricin A Chain or Pokeweed Antiviral Protein and Anti-Thy 1.1 Monoclonal Antibodies," Cancer Research, 44, pp. 201-208 (Jan. 1984).

Rao, et al., "C-Terminal Modification Occurs in Tissue Culture Produced OKT3", Biopharm—The Technology & Business of Biopharmaceuticals, 1991, V4, N10, p. 38-43.

Rue, et al., "Longterm combination therapy of refractory and destructive rheumatoid arthritis with methotrexate (MTX) and intramuscular gold or other disease modifying antirheumatic drugs compared to MTX monotherapy", J. Rheumatol. 25(8):1485-1492 (1998).

Recny et al. (1990) "Structural and Functional Characterization of the CD2 Immunoadhesion Domain" J. Biol. Chem. 265(15):8542-8549.

Reemtsma, "Xenografts", Transplantation Proceedings 21(1):517-518 (1989).

Refsum, et al., "Fasting Plasma Homocysteine as a Sensitive Parameter of Antifolate Effect: A Study of Psoriasis Patients Receiving Low-Dose Methotrexate Treatment", Clinical Pharmacology Therapy, vol. 46, No. 5, pp. 510-520, 1989.

Reichlin, M., "Use of Glutaraldehyde as a Coupling Agent for Proteins and Peptides," in Methods in Enzymology, 70, edited by Van Vunakis et al., (Academic Press, New York, 1980) pp. 159-165 (1980).

Reichmann, et al., "Reshaping human antibodies for therapy", Nature 332:323-327 (1998).

Reilly, et al., "Compartmental Analysis of the Pharmacokinetics of Radioiodinated Monoclonal Antibody B72.3 in Colon Cancer Patients", Nucl. Med. Biol, vol. 20, No. 1, pp. 57-64, 1993.

Reilly, et al., "Problems of Delivery of Monoclonal Antibodies; Pharmaceutical and Pharmacokinetic Solutions", Clinical Pharmacokinetics, vol. 28, No. 2, pp. 126-142, 1995.

Reimann et al.; "In Vivo Administration of Lymphocyte-Specific Monoclonal Antibodies in Nonhuman Primates" (Transplantation—Dec. 1989 pp. 906-912).

Richardson, N. E., et al., "Adhesion Domain of Human T11 (CD2) is Encoded by a Single Exon," Proc. Natl. Acad. Sci. (USA), 85, pp. 5176-5180 (1988).

Riggs et al. (1996), "The pharmacokinetic/pharmacodynamic (PK/PD) modeling of immunoglobin fusion protein, LFA3TIP, using a non-linear saturable cell activity model," Pharmaceutical Research 13 (9 Supp.): s398 (Abstract).

Rincon and Patarroyo (1989) "Effect of Antibodies From the T Cell (CD2' Only) and the NK/Non-Lineage (New Panel Only) Sections on Adhesion of Jurkat (T) Cell to Human Erythrocytes" Tissue Antigens 33:285.

Rivers, et al., "UVA Sunbeds: Tanning, Photoprotection, Acute Adverse Effects and Immunological Changes", British Journal of Dermatology, vol. 120, pp. 767-777, 1989.

Rodriguez, et al., "Optic Neuritis Posed a 40-Year Risk of 60% for Multiple Sclerosis", ACP Journal Club, vol. 122-123: 21, 1995.

Roitt, Immunology, Gower Medical Pub. (1985)—Immunology textbook.

Rose, "Risks of Cardiac Transplantation", Ann.Thoracic Surg. 47:645 (1989).

Rose, et al. "Immunosuppression in Cardiac Transplantation", Biblthca Cardiol. 43:1-9 (1988).

Rose, et al. "Humoral immune responses after cardiac transplantation: Correlation with fatal rejection and graft atherosclerosis", Surgery 106(1):203-208 (1989).

Rose, et al., "Cardiac Xenotransplantation", Prog. Cardiovasc. Diseases 33(2):105-117 (1990).

Rose, et al., "Present Status of Human Cardiac Allografts and Prospects for Xenografts", Trans Am. Soc. Artif. Intern. Organs 34:19-23 (1988).

Rudinger, J. "Characteristics of the amino acids as components of a peptide hormone sequence" in Peptide Hormones, Parson, J. A. (Ed.), University Park Press, Baltimore, MD, pp. 1-7, 1976.

Sachs, et al., "Immunology of Xenograft Rejection", Hum. Immunol. 28:245-251 (1990).

Salmi, et al., "Dual Binding Capacity of Mucosal Immunoblasts to Mucosal and Synovial Endothelium in Humans: Dissection of the Molecular Mechanisms", Journal of Experimental Medicine, vol. 181, pp. 137-149, 1995.

Salmi, et al., "Homing of Mucosal Leukocytes to Joints: Distinct Endothelial Ligands in Synovium Mediate Leukocyte-Subtype Specific Adhesion", Journal of Clinical Investigation, vol. 99, No. 9, pp. 2165-2172, 1997.

Sanchez-Madrid, F. et al., "Three Distinct Antigens Associated with Human T-Lymphocyte-Mediated Cytolysis: LFA-1, LFA-2, and LFA-3," Proc. Natl. Acad. Sci, USA, 79, pp. 7489-7493 (Dec. 1982).

Sander, et al., "The Annual Cost of Psoriasis", Journal of the American Academy of Dermatology, vol. 28, No. 3, pp. 422-425, 1993.

Sanders et al. (1988) "T Cell Adhesion Receptors LFA-1 and CD2 and Their Ligands ICAM-1 and LFA-3" Analysis in Adhesion, Cell Mediated Lysis, and As Markers OfT Cell Subsets in the T-Cell Receptor, A.R. Liss, Inc., pp. 269-279.

Sanders, et al., "Human Memory T Lymphocytes Express Increased Levels of Three Cell Adhesion Molecules (LFA-3, CD2, and LFA-1) and Three Other Molecules (UCHL1, CDw29, and Pgp-1) and have enhanced IFN-.gamma. Production", The Journal of Immunology, vol. 140, No. 5, pp. 1401-1407, 1988.

Savage et al. (1991), "Endothelial cell lymphocyte function-associated antigen-3 and an unidentified ligand act in concert to provide costimulation to human peripheral blood CD4.sup.+ T cells," Cellular Immunology 137(1): 150-163.

Sayre et al. (1987), "Molecular cloning and expression of T11 cDNAs reveal a receptor-like structure on human T lymphocytes" Chemical Abstracts 107(15): Abstract 128218x.

Sayre, et al. "Molecular cloning and expression of T11 cDNAs reveal a receptor-like structure on human T lymphocytes", PNAS 84:2941-2945 (1987).

Schneider, et al., (Abstract) "A pilot study of the safety and efficacy of Alefacept in subject with active rheumatoid arthritis on methotrexate" European League Against Rheumatism (2003).

Schopf (1986) "Stimulation of T Cells by Autologous Molecular Leukocytes and Epidermal Cells in Psoriasis" Arch. Dermatol. Res. 279:89-94.

Schopf, "Interactions between epidermal cells and lymphocytes in psoriasis", Immunology Today 7:358 (1988).

Schraven, et al., "Alternations of CD2 Association with T Cell Receptor Signaling Molecules in 'CD2 Unresponsive' Human T Lymphocytes", European Journal of Immunology, vol. 23, pp. 119-123, 1993.

Schwartz, et al., "Identification of the TS2/18-Recognized Epitope on the CD2 Molecule as a Target for Suppression of T Cell Cytokine Synthesis", The Journal of Immunology, vol. 154, pp. 5813-5820, 1995.

Schweighoffer, et al. "Adhesions cascades: diversity through combinatorial strategies", Curr. Opin. Cell. Biol. 4(5):824-829 (1991).

Seed, et al. (1987) "Molecular Cloning of the CD2 Antigen, the T-Cell Erythrocyte Receptor, by a Rapid immunoselection procedure" Proc. Natl. Acad. Sci. USA 84:3365-3369.

Seed, B. "An LFA-3 cDNA Encodes a Phospholipid-Linked Membrane Protein Homologous to its Receptor CD2," Nature, 329, pp. 840-842 (1987).

Seed, et al., "Molecular Cloning of the CD2 Antigen, the T-Cell Erythrocyte Receptor, by a Rapid Immunoselection Procedure," Proc. Natl. Acad. Sci. USA, 84, pp. 3365-3369 (May 1987).

Selvaraj et al. "Deficiency of Lymphocyte Function Associated Antigen 3 (LFA3) in Paroxysmal Nocutrnal Hemoglobinuria," J. Exp. Med., 166, pp. 1011-1025 (1987).

Selvaraj et al. (1987) "The T Lymphocyte Glycoprotein CD2 (LFA-2/T11/E-Rosette Receptor) Binds the Cell Surface Ligand LFA-3" FASEB J. 46(3):447 Abstract 760.

Selvaraj, P. et al., "The T Lymphocyte Glycoprotein CD2 Binds the Cell Surface Ligand LFA-3," Nature, 326, pp. 400-403 (Mar. 1987).

Semnani et al. (1994), "Costimulation by purified intercellular adhesion molecule 1 and lymphocyte function-associated antigen 3 induces distinct proliferation, cytokine and cell surface antigen profiles in human "naive" and "memory" CD4.sup.+ T cells," J. Exp. Med. 180:2125-2135.

Seo, "Evaluation of Disease Activity in Patients with Moderately Active Ulcerative Colitis: Comparisions Between a New Activity Index and Truelove and Witts' Classification", The American Journal of Gastroenterology, vol. 90, No. 10, pp. 1759-1763, 1995.

Sewell et al. (1986) "Molecular Cloning of the Human T-Lymphocyte Suface CD2 (T11) Antigen" Proc. Natl. Acad. Sci. USA 83:8718-8722.

Shahidullah, et al., "Etretinate Therapy for Psoriasis and Other Keratinizing Disorders: A 10-Year Retrospective Study in Singapore", International Journal of Dermatology, vol. 32, No. 9, pp. 686-689, 1993.

Shanahan, "Pathogenesis of Ulcerative Colitis", The Lancet, vol. 342, pp. 407-411, 1993.

Shaw et al. (1986) "Two Antigen-Independent Adhesion Pathways Used by Human Cytotoxic T-Cell Clones" Nature 323:262-264.

Shaw, et al., "Cyclosporin A and Vitamin D Metabolism: Studies in Patients with Psoriasis and in Rats", Clinical Science, vol. 86, pp. 627-632, 1994.

Shaw, S. and G. E. Ginther Luce, "The Lymphocyte Function-Associated Antigen and (LFA)-1 CD2/LFA-3 Pathways of Antigen-Independent Human T Cell Adhesion," J. Immunol., 139, pp. 1037-1045 (Aug. 15, 1987).

Shimizu, et al "Four Molecular Pathways of T Cell Adhesion to Endothelial Cells: roles of :FA-1, VCAM-1 and ELAM-1 and Changes in Pathway Hierarchy Under Different Activation Conditions", J. Cell. Biol. 113(5):1203-1212 (1991).

Short, J. M., et al., ".lambda. ZAP: A Bacteriophage Expression Vector with in Vivo Excision Properties," Nucleic Acids Research, 16(15), pp. 7583-7600 (1988).

Shupak, "Maintenance Therapy with Neoral.RTM.", International Journal of Dermatology, vol. 36, pp. 34-36, 1997.

Simon et al. (1991) "Adhesion molecules CD11a, CD18, and ICAM-2 on Human Epidermal Langerhans Cells Serve a Functional Role in the Activation of Alloreactive T Cells" Soc. Invest. Dermat. 96(1): 148-151.

Singer et al. (1990) "Thymocyte LFA-1 and Thymic Epithelial Cell ICAM-1 Molecules Mediate Binding of Activated Human Thymocytes to Thymic Epithelial Cells" J. Immunol. 144(8):2931-2939.

Singer, K.H. et al. "The Role of Adhesion Molecules in Epithelial—T-Cell Interactions in Thymus and Skin", J. Invest. Dermatol. 94 (6) Supplement: 85S-90S.

Singh, et al., "Acute Immobilization Stress Triggers Skin Last Cell Degranulation via Corticotropin Releasing Hormone, Neurotensin, and Substance P: A Link to Neurogenic Skin Disorders", Brain Behavior, and Immunity, vol. 13, pp. 225-239, 1999.

Smith, et al. (1990) "Cellular Expression of Lymphocyte Function Associated Antigens and the Intercellular Adhesion Molecule-1 in Normal Tissue" J. Clin. Path. 43 (11):893-900.

Smith, and Barker, "Cell Trafficking and Role of Adhesion Molecules in Psoriasis", Clinics in Dermatology, vol. 13, pp. 151-160, 1995.

Sofer and Britton "Designing an Optimal Chromatographic Purification Scheme for Proteins" Bio/Techniques 1(4):198-203 (1983).

Somerville, and Scott, "Neoral-New Cyclosporin for Old?", British Journal of Rheumatology, vol. 36, pp. 1113-1115, 1997.

Southern, E. M. "Detection of Specific Sequences Among DNA Fragments Separated by Gel Electrophoresis", J. Mol. Biol., 98, 503-517 (1975).

Spadaro, et al., "Comparison of cyclosporine A and methotrexate in the treatment of psoriatic arthritis: a one-year prospective study", Clin. Exp. Rheum. 13:589-593 (1995).

Springer "Adhesion Receptors of the Immune System" Nature 346:425-434.

Springer (1987) "The Lymphocyte Function-Associated LFA-1, CD2, and LFA-3 Molecules: Cell Adhesion Receptors of the Immune System" Ann. Rev. Immunol. 5:223-252.

Spuls et al., "A Systematic Review of Five Systematic Treatments for Severe Psoriasis", British Journal of Dermatology, vol. 137, pp. 943-949, 1997.

Srinivasachar, K. and D. M. Neville, Jr., "New Protein Cross-Linked Reagents That are Cleaved by Mild Acid," Biochemistry, 28(4), pp. 2501-2509 (1989).

Staunton et al. (1989) "Molecular characterization of ICAM-1 and ICAM-2; Alternate Ligands for LFA-1" Tissue Antigens 33:287 (Abstract).

Stedman's Medical Dictionary, (1976) The Williams & Wilkins Company, Baltimore, MD, p. 810.

Stern, "Narrowband UV-B and Psoriasis", Arch Dermatol, vol. 133, pp. 1587-1588, 1997.

Stern, "Psoriasis", The Lancet, vol. 350, pp. 349-353, 1997.

Stern, "Utilization of Outpatient Care for Psoriasis", Journal of the American Academy of Dermatology, vol. 35, No. 4, pp. 543-549, 1996.

Stern, et al., "Malignant Melanoma in Patients Treated for Psoriasis with Methoxsalen (Psoralen) and Ultraviolet A Radiation (PUVA)", The New England Journal of Medicine, vol. 336, No. 15, pp. 1041-1045, 1997.

Stern, et al., "The Safety of Etretinate as Long-Term Therapy for Psoriasis: Results of the Etretinate Follow-Up Study", Journal of the American Academy of Dermatology, vol. 33, No. 1, pp. 44-52, 1995.

Storkus, and Dawson, "Target Structures Involved in Natural Killing (NK): Characteristics, Distribution, and Candidate Molecules", Immunology vol. 10, No. 5, 393-416, 1991.

Strand, "The Future Use of Biologic Therapies in Combination for the Treatment of Rheumatoid Arthritis", J. Rhematol. 23 (suppl. 44):91-96 (1996).

Sultan, et al., "Blockade of CD2-LFA-3 Interactions Protects Human Skin Allografts in Immunodeficient Mouse/Human Chimeras", Nature Biotechnology, vol. 15, pp. 759-762, 1997.

Suranyi et al. (1991) "Lymphocyte Adhesion Molecules in T Cell-Mediated Lysis of Human Kidney Cells" Kidney International 39:312-319.

Sutherland, et al., "Standards for Trials of Therapy in Inflammatory Bowel Disease", Inflammatory Bowel Diseases, vol. 3, No. 4, pp. 277-283, 1997.

Tadini (1989) "Adhesion Molecules Expression in Psoriasis" J. Invest. Dermatol. 93(2):309A (Abstract).

Talwar, et al., "Sequential Clinico-Histological Studies in Psoriasis Following Methotrexate Therapy", Ind J Dermatol Venereol Leprol, vol. 61, pp. 284-287, 1995.

Tang and Udey (1991) "Inhibition of Epidermal Langerhans Cell Function by Low Dose of Ultraviolet B Radiation" J. Immunol: 146(10):3347-3355.

Task Force of the Working Group on Arrhythmias of the European Society of Cardiology, "The Early Termination of Clinical Trials: Causes, Consequences, and Control", European Heart Journal, vol. 15, pp. 721-738, 1994.

The Merck Manual of Diagnosis and Therapy Sixteenth Edition Edited by Berkow et al., Merck Research Laboratories, Rahway NJ 1992, pp. 2435-2445.

Thomas, et al., "Transdermal Nicotine as Maintenance Therapy for Ulcerative Colitis", The New England Journal of Medicine, vol. 332, No. 15, pp. 988-992, 1995.

Thomas, et al., "Purification of Membrane Proteins" in Methods in Enzymology, Deutscher, M. ed., (Academic Press, San Diego) 182: 499 (1990) (cited for argument).

Ticho, et al., "Reduced T cell monitoring in psoriasis patients receiving alefacept: results of clinical studies and mathematical modeling", J. Inves. Derm. 124(4): A40 (2005) (Abstract).

Traupe, "The Puzzling Genetics of Psoriasis", Clinics in Dermatology, vol. 13, pp. 99-103, 1995.

Trembath, et al., "Identification of a Major Susceptibility Locus on Chromosome 6p and Evidence for Further Disease Loci Revealed by a Two Stage Genome-Wide Search in Psoriasis", Human Molecular Genetics, vol. 6, No. 5, pp. 813-820, 1997.

Uchio, et al., "Suppression of Experimental Uveitis With Monoclonal Antibodies to ICAM-1 and LFA-1", Invest. Opthamol. Vis. Sci. 35(5):2626-2631 (1994).

Ullman et al. (1990) "Transmission of Signals from T Lymphocyte Antigen Receptor to the Genes Responsible for Cell Proliferation and Immune Function: The Missing Link" Ann. Rev. lmmunol. 8:421-452.

Urlaub, and Chasin, "Isolation of Chinese Hamster Cell Mutants Deficient in Dihydrofolate Reductase Activity", Proc Natl Acad Sci, vol. 77, No. 7, pp. 4216-4220, 1980.

Urlaub, et al., "Effect of Gamma Rays at the Dihydrofolate Reductase Locus: Deletions and Inversions", Somatic Cell and Molecular Genetics, vol. 12, No. 6, pp. 555-566, 1986.

Valdimarsson et al. (1986) "Psoriasis: a disease of abnormal keratinoctye proliferation induced by T lymphocytes" Immunol. Today 7:256-259.

Valdimarsson, et al., "Psoriasis: A T-Cell-Mediated Autoimmune Disease Induced by Streptococcal Superantigens?", Immunology Today, vol. 16, No. 3, pp. 145-149, 1995.

Van De Kerkhof, "An Update on Vitamin D3 Analogues in the Treatment of Psoriasis", Skin Pharmacology and Applied Skin Physiology, vol. 11, pp. 2-10, 1998.

Van De Kerkhof, "Reduction of Epidermal Abnormalities and Inflammatory Changes in Psoriatic Plaques During Treatment with Vitamin D3 Analogs", Journal of Investigative Dermatology Symposium Proceedings, vol. 1, pp. 78-81, 1996.

Van De Kerkhof, "Review: The Management of Psoriasis", Netherlands Journal of Medicine, vol. 52, pp. 40-45, 1998.

Van De Kerkhof, "The Psoriasis Area and Severity Index and Alternative Approaches for the Assessment of Severity: Persisting Areas of Confusion", British Journal of Dermatology, vol. 137, pp. 661-662, 1997.

Vand De Kerkhof, et al., "Evaluation of Topical Drug Treatment in Psoriasis", Dermatology, vol. 197, pp. 31-36, 1998.

Van De Kerkhof, et al., "The Effect of Addition of Calcipotriol Ointment (50 .mu.g/g) to Acitretin Therapy in Psoriasis", British Journal of Dermatology, vol. 138, pp. 84-89, 1998.

Van Der Merwe, et al., "Human Cell-Adhesion Molecule CD2 Binds CD58 (LFA-3) with a Very Low Affinity and an Extremely Fast Dissociation Rate but does not Bind CD48 or CD59", Biochemistry, vol. 33, pp. 10149-10160, 1994.

Van Der Rhee, et al., "Combined Treatment of Psoriasis with a New Aromatic Retinoid (Tigason) in Low Dosage Orally and Triamcinolone Acetonide Cream Topically: A Double-Blind Trial", British Journal of Dermatology, vol. 102, pp. 203-211, 1980.

Van Kooyk, et al., "Enhancement of LFA-1-Mediated Cell Adhesion by Triggering through CD2 or CD3 on T Lymphocytes", Nature, vol. 342, pp. 811-813, 1989.

Van Noort, et al., "Cell Biology of Autoimmune Diseases", in International Review of Cytology: A Survey of Cell Biology, Jeon, K. ed. (Academic Press, San Diego, 1998), pp. 127-207.

Van Onselen, "Psoriasis in General Practice", Nursing Standard, vol. 12, No. 30, pp. 32-33, 1998.

Van Seventer et al. (1989) "The Three LFA-3 Specific Monoclonal Antibodies in the Non-Lineage panel of Workshop Monoclonal Antibodies All Inhibit T-Cell Rosetting" Tissue Antigens 33:298 (Abstract).

Van Seventer, et al. "Roles of multiple accessory mulecules in T-cell activation", Curr. Opin. Immunol. 3(3):294-303 (1991).

Verhoeven, et al., "Combination Therapy in Rheumatoid Arthritis: Updated systematic review", Br. J. Rheum. 37:612-619(1998).

Verstuyf, et al., "Recent Developments in the Use of Vitamin D Analogues", Expert Opin Investig Drugs, vol. 9, No. 3, pp. 397-403, 1998.

Virella et al. (1988) "The Interaction of CD2 With Its LFA-3 Ligand Expressed by Autologous Erythrocytes Results in Enhancement of B Cell Responses" Cell. Immunol. 116:308-319.

Vollger et al. (1987) "Thymocyte Binding to Human Tymic Epithelial Cells is Inhibited by Monoclonal Antibodies to CD-2 and LFA-3 Antigens" J. Immunol. 138(2):358-363.

Wahl, "The Impact of Psoriasis on Psychosocial Life Domains: A Review", Scandinavian Journal of Caring Science, vol. 11, pp. 243-249, 1997.

Wahl, et al., "Sulfasalazine: A Potent and Specific Inhibitor of Nuclear Factor Kappa B", Journal of Clinical Investigation, vol. 101, No. 5, pp. 1163-1174, 1998.

Waldmann (1991) "Monoclonal Antibodies in Diagnosis and Therapy" Science 252:1657-1662.

Wallner et al (1987) "Primary Structure of Lymphocyte Function-Associated Antigen 3 (LFA-3)—The Ligand of the Lymphocyte CD2 Glycoprotein" J. Exp. Med. 166(4):923-931.

Wallner, et al., "Cloning and Expression of Human Lipocortin, a Phospholipase A2 Inhibitor with Potential Anti-Inflammatory Activity", Nature, 320(6), 77-81 (1986).

Walters, et al., "Suberythemogenic narrow-band UVB is markedly more effective than conventional UVB in treatment of psoriasis vulgaris", J.Acad. Dermatol. 40(6) 893- 900.

Wang, et al., "Structure of a Heterophilic Adhesion Complex between the Human CD2 and CD58 (LFA-3) Counterreceptors", Cell, vol. 97, pp. 971-803, 1999.

Wang, X. et al., "A Vector That Expresses Secreted Proteins on the Cell Surface," DNA, 8(10), pp. 753-758 (Dec. 1989).

Wanqing, et al., "Clinical Study of Cyclosporin A for Psoriasis in China", Annals of Dermatology, vol. 7, No. 4, pp. 313-317, 1995.

Watanabe, et al., "Effect of recombinant soluble CD4 in rhesus monkeys infected with immunodeficiency virus of macaques", Nature 337:267(1989) (cited for argument.

Webb et al. (1990) "LFA-3, CD44, and CD45: Physiologic Triggers of Human Monocyte TNF and IL-1 Release" Science 249:1295-1297.

Weinblatt, et al., "Methotrexate for Chronic Diseases in Adults", The New England Journal of Medicine, vol. 332, No. 5, pp. 330-331, 1995.

Weinblatt, et al., "Efficacy of Methotrexate.In Rheumatoid Arthritis", Br. J. Rheum. 34(Supp 2):43-48 (1995).

Weiner, et al., "Phase I Evaluation of an Anti-Breast Carcinoma Monoclonal Antibody 260F9-Recombinant Ricin A Chain Immunoconjugate", Cancer Research, vol. 49, pp. 4062-4067, 1989.

Weinstein, "Psoriasis Therapy After Remission: The Next Step", International Journal of Dermatology, vol. 36(Suppl 1), pp. 37-40, 1997.

Weinstein, "Tazarotene Gel: Efficacy and Safety in Plaque Psoriasis", Journal of the American Academy of Dermatology, vol. 37, No. 2, pp. S33-S38, 1997.

Weinstein, et al., "Tazarotene Gel, a New Retinoid, for Topical Therapy of Psoriasis: Vehicle-Controlled Study of Safety, Efficacy, and Duration of Therapeutic Effect", Journal of the American Academy of Dermatology, vol. 37, No. 1, pp. 85-92, 1997.

Weiss, and Ashwell, "The Asialoglycoprotein Receptor: Properties and Modulation by Ligand", Baumann, P., et al. (ED.). Progress in Clinical and Biological Research, vol. 300.

Wendling, et al. "Therapeutic Use of Monoclonal Anti-CD4 Antibody in Rheumatoid Arthritis", J. Rheum. 18(3): 325-7 (1991) ) (abstract only).

Weyand, et al. "Immunosuppression by Anti-CD4 Treatments in Vivo", Transplantation 47(6):1039-1042(1989).

Whitcup, et al., "Monoclonal Antibodies against ICAM-1 (CD54) and LFA-1 (CD11a/CD18) Inhibit Experimental Autoimmune Uveitis", Clin. Immunol Immunopathol 67(2):143-150 (1993).

Whitmore, and Morison, "Melanoma after PUVA Therapy for Psoriasis", The New England Journal of Medicine, vol. 337, No. 7, pp. 502, 1997.

Willkens, et al., "Randomized, Double-Blind, Placebo Controlled Trial of Low-Dose Pulse Methotrexate in Psoriatic Arthritis", Arthritis and Rheumatism, vol. 27, No. 4, pp. 376-381, 1984.

Winter and Harris (1993) "Humanized antibodies" TiPS 14(5):139-142.

Wolska, et al., "Etretinate in Severe Psoriasis: Results of Double-Blind Study and Maintenance Therapy in Pustular Psoriasis", Journal of the American Academy of Dermatology, vol. 9, No. 6, pp. 883-887, 1983.
Wong et al., "Identification of a Partial cDNA Clone for the Human Receptor for Completement Fragments C3b/C4b," Proc. Natl. Acad. Sci. U.S.A., 82, 7711-7715 (1985).
Wong, et al., "Mechanisms of action of cyclosporine A in the treatment of psoriasis", Immunol. Today 14(2):69-74 (1993).
Wood, W. I. (1987) "Gene Cloning Based on Long Oligoneucleotide Probes", Meth. Entymol. 152:443-47.
Wright, et al., "Human Low-Dosage Parenteral Methotrexate Therapy: A Controlled Toxicity Study", Arch Derm, vol. 93, pp. 731-736, 1966.
Written Opinion PCT/US02/02314.
Yamashita, et al., "A multimeric form of soluble recombinant sheep LFA-3 (CD-58) inhibits human T-cell proliferation" Immunol. 92(1):39-44 (1997).
Yeh, et al., "Recombinant Soluble Human Complement Receptor Type 1 Inhibits Inflammation in the Reversed Passive Arthus Reaction in Rats", J. Immunol. 146(1):250 (1991) (cited for argument.
Yocum, et al., "Clinical and immunological effects of a Primatized Anti-CD4 Monoclonal Antibody in Active Rheumatoid Arthritis: Results of a Phase I, Single Dose, Dose Escalating Trial", Journal of Rheumatology, vol. 25, pp. 1257-1262, 1998.
Yong and Khwaja (1990) "Leukocyte Cellular Adhesion Molecules" Blood Reviews 4(4):211-225.
Young, et al., "A Prospective study of Renal Structure and Function in Psoriasis Patients with Cyclosporin", Kidney International, vol. 46, pp. 1216-1222, 1994.
Zachariae, "Alcohol Interaction with Drugs and its Effects on the Treatment of Skin Diseases", Clinics in Dermatology, vol. 17, pp. 443-445, 1999.
Zettlmeissl, et al., "Expression and Characterization of Human CD4: Immunoglobulin Fusion Proteins", DNA & Cell Biol. 9(5):347-353 (1990).
Zheng et al. (1990) "Expression of Intercellular Adhesion Molecule-1 and Lymphocyte Function-Associated Antigen-3 on Human Thyroid Epithelial Cells in Graves' and Hashimoto's Diseases" J. Autoimmunity 3:727-736.
Translation of Examiner's report for Czech Patent Application No. PV 2001-725.
File history for U.S. Appl. No. 60/098,456, filed Aug. 31, 1998.
File history for U.S. Appl. No. 09/796,033, filed Feb. 27, 2001.
File history for International Application No. PCT/US99/20026, filed Aug. 31, 1999.
File history for U.S. Appl. No. 11/398,908, filed Apr. 6, 2006.
File history for U.S. Appl. No. 60/307,688, filed Jul. 24, 2001.
File history for U.S. Appl. No. 60/382,459, filed May 22, 2002.
File history for International Application No. PCT/US02/21631, filed Jul. 10, 2002.
File history for U.S. Appl. No. 60/568,371, filed May 4, 2004.
File history for International Application No. PCT/US05/15531, filed May 4, 2005.
File history for U.S. Appl. No. 11/578,342, filed May 4, 2005.
File history for U.S. Appl. No. 60/542,311, filed Feb. 6, 2004.
File history for International Application No. PCT/US05/03907, filed Feb. 7, 2005.
File history for U.S. Appl. No. 10/588,323, filed Feb. 7, 2005.
File history for U.S. Appl. No. 60/568,955, filed May 7, 2004.
File history for International Application No. PCT/US05/16265, filed May 9, 2005.
File history for U.S. Appl. No. 11/578,391, filed May 9, 2005.
File history for U.S. Appl. No. 07/667,971, filed Mar. 12, 1991.
File history for U.S. Appl. No. 07/770,967, filed Oct. 7, 1991.
File history for International Application No. PCT/US92/02050, filed Mar. 12, 1992.
File history for U.S. Appl. No. 07/940,861, filed Oct. 21, 1992.
File history for U.S. Appl. No. 08/459,512, filed Jun. 2, 1995.
File history for U.S. Appl. No. 08/459,657, filed Jun. 2, 1995.
File history for U.S. Appl. No. 08/460,132, filed Jun. 2, 1995.
File history for U.S. Appl. No. 07/772,705, filed Oct. 7, 1991.
File history for U.S. Appl. No. 07/850,706, filed Mar. 12, 1992.
File history for International Application No. PCT/US92/08754, filed Oct. 6, 1992.
File history for U.S. Appl. No. 08/211,631, filed Apr. 5, 1994.
File history for U.S. Appl. No. 08/459,350, filed Jun. 2, 1995.
File history for U.S. Appl. No. 07/770,969, filed Oct. 7, 1991.
File history for U.S. Appl. No. 07/862,022, filed Apr. 2, 1992.
File history for International Application No. PCT/US92/08755, filed Oct. 6, 1992.
File history for U.S. Appl. No. 08/466,465, filed Jun. 6, 1995.
File history for U.S. Appl. No. 09/730,465, filed Dec. 5, 2000.
File history for U.S. Appl. No. 10/778,373, filed Feb. 13, 2004.
File history for U.S. Appl. No. 11/282,853, filed Nov. 18, 2005.
File history for U.S. Appl. No. 60/265,964, filed Feb. 1, 2001.
File history for International Application No. PCT/US02/02314, filed Aug. 8, 2002.
File history for U.S. Appl. No. 10/470,764, filed Jan. 25, 2002.
File history for U.S. Appl. No. 10/329,599, filed Dec. 26, 2002.
File history for U.S. Appl. No. 11/312,627, filed Dec. 20, 2005.
File history for U.S. Appl. No. 07/057,615, filed Jun. 3, 1987.
File history for International Application No. PCT/US88/01924, filed Jun. 3, 1988.
File history for U. S. Aeplication No. 07/365,107, filed Mar. 20, 1989.
File history for U.S. Appl. No. 07/537,031, filed Mar. 20, 1989.
File history for U.S. Appl. No. 08/381,299, filed Jan. 31, 1995.
File history for U.S. Appl. No. 07/237,309, filed Aug. 26, 1988.
File history for International Application No. PCT/US89/03652, filed Aug. 24, 1989.
File history for U.S. Appl. No. 07/959,550, filed Oct. 13, 1992.
File history for U.S. Appl. No. 08/261,463, filed Jun. 17, 1994 and File history for U.S. Appl. No. 08/460,243, filed Jun. 2, 1995.
File history for U. S. Application No. 60/623,364, filed Oct. 28, 2004.
File history for International Application No. PCT/US05/39070.
File history for U.S. Appl. No. 11/958,917, filed Dec. 18, 2007.
Gascoigne et al., "Secretion of a chimeric T-cell receptor-immunoglobulin protein", Proc. Natl. Acad. Sci., vol. 84, pp. 2936-2940 (1987).
Neuberger et al., "Recombinant antibodies possessing novel effector functions", Nature, vol. 312, pp. 604-608 (1984).
Traunecker et al., "Soluble CD4 molecules neutralize human immunodeficiency virus type 1", Nature, vol. 331, pp. 84-86 (1988).
Traunecker et al., "A novel approach for preparing anti-T cell receptor constant region antibodies", Eur. J. Immunol., vol. 16, pp. 851-854 (1986).
European Patent Office, European Search Report for European Application No. 05713080.0 issued Aug. 8, 2008.
Gordon et al., Journal of the American Academy of Dermatology, V. 50, No. 3, Mar. 2004, p. 152 (Abstract).
Krueger et al., Journal of the American Academy of Dermatology, V. 47., No. 6, Dec. 2002, pp. 821-833.
Krueger et al., Journal of the American Academy of Dermatology, V. 50, No. 3, Mar. 2004, p. 152 (Abstract).
Lebwohl et al., Archives of Dermatology, V. 139, No. 6, Jun. 1, 2003, pp. 719-727.
Lowe et al., International Journal of Dermatology, V. 42, No. 3, Mar. 2003, pp. 224-230.
Menter et al., Journal of the American Academy of Dermatology, V. 50, No. 3, Mar. 2005, p. 151 (Abstract).
Beers et al., Editors, Merck Manual of Diagnosis and Therapy, Seventeenth Edition, Merck Research Laboratories, Whitehouse Station, pp. 816-818 (1999).
Biogen IDEC, Safety Letter, Cambridge, MA (Oct. 2005).
Brazilian Industrial Property Office, Informal translation of Opinion in cognate Brazilian Application No. PI 9913285-0 (2009) for which a response was due Jan. 11, 2010 (informal translation by Dannemann Siemsen Bigler & Ipanema Moreira, Nov. 19, 2009).
CIPO, Official communication relative to related Canadian Application No. 2,565,259 mailed Apr. 30, 2009.
CIPO, Official communication relative to related Canadian Application No. 2,454,618 mailed May 1, 2009.
CIPO, Official communication relative to related Canadian Application No. 2,555,144 mailed Aug. 13, 2009.
EPO, Official communication relative to related European Application No. 05779311.9 mailed Jan. 29, 2008.

EPO, Official communication relative to related European Application No. 05779971.0 mailed Jul. 24, 2008.

EPO, Official communication relative to related European Application No. 02749865.8 mailed May 8, 2009.

Hoffmann, et al. Anti-CD2 (OX34) MoAb treatment of adjuvant arthritic rats: attenuation of established arthritis, selective depletion of CD4+ T cells, and CD2 down-modulation, Clin. Exp. Immunol., 110: 63-71 (1997).

Jung et al., Suppression of experimental autoimmune encephalomyelitis in Lewis rates by antibodies against CD2, Eur. J. Immunol., 25(5): 1391-8 (May 1995) (excerpt only, retrieved from http://www.ncbi.nlm.nih.gov/pubmed/...etc., on Sep. 15, 2009.

Magilavy et al., *Journal of Investigative Dermatology*, 110(4): 682 (Abstract 1260), (Apr. 1998).

Miller et al., Specific interaction of lymphocyte function-associate antigen 3 with CD2 can inhibit T cell responses, *Journal Exp. Medicine*, The Rockefeller University Press, 178: 211-222 (Jul. 1993).

Submission accompanying a Request for Continued Examination filed in related U.S. Appl. No. 11/398,908 on Sep. 15, 2009.

Submission accompanying a Request for Continued Examination filed in related U.S. Appl. No. 10/588,323 on Oct. 8, 2009.

Submission accompanying a Request for Continued Examination filed in related U.S. Appl. No. 11/398,908 on Jun. 9, 2010.

USPTO, Office Action in related U.S. Appl. No. 398,908 mailed Jan. 15, 2009.

USPTO, Office Action in related U.S. Appl. No. 11/578,391 mailed Feb. 4, 2009.

USPTO, Office Action in related U.S. Appl. No. 10/588,323 mailed Apr. 8, 2009.

USPTO, Office Action in related U.S. Appl. No. 11/398,908 mailed Dec. 10, 2009.

USPTO, Office Action in related U.S. Appl. No. 10/588,323 mailed Dec. 21, 2009.

* cited by examiner

METHOD FOR TREATING OR PREVENTING SCLEROTIC DISORDERS USING CD-2 BINDING AGENTS

RELATED APPLICATIONS

This application claims priority to U.S. Provisional application 60/307,688, filed Jul. 24, 2001, and U.S. Provisional application 60/382,459, filed May 22, 2002, both of which are incorporated herein by reference in their entirety, including drawings.

FIELD OF THE INVENTION

The invention relates to the treatment fibrotic disorders, e.g., sclerotic disorders.

BACKGROUND OF THE INVENTION

Fibrous proteins, which serve a structural role in organisms, have a rodlike conformation which can include regular α-helical, triple helical, or β-sheet/β-turn secondary structure. Fibrous proteins include collagen, keratin, myosin, tropomyosin and fibrinogen.

A number of disorders are characterized by inappropriate deposition of fibrous proteins. In addition to aberrant fibrous protein deposition, some fibrotic disorders, such as sclerotic disorders and, in particular, systemic sclerosis (scleroderma), show aberrant inflammatory and vascular activity. Systemic sclerosis is characterized by diffuse fibrosis of the skin, blood vessels, gastrointestinal tract, lungs, heart, and kidneys; and vascular abnormalities in the skin and articular structures (*The Merck Manual of Diagnosis and Therapy, Internet Edition*, Section 5, Chapter 50, Diffuse Connective Tissue Disease, Systemic Sclerosis, 2001). Patients suffer from skin thickening, pain, swelling, and stiffness of the fingers and knees, esophageal dysfunction, pulmonary hypertension, and renal failure. Thirty to 60% of scleroderma patients typically develop some restrictive lung disease within the first 3-5 years of disease (Steen V D et al. (1994) *Arthritis Rheum* 37: 1283; Black C M et al. (1996) In *Systemic Sclerosis*. Clements P J and Furst D E, eds. Williams & Williams, Baltimore, Md. pp. 299-332; Griedinger E L et al. (1998) *Chest* 114: 801). A subset of these patients, about 15-20% of all scleroderma patients, develops severe interstitial fibrosis (Steen V D et al. (1994) supra). Patients who do not have lung inflammation have lower risk for progressive lung fibrosis (Silver R M et al. (1990) *Am J Med* 88: 470; White B et al. (2000) *Annals Int Med* 132: 947). Lung inflammation occurs early in the course of scleroderma lung disease (Harrison N K et al. (1991) *Am Rev Respir Dis* 144: 706).

The etiology of systemic sclerosis is not well defined, but an activated immune system (especially T cells) and overproduction and accumulation of collagen and other extracellular matrix proteins are observed (See The Merck Manual, 2001 supra). T cells are believed to be important in the development of tissue damage in patients with systemic sclerosis. Activated T cells are present very early in the course of the disease and dominate the inflammatory infiltrates in tissues of patients with systemic sclerosis (White, B. (1996) *Scleroderma, Rheumatic Disease Clinics of North America*, Vol. 22 (4):695-708). When activated, T cells regulate functions of many hematopoietic and nonhematopoietic cells, including vascular cells and fibroblasts (White, B. (1996) supra).

Therapies for systemic sclerosis, and in particular for treating scleroderma interstitial lung disease, all have shortcomings. A number of small case series has suggested that therapy with cyclophosphamide may improve the outcome in scleroderma patients with lung inflammation, with stabilization of lung function and improved survival. However, cyclophosphamide has many significant side effects, including global bone marrow suppression which is accompanied by an increased risk of infection, hemorrhagic cystitis, and increased risk of malignancy. Many patients are hesitant to take cyclophosphamide therapy because of these risks. In addition, about 25% of patients with lung inflammation who receive cyclophosphamide do not respond significantly to the treatment, displaying continued decline in lung function (White, B. (2000) supra).

Other vital organs can be critically impaired by fibrosis and the associated inflammation. For example, hepatic fibrosis occurs as a response to hepatocellular necrosis or injury; collagen accumulation leads to hepatic cell atrophy and disruption of hepatic blood flow (Berkow, R. et al. (1992) *The Merck Manual of Diagnosis and Therapy, Internet Edition*, Section 6, Chapter 68, Fibrosis, Etiology, Pathogenesis).

Accordingly, there exists a need for improved modalities for preventing and treating conditions characterized by aberrant fibrosis such as systemic sclerosis, and in particular, conditions involving fibrosis of vital organs, e.g., lung or liver.

SUMMARY OF THE INVENTION

In general, the invention features a method of treating, or preventing a condition characterized by aberrant fibrosis, e.g., a fibrotic (e.g., a T cell fibrotic) or a sclerotic disorder (e.g., systemic sclerosis or scleroderma) in a subject. The invention also provides a method for treating, or preventing a T cell-mediated disorder chosen from sarcoidosis, ankylosis, and spondylitis-associated arthritis, e.g., ankylosing spondilitis, in a subject.

In some embodiments, methods are provided for preventing development, delaying onset, or inhibiting the development, of a disorder, e.g., a fibrotic, sclerotic or T cell disorder as described herein, in the subject. In other embodiments, methods are provided for attenuating the severity of, suppressing the deleterious effects of, or reversing, a disorder, e.g., a fibrotic, sclerotic or T cell disorder as described herein, in the subject. In yet other embodiments, methods are provided for preserving or restoring function of a visceral organ in the subject. In all embodiments, the subject for treatment is either afflicted with, or at risk of developing a disorder, e.g., a fibrotic, sclerotic or T cell disorder as described herein.

The methods of the present invention include administering to the subject a CD2-binding agent, an LFA-3-binding agent, or an inhibitor of the CD2:LFA-3 interaction, e.g., a CD2-binding agent or LFA-3 binding agent which inhibits the CD2:LFA-3 interaction (referred to collectively or individually as an "agent"), to thereby treat or prevent the disorder. Preferably, the agent is a soluble CD2-binding fragment of LFA-3. More preferably, the agent is a CD2-binding fragment of LFA-3 fused to all or part of an immunoglobulin hinge and heavy chain constant region or a portion thereof (e.g., an LFA-3/IgG fusion polypeptide).

In preferred embodiments, the subject is a mammal, e.g., a primate, preferably a higher primate, e.g., a human. In one embodiment, the subject is a patient having, or at risk of, a disorder, e.g., a fibrotic, sclerotic or T cell disorder as described herein.

As discussed above, the subject can be a patient having, or at risk of having, scleroderma, e.g., systemic scleroderma. The subject can be a patient at risk for, or having, fibrosis of the skin, or fibrosis of a visceral organ, e.g., lung, kidney, heart, liver, or gastrointestinal tract. The subject can be a patient who has or is at risk for a disorder characterized by aberrant intestinal fibrosis, e.g., intestinal lung disease (e.g., a lung fibrotic condition chosen from fibrosing alveolitis associated with systemic sclerosis (FASSc), or pulmonary hypertension caused by vascular disease of the lung). For example, the subject can have a mean alveolar wall thickness of less than about 20 microns, between about 20 to 40 microns, or greater than about 40 microns. In other embodiments, the subject has a bronchoalveolar lavage (BAL) cell differential count of at least (i.e., greater than or equal to) 3% neutrophils, or at least (i.e., greater than or equal to) 2.2% eosinophils. In yet other embodiments, the subject has one or more of: an elevated number of memory $CD8^+$ T cells in the BAL fluids from said subject, altered cytokine or chemokine gene expression in BAL cells, or abnormal T cell repertoire. In yet other embodiments, the subject has impaired vital organ function, e.g., decreased lung, kidney, liver function. For example, the subject has abnormal pulmonary function test (PFT) scores, including spirometry, lung volume and diffusion capacity for carbon monoxide. In other embodiments, the subject has an abnormal Raynaud's activity score. In other embodiments, the subject has abnormal skin as determined, e.g., based on modified Rodnan skin score.

The disorder can be characterized by one or more of: aberrant inflammatory, vascular, and/or fibrotic activities. For example, the sclerotic disorder can be chosen from systemic sclerosis or scleroderma (systemic or circumscribed scleroderma), mixed connective tissue disease (MCTD), or sclerodermatomyositis. In one embodiment, the disorder is circumscribed scleroderma, e.g., cutaneous scleroderma or CREST syndrome (Calcinosis, Raynaud's phenomenon, Esophageal dysfunction, Sclerodactyly, Telagiectasia). In other embodiments, the disorder is characterized by fibrosis of the skin, or fibrosis of a visceral organ, e.g., lung, kidney, liver, heart, gastrointestinal tract, or musculoskeletal system.

In a preferred embodiment, the disorder is a lung fibrosis having T cell involvement. For example, the disorder is characterized by aberrant interstitial fibrosis, e.g., interstitial lung disease, or granuloma formation. In one embodiment, the disorder is a lung condition chosen from one or more of: fibrosing alveolitis associated with systemic sclerosis (FASSc), pulmonary hypertension caused by vascular disease of the lung, cryptogenic fibrosing alveolitis, idiopathic pulmonary fibrosis, pulmonary fibrosis secondary to collagen vascular disease, pulmonary fibrosis associated with sarcoidosis, e.g., pulmonary granulomatosis, or pneumoconoses. In other embodiments, the disorder is an occupational lung disorder.

In other embodiments, the disorder is a fibrotic disorder other than scleroderma, e.g., morphea, keloids, hypertrophic scars, or connective tissue nevi of the collagen type; hepatic fibrosis, e.g., liver cirrhosis; kidney fibrosis; scar formation disorders; fibrotic conditions of the eye, e.g., diabetic retinopathy, postsurgical scarring (for example, after glaucoma filtering surgery), and proliferative vitreoretinopathy; cardiovascular fibrotic conditions, e.g., left ventricular hypertrophy secondary to hypertension; and fibrosis associated with myocardial infarction, myocarditis, or with ischemia-reperfusion injury to the heart.

In yet other embodiments, the disorder is a T cell-mediated disorder chosen from sarcoidosis, spondylitis-associated arthritis, e.g., ankylosing spondilitis and Reiter's syndrome, and ankylosis.

In preferred embodiments, the agent administered to the subject is a CD2-binding agent, e.g., an anti-CD2 antibody homolog; a soluble CD2-binding fragment of LFA-3; a CD2-binding fragment of LFA-3 coupled, e.g., fused, to another moiety, e.g., all or part of a plasma protein, all or part of an immunoglobulin (e.g., an IgG (e.g., an IgG1, IgG2, IgG3, IgG4), IgM, IgA (e.g., IgA1, IgA2), IgD, and IgE, but preferably an IgG) or a fragment thereof (e.g., an immunoglobulin constant region), serum albumin (e.g., human serum albumin), or a synthetic hydrophilic polymer such as PEG; a CD2-binding small molecule or peptidomimetic; a CD2-binding polypeptide fragment identified, e.g., by cell surface, e.g., phage display or using a peptide combinatorial library.

In one embodiment, the CD2-binding agent can be a soluble LFA-3 polypeptide, e.g., a polypeptides chosen from amino acids 1-92, 1-80, 50-65, 20-80 of the LFA-3 sequence shown in SEQ ID NO:3 of U.S. Pat. No. 6,162,432, which is hereby incorporated by reference.

Preferably, the CD2-binding agent is a CD2-binding fragment of LFA-3 fused to all or part of an immunoglobulin hinge and heavy chain constant region or a portion thereof (e.g., an LFA-3/IgG fusion polypeptide, e.g., an LFA-3/IgG fusion polypeptide having the nucleotide and amino acid sequence shown in SEQ ID NO:7 and 8 of U.S. Pat. No. 6,162,432, which is hereby incorporated by reference). In one embodiment, the soluble LFA-3 polypeptide is a fusion protein which includes the amino terminal 92 amino acids of mature LFA-3 and the C-terminal 10 amino acids of a human IgG1 hinge region. The soluble LFA-3 polypeptide can further include the CH2 and CH3 regions of a human IgG1 heavy chain constant domain. The CD2-binding moiety can be chosen from amino acids 1-92, 1-80, 50-65, 20-80 of the LFA-3 sequence shown in SEQ ID NO:3 of U.S. Pat. No. 6,162,432, which is hereby incorporated by reference.

In other embodiments, the CD2-binding agent is an anti-CD2 antibody homolog, e.g., a monoclonal anti-CD2 antibody (e.g., a recombinant (e.g. a chimeric or humanized anti-CD2 antibody) or an antigen binding fragment thereof (e.g., a Fab fragment, a Fab' fragment, a F(ab') 2 fragment, a F(v) fragment or an intact immunoglobulin heavy chain of an anti-CD2 antibody homolog).

In a preferred embodiment the CD2-binding agent is a chimeric, e.g., fusion, polypeptide which includes a first moiety that binds CD2, e.g., a CD2-binding moiety discussed herein, and a second moiety which recruits an immune effector cell, e.g., a macrophage, monocyte, neutrophil or dendritic cell. The first moiety can be a CD2-binding fragment of LFA-3, e.g., a fragment described herein, or an antibody homolog which binds CD2, e.g., an antibody homolog described herein. The second moiety can be a polypeptide capable of recruiting effector cells. In a preferred embodiment the second moiety includes: a fragment of an immunoglobulin constant region, e.g., an immunoglobulin fragment described herein; or an Fc receptor (e.g., FcγRI, FcγRII or Fcγ(RIII) binding antibody homolog.

In other embodiments, the agent administered to the subject is an LFA-3-binding agent, e.g., an anti-LFA-3 antibody homolog; a soluble LFA-3-binding fragment of CD2; an LFA-3-binding fragment of CD2 fused to another moiety, e.g., a plasma protein, an immunoglobulin (e.g., an IgG (e.g., an IgG1, IgG2, IgG3, IgG4), IgM, IgA (e.g., IgA1, IgA2), IgD, and IgE, preferably an IgG) or a fragment thereof (e.g., an immunoglobulin constant region), serum albumin (e.g., human serum albumin), or a synthetic hydrophilic polymer such as PEG; an LFA-3-binding small molecule or peptidomimetic; an LFA-3-binding polypeptide fragment identified, e.g., by cell surface, e.g., phage display or using a peptide combinatorial library. Preferably, the LFA-3- binding agent is an anti-LFA-3 antibody homolog, e.g., a monoclonal anti-LFA-3 antibody (e.g., a recombinant (e.g. a chimeric or humanized anti-LFA-3 antibody) or an antigen binding fragment thereof (e.g., a Fab fragment, a Fab' fragment, a F(ab')2 fragment, a F(v) fragment or an intact immunoglobulin heavy chain of an anti-LFA-3 antibody homolog).

The agent, e.g., an inhibitor of the CD2:LFA-3 interaction, can be administered systemically or parenterally (e.g., intravenously, intramuscularly, subcutaneously, transdermally, or by inhalation). For example, the agent can be administered by injection or needleless injection. In other embodiments, the agent is administered locally (e.g., topically) to an area afflicted by the disorder, e.g., the fibrotic or sclerotic disorder. Preferably, the agent is administered in an amount effective to have the desired therapeutic or prophylactic effect. For prophylactic embodiments, the agent can be administered in an amount effective to prevent the development, delay the onset, or inhibit the development, of the disorder, e.g., the fibrotic, sclerotic or T cell disorder as described herein. For therapeutic embodiments, the agent can be administered in an amount effective to inhibit fibrosis or inflammation, attenuate the severity of, suppress the deleterious effects of, or reverse, the disorder, e.g., the fibrotic, sclerotic or T cell disorder as described herein. In other embodiments, the agent can be administered in an amount effective to preserve or restore function of a visceral organ.

For example, the agent, e.g., an LFA-3/IgG fusion polypeptide, can be administered at a dosage ranging from about 0.001 to about 50 mg binding agent per kg body weight. In one embodiment, the agent, e.g., the LFA-3/IgG fusion polypeptide, is administered systemically. The agent, e.g., the LFA-3/IgG fusion polypeptide, can be administered to a subject, e.g., a subject as described herein can be administered periodically, e.g., once a week during a therapeutic treatment period of twelve weeks. In one embodiment, the agent, e.g., the LFA-3/IgG fusion polypeptide, is administered at a dosage ranging from 5 to 10 mg IV bolus (for example, 7.5 mg IV bolus) at least once during the therapeutic treatment period. In other embodiments, the agent is administered monthly, weekly, biweekly, or daily, as deemed appropriate by the treating physician.

Treatment or prophylaxis of the disorders, e.g., the fibrotic, sclerotic or T cell disorders described herein, can include combination of the CD2- or LFA-3 binding agent with a second agent, e.g., a T cell inhibitor. Thus, in a preferred embodiment, the method further includes: administering to the subject, e.g., a subject as described herein, one or more of: a cytokine binding agent (e.g., a type 2 cytokine inhibitor); a costimulatory molecule binding agent, e.g., a B7 binding agent (e.g., a B7-1 binding agent, e.g., an anti-B7-1 antibody); an ICAM or LFA-1 (CD11a) binding agent, e.g., an inhibitor of an ICAM/LFA-1 interaction (e.g., a monoclonal antibody against ICAM-1 or CD11a, e.g., a humanized, chimeric, or human anti-ICAM-1 or anti-CD11a antibody); a vasodilator (e.g., an ACE inhibitor or minoxidil); an immunosuppressant (e.g., methotrexate, cyclosphorin, or chlorambucil); cyclophosphamide; a corticosteroid, e.g., prednisone; or penicillamine. In one embodiment, the CD2- or LFA-3 binding agent is administered in combination with one or more inhibitors of interleukin-1 (IL-1), IL-2, IL-4, IL-6, IL-8, TNF-.alpha., TGF-.beta., PDGF, granzyme A or leukotriene B4. In one embodiment, the second agent is an IL-2 binding agent, e.g., an antibody (e.g., a monoclonal) antibody against IL-2.

The agent, e.g., an inhibitor of the CD2:LFA-3 interaction, and a second agent can be administered simultaneously, or sequentially, e.g., administering the inhibitor first followed by the other agent, or vice versa. Preferably, the agent and the second agent are administered in sufficiently close proximity, e.g., spatially or temporally, such that the desired effect, e.g., the reduction in the cytokine or inflammation marker levels, or the reduction in a symptom, is greater than what would be observed with the agent administered without the second agent, or the second agent administered without the agent. The agent and the second agent can be administered before treatment, concurrently with treatment, posttreatment, or during remission of the disease.

In a preferred embodiment, the method further includes the step of identifying a subject at risk for, or having a fibrotic or a sclerotic disorder, e.g., a disorder described herein, prior to administering the agent, e.g., an inhibitor of the CD2:LFA-3 interaction. The level of inflammatory activity in the subject prior to, during, or after, administration of the agent can be evaluated. A change in the level of a marker for inflammation relative to a control is indicative of a change in the level of inflammatory activity. Candidate subjects for treatments can have, prior to treatment, at least one marker for inflammation that is elevated relative to the level of the same inflammatory marker in a control subject.

In other embodiments, the method further includes the step of monitoring the subject, e.g., for symptoms, or for changes in the level of inflammatory activity, e.g., cytokine or inflammatory marker levels, e.g., IL-1, IL-2, IL-4, IL-6, IL-8, TNF-$\alpha$, TGF-$\beta$, PDGF, granzyme A or leukotriene B4, or in an immune cell population (e.g., T cells, e.g., memory effector T lymphocytes (e.g., CD8+ cells, e.g., CD8/CD45 RO+ cells)). Generally, a decrease in cytokine levels, or in the selected immune cell population, is indicative of the improved condition of the subject. For example, the subject can exhibit a depletion of $CD3^+$, $CD4^+$, and $CD8^+$ T cells, e.g., in both peripheral blood and BAL fluids, in response to treatment.

The subject can be monitored prior to beginning of treatment, during the treatment, or after one or more elements of the treatment have been administered. Monitoring can be used to evaluate the need for further treatment with the same agents or for additional treatment with additional, e.g., second agents. For example, the level of inflammatory activity in the subject can be monitored by one or more of: detecting the number of activated CD8-positive T cells in BAL fluid; detecting the number of memory and activated CD4-positive T cells in BAL fluids; assessing the change in the percentage of neutrophils and eosinophils; assessing the BAL cell differential; detecting chemokine gene expression; detecting cytokine gene expression; detecting T cell repertoire; detecting forced vital capacity (FVC) and diffusing capacity for carbon monoxide (DLco); detecting patient and physician global assessments; measuring dyspnea score; measuring skin score; measuring scleroderma disease severity score; measuring organ-specific score; measuring Raynaud's activity score; or detecting mean alveolar wall thickness of the subject. In one embodiment, candidate subjects for treatment typically have, prior to treatment, an elevated level or number (e.g., about a two- or three-fold elevation) of memory CD8+ cells in BAL fluids, as compared to the level or number of memory CD8+ cells in the BAL fluids of a control subject.

The methods of the invention can further include the step of analyzing a nucleic acid or protein from the subject, e.g., analyzing the genotype of the subject. The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the CD2 binding agent to thereby determine appropriate dosage(s) and treatment regimen(s) of the CD2 binding agent (e.g., amount per treatment or frequency of treatments) for prophylactic or therapeutic treatment of the subject.

In another aspect, the invention features a method of monitoring the efficacy of a treatment for a sclerotic or fibrotic disorder, e.g., a sclerotic or fibrotic disorder as described herein, in a subject, e.g., a subject as described herein. The method includes:

administering to the subject a CD2-binding agent, an LFA-3-binding agent, or an inhibitor of the CD2:LFA-3 interaction, e.g., a CD2-binding agent or LFA-3-binding agent which inhibits the CD2:LFA-3 interaction; and evaluating the level of inflammatory activity in the subject. A change in the level of inflammatory activity in the subject relative to a control, e.g., the subject prior to treatment, is indicative of the efficacy of the treatment. For example, a reduction in the level of inflammatory activity after treatment is indicative of the efficacy of the treatment.

The level of inflammatory activity in the subject can be evaluated prior to, during, or after, administration of the agent, e.g., by measuring one or more of the parameters described herein.

Preferably, the method further includes adjusting the amount of the agent administered to the subject until a decrease is observed in the level of inflammatory activity. Such adjustment can be accomplished by altering the dose of agent per treatment, or by altering the frequency of dosing, or both.

In another aspect, the invention features a composition, e.g., a pharmaceutical composition, comprising a CD2-binding agent, an LFA-3 binding agent, or an inhibitor of the CD2:LFA-3 interaction, e.g., a CD2-binding agent or LFA-3 binding agent which inhibits the CD2:LFA-3 interaction, in combination with one or more of: a second agent, e.g., T cell inhibitor. For example, the second agent can be a cytokine binding agent (e.g., a type 2 cytokine inhibitor); a costimulatory molecule binding agent, e.g., a B7 binding agent (e.g., a B7-1 binding agent, e.g., an anti-B7-1 antibody); an ICAM or LFA-1 (CD11a) binding agent, e.g., an inhibitor of an ICAM/LFA-1 interaction (e.g., a monoclonal antibody against ICAM-1 or CD11a, e.g., a humanized, chimeric, or human anti-ICAM-1 or anti-CD11a antibody); a vasolidator (e.g., an ACE inhibitor or minoxidil); an immunosuppressant (e.g., methotrexate, cyclosphorin, or chlorambucil); cyclophosphamide; a corticosteroid, e.g., prednisone; or penicillamine. In one embodiment, the CD2- or LFA-3 binding agent is administered in combination with one or more inhibitors of interleukin-1 (IL-1), IL-2, IL-4, IL-6, IL-8, TNF-α, TGF-β, PDGF, granzyme A or leukotriene B4. In one embodiment, the second agent is an IL-2 binding agent, e.g., an antibody (e.g., a monoclonal) antibody against IL-2.

Preferably, the composition, e.g., the pharmaceutical composition, is dispersed in a pharmaceutically acceptable carrier. Preferably, the composition is suitable for intravenous, intramuscular, subcutaneous, transdermal, or inhalant administration. In one embodiment, the composition includes the agent, e.g., the LFA-3/IgG fusion polypeptide, in combination with a pharmaceutically acceptable carrier comprising citrate, glycine and sucrose (e.g., at least about 1 to 5% sucrose, 0.5% to 2% glycine in sodium citrate-citric buffer). In one embodiment, the agent, e.g., the LFA-3/IgG fusion polypeptide, can be administered as a 5 to 10 mg IV bolus (for example, 7.5 mg IV bolus).

In another aspect, the invention features a kit which includes one or more of: (i) a CD2-binding agent, an LFA-3-binding agent, or an inhibitor of the CD2:LFA-3 interaction, e.g., a CD2-binding agent or LFA-3 binding agent which inhibits the CD2:LFA-3 interaction, e.g., an agent described herein; (ii) a second agent, e.g., a second agent as described herein; and (iii) instructions on how to use the agent to treat a disorder described herein.

In a preferred embodiment, the CD2-binding agent is an LFA-3/Ig fusion polypeptide. Preferably, the LFA-3/Ig fusion polypeptide is lyophilized.

Other features and advantages of the instant invention will become more apparent from the following detailed description and claims.

DETAILED DESCRIPTION OF THE INVENTION

Scleroderma is one of the most deadly fibrotic-systemic autoimmune diseases (Williams H J et al. (1998) *J Rheumatol* 25: 261). The majority of the deaths are caused by severe interstitial lung disease or pulmonary hypertension (Hesselstrand R. et al. (1998) *Ann Rheum Dis.* 57: 682; Altman R. D. et al. (1991) *Arthritis Rheum* 34: 403). Thirty to 60% of scleroderma patients typically develop some restrictive lung disease (FVC<80% predicted) within the first 3-5 years of disease (Steen V. D. et al. (1994) supra; Black C. M. et al. (1996) supra; Griedinger E L et al. (1998) supra). About 43% of patients with the disease less than 3 years duration have this problem (Griedinger E L et al. (1998) supra). A subset of these patients develops severe interstitial fibrosis, perhaps about 15-20% of all scleroderma patients (Steen V. D. et al. (1994) supra). The presence of lung inflammation on bronchoalveolar lavage (BAL) cell differential count (neutrophilia >3% and/or eosinophilia >2.2%) identifies a subset of patients at greater risk for developing progressive lung fibrosis (Silver R. M. et al. (1990) supra; White B. et al. (2000) supra). Patients who do not have lung inflammation have lower risk for progressive lung fibrosis. Lung inflammation occurs early in the course of scleroderma lung disease (Harrison N. K. et al. (1991) supra). The earliest changes on biopsy include patchy lymphocyte infiltration of the alveolar wall (Harrison N. K. et al. (1991) supra).

$CD8^+T$ cells are typically increased in number and abnormally activated in the lungs of scleroderma patients who are at greater risk for progressive lung fibrosis. For example, bronchoalveolar lavage (BAL) fluids from scleroderma patients, especially in patients with lung inflammation, show an increase of about 3.5 fold in total number of $CD8^+T$ cells and two-fold in percent, compared to controls. The percentage of BAL $CD8^+T$ cells negatively correlates with pulmonary function tests (PFTs) such as forced vital capacity (FVC) and diffusing capacity for carbon monoxide (DLco) (% predicted). Scleroderma patients, especially patients with lung inflammation, show more recently activated $CD8^+T$ cells, with about a seven-fold increase in total numbers of $HLA-DR^+$ and about a four-fold increase in $IL-2R^+$ cells. The numbers and percentages of $CD8DR^+$ and $CD8^+IL-2R^+$ cells negatively correlate with pulmonary function. Scleroderma patients also have more oligoclonal T cell antigen receptors, a pattern that persists over time, and make type 2 cytokines, unlike most controls whose $CD8^+T$ cells make type 1 cytokines. The production of type 2 cytokines in the lungs is associated with greater decline in FVC over time.

CD8+T cells are activated in vivo in the lungs of scleroderma patients. In BAL fluids, levels of soluble Fas ligand, granzyme A and granzyme B are all elevated, especially in patients with lung inflammation, compared to controls. Higher levels of granzyme B were associated with lower FVC and DLco at the time of BAL and with greater decline in FVC and DLco over time.

Human CD2 is a glycoprotein that is expressed on all subsets of T lymphocytes and natural killer (NK) cells (Brottier, P. et al. (1995) *J. Immunol.* 135:1624). CD2 increases cellular adhesion between cognate partners and augments T lymphocyte responses initiated through the T cell receptor (TCR/CD3) complex (Meuer, S. C. et al. (1984) *Cell* 36:897; Alcover, A. et al. (1988) *EMBO J* 7:1973). Interaction of human CD2 with its primary natural ligand, LFA-3, costimulates T lymphocyte proliferation and cytotoxic T lymphocyte (CTL) and NK effector functions. Early T lymphocyte activation events stimulated via CD2 include signal transduction events such as phosphoinositol turnover, intracellular calcium mobilization, and subsequent tyrosine kinase phosphorylation of intracellular proteins (Ley, S. C. et al. (1991) *Eur J Immunol* 21:2203; Brottier, P. et al. (1995) supra).

LFA-3 is a heavily glycosylated protein that is expressed on a large variety of human cells both as a transmembrane-integral protein and as a surface protein (Dustin, M. L. et al. (1987) *Nature* 329:846. LFA-3 is known to act as a human CD2 ligand, enhancing adhesiveness of T lymphocytes to antigen-presenting cells. Additionally, there is evidence that CD2/LFA-3 interactions transduce signals not only to T lymphocytes, with subsequent increase in pp56$^{lck}$ tyrosine kinase activity (Danielian, S. et al. (1991) *Eur J Immunol* 21:1967; Schraven, B. et al. (1993) Eur J Immunol 23:119-123), but also to interacting monocytes resulting in secretion of cytokines involved in T lymphocyte responses (Webb, D S et al. (1990) *Science* 249:1295.

The LFA-3/CD2 interaction pathway plays a significant role in mammalian T lymphocyte function. Many fibrotic-chronic autoimmune diseases, e.g., scleroderma, are characterized by increased numbers of T lymphocytes (and in particular, pathogenic T lymphocytes such as CD45RO memory effector cells), as well as increased T lymphocyte activation. Accordingly, therapy that reduces T lymphocyte number and/or activation may improve the management of these disorders. CD2-binding agents, e.g., LFA-3/IgG$_1$ fusion proteins, block the LFA-3/CD2 interaction both in vitro and in vivo resulting in interference with T lymphocyte number and activation (especially pathogenic T lymphocytes), and subsequent modification of the inflammatory process. Therefore, such inhibitors are useful in the treatment or prevention of fibrotic (e.g., sclerotic) disorders, as well as other T cell-mediated disorders. Accordingly, the present invention provides methods and compositions for treating, or preventing, a condition characterized by aberrant fibrosis or immune activity, e.g., a fibrotic or sclerotic disorder (e.g., systemic sclerosis or scleroderma), or a T cell-mediated disorder chosen from sarcoidosis, ankylosis, and spondylitis-associated arthritis, e.g., ankylosing spondilitis, in a subject at risk of or afflicted with such disorders.

In order that the present invention may be more readily understood, certain terms are first defined. Additional definitions are set forth throughout the detailed description.

Fibrosis is the formation of fibrous tissue, usually as a reparative or a reactive process. As used herein, "fibrosis" does not refer to the formation of fibrous tissue that is a normal part of an organ or tissue, but includes those disorders or disease states that are caused by or accompanied by the abnormal deposition of fibrotic tissue. Fibrosis can follow surgery in the form of adhesions, keloid tumors or hypertrophic (very severe) scarring. Fibrosis causes contractures and joint dislocation following severe burns, wounds or orthopedic injuries; it can occur in any organ and accompanies many disease states, such as systemic sclerosis or scleroderma (fibrotic skin and internal organs), hepatitis (liver cirrhosis), hypertension (heart failure), tuberculosis (pulmonary fibrosis), diabetes (nephropathy) and atherosclerosis (fibrotic blood vessels). Fibrosis also includes all arteriosclerotic disorders, pulmonary fibrosis, adult respiratory distress syndrome, inflammatory disorders including autoimmune disorders, such as sclerodermas, cirrhosis, keloids, adhesions and hypertrophic scars.

Sclerosis refers to an induration or hardening of tissues of chronic inflammatory origin. As used herein, the term "systemic sclerosis" or "scleroderma" refers to a disease or disorder, typically chronic, which are characterized by one or more of: diffuse fibrosis; degenerative abnormalities; and/or vascular abnormalities in the skin (scleroderma), articular structures, or internal organs (e.g., the lungs, heart, kidneys, esophagus, and GI tract). The term includes all forms of the disease, including but not limited to: localized or circumscribed forms of the disease characterized by circumscribed patches (morphea) or linear sclerosis of the integument and immediately subjacent tissues without systemic involvement; forms distinguished by restricted skin involvement (often just the fingers and the face) and slow progression (this form is termed limited cutaneous scleroderma or CREST syndrome (Calcinosis, Raynaud's phenomenon, Esophageal dysfunction, Sclerodactyly, Telangiectasia); as well as systemic forms of scleroderma ranging from generalized cutaneous thickening (systemic sclerosis with diffuse scleroderma), which may cause rapidly progressive and often fatal visceral involvement. Although the terms "fibrosis" and "sclerosis" are often used interchangeably herein, the term "sclerosis" refers preferably to a subset of fibrotic conditions, which are typically chronic.

Fibrosis of the cardiorespiratory system refers to fibrosis of the lungs and/or the heart. Lung fibrosis typically causes early impairment in gas exchange leading to exertional dyspnea. Pleurisy and pericarditis with effusion may occur. Lung involvement typically progresses indolently, with substantial individual variability. Pulmonary hypertension may result from long-standing interstitial and peribronchial fibrosis or intimal hyperplasia of small pulmonary arteries. Impairments in lung function can be detected by examining T cell population in the bronchoalveolar lavage (BAL) fluids from sclerodema patients, especially in patients with lung inflammation, e.g., by detecting the number and degree of activation of CD8$^+$T cells, compared to controls as described herein. The percentage of BAL CD8$^+$T cells negatively correlates with pulmonary function tests (PFTs) such as forced vital capacity (FVC) and diffusing capacity for carbon monoxide (DLco) (% predicted). Lung disorders characterized by aberrant interstitial fibrosis (e.g., a lung fibrotic condition chosen from one or more of: fibrosing alveolitis associated with systemic sclerosis (FASSc), pulmonary hypertension caused by vascular disease of the lung, cryptogenic fibrosing alveolitis, idiopathic pulmonary fibrosis, pulmonary fibrosis secondary to collagen vascular diseases) are encompassed by the phrase "fibrosis of the lung." Cardiac arrhythmias, conduction disturbances, and other ECG abnormalities are common. Heart failure may develop because of pulmonary impairment or because of diffuse fibrous replacement of cardiac muscle. Heart failure tends to be chronic and difficult to treat.

The phrases "fibrosis of the skin," or "fibrosis of a visceral organ, e.g., lung, kidney, heart, liver, or gastrointestinal tract" are intended to have their clinical meanings. For example, "fibrosis of the skin" refers to induration of the skin which is typically symmetric and may be confined to the fingers (sclerodactyly) and distal portions of the upper extremities, or it may affect most or all of the body. Upon progression of the disease, the skin becomes taut, shiny, and hyperpigmented; the face becomes masklike; and telangiectases appear on the fingers, chest, face, lips, and tongue. Subcutaneous calcifications may develop (calcinosis circumscripta), usually on the fingertips (pulps) and over bony eminences. Alterations in the vasculature are seen by dilated capillary loops mixed with areas of loss of the microvascular loops normally visible at that site. An increase in compact collagen fibers in the reticular dermis, epidermal thinning, loss of rete pegs, and atrophy of dermal appendages may also be seen. There may be variably large accumulations of T lymphocytes in the dermis and subcutis, which also may be the site of extensive fibrosis.

The phrase "fibrosis of the GI tract" refers to the esophageal dysfunction frequently associated with visceral disturbance and eventually occurs in most patients. Dysphagia (manifested by various abnormal swallowing sensations) is initially caused by impaired esophageal motility but later can result from gastroesophageal reflux disease and secondary stricture formation. Acid reflux resulting from lower esophageal sphincter incompetence, and peptic esophagitis with possible ulceration and stricture are common. Barrett's esophagus occurs in ⅓ of patients with scleroderma; these patients have an increased risk of complications (e.g., stricture, adenocarcinoma). Hypomotility of the small intestine may be associated with malabsorption resulting from anaerobic bacterial overgrowth. Pneumatosis cystoides intestinalis may follow degeneration of the muscularis mucosa and entry of air into the submucosa of the intestinal wall. Characteristic large-mouthed sacculations can develop in the colon and ileum because of atrophy of the smooth muscle of these segments. This phrase also includes liver complications associated with biliary cirrhosis.

The phrase "fibrosis of the renal system or the kidney" refers to the renal disease (often severe) that may occur as a consequence of intimal hyperplasia of interlobular and arcuate arteries and usually is heralded by the abrupt onset of accelerated or malignant hypertension.

The phrase "fibrosis of musculoskeletal system" refers to the symptoms that may develop over the joints (particularly the knees), tendon sheaths (tendinitis), and large bursae because of fibrin deposition on synovial surfaces. Flexion contractures of the fingers, wrists, and elbows result from fibrosis of the synovial membrane, periarticular soft tissues, and skin. Trophic ulcers are common, especially on the fingertips, overlying the finger joints, or over calcinotic nodules.

The phrase "fibrotic disorder" or "sclerotic disorder" means diseases, conditions or other abnormal medical states which typically result in fibrosis or sclerosis, respectively, and generally are also characterized by inflammation or abnormal T-cell activation. As used herein, the term "sclerotic disorder" refers to fibrotic disorders which show one or more features of scleroderma or systemic sclerosis described above. Examples of sclerotic disorders include but are not limited to systemic sclerosis or scleroderma (systemic or circumscribed scleroderma), mixed connective tissue disease (MCTD), or sclerodermatomyositis.

As used herein, the term "sarcoidosis" refers to a typically multisystem granulomatous disorder characterized by non-caseating epithelioid granulomas involving various organs or tissues, with symptoms dependent on the site and degree of involvement. Fever, weight loss, and arthralgias may occur initially. Persistent fever is common with liver involvement. Peripheral lymphadenopathy is common and usually asymptomatic; even insignificant nodes may contain granulomas. Organ function may be impaired by the active granulomatous disease or by secondary fibrosis. Subjects with chronic sarcoidosis can also have skin lesions (plaques, papules, subcutaneous nodules), as well as nasal and conjunctival mucosal granulomas. Other symptoms and pathology associated with the disease include erythema nodosum, often with fever and arthralgias; hepatic granulomas; hepatomegaly; granulomatous uveitis; severe vision loss due to retinal involvement, severe vitreitis, or secondary glaucoma; lacrimal gland enlargement, conjunctival and eyelid infiltrations, and keratitis sicca occasionally; myocardial involvement, which may result in angina, heart failure, or fatal conduction abnormalities; acute polyarthritis; chronic periarticular swelling and tenderness; acute periarticular ankle inflammation; CNS and lung complications (e.g., pulmonary fibrosis). A more detailed description of the disorder pathology, symptoms and therapeutic modalities is provided in *The Merck Manual of Diagnosis and Therapy,* 17th Edition, section 21, chapter 288, the contents of which are expressly incorporated by reference.

As used herein, the term "spondylitis-associated arthritis" refers to a subgroup of inflammatory conditions that includes ankylosing spondilitis and Reiter's syndrome.

As used herein, the term "ankylosing spondilitis" refers to a systemic rheumatoid disorder characterized by inflammation of the axial skeleton and large peripheral joints. A more detailed description of the disorder pathology, symptoms and therapeutic modalities is provided in *The Merck Manual of Diagnosis and Therapy,* $17^{th}$ Edition, section 5, chapter 51, the contents of which are expressly incorporated by reference.

As used herein, the term "Reiter's syndrome" refers to an arthritic conditions that frequently develops after genitourinary infection or gastroenteritis. A more detailed description of the disorder pathology, symptoms and therapeutic modalities is provided in *The Merck Manual of Diagnosis and Therapy,* $17^{th}$ Edition, section 5, chapter 51, the contents of which are expressly incorporated by reference.

As used herein, the term "ankylosis" refers to a condition involving immobility or fusion of the joints, e.g., TMJ. Ankylosis of the TMJ most often results from trauma or infection, although it may accompany RA or be congenital. Chronic, painless limitation of movement occurs. When ankylosis leads to arrest of condylar growth, facial asymmetry is usual. Intra-articular (true) ankylosis must be distinguished from extra-articular (false) ankylosis, which may be caused by enlargement of the coronoid process, depressed fracture of the zygomatic arch, or scarring from surgery, irradiation, or infection. In most cases of true ankylosis, x-rays of the TMJ show loss of normal bony architecture. A more detailed description of the disorder pathology, symptoms and therapeutic modalities is provided in *The Merck Manual of Diagnosis and Therapy,* $17^{th}$ Edition, section 9, chapter 108, the contents of which are expressly incorporated by reference.

As used herein, "treating or preventing" a disorder, e.g., a fibrotic, sclerotic or T cell-mediated disorder, "in a subject afflicted with or at risk of developing" such disorder means one or more of the following: preventing development, delaying onset, or inhibiting the development, of a disorder, in a subject at risk of the disorder, or attenuating the severity of, suppressing the deleterious effects of, or reversing, a sclerotic disorder in a subject afflicted with the disorder; or preserving or restoring function of a visceral organ in a subject afflicted with a sclerotic disorder. The treatment or prevention of the disorder does not necessarily indicate a total elimination of the disorder's symptom(s).

The phrase "afflicted with" such a disorder means that the subject exhibits at least one symptom of a disorder disclosed herein. In some embodiments the subject is likely to develop significant pathological fibrosis or sclerosis in the course of events, even though signs of fibrosis or sclerosis may not be evident at the time of diagnosis. The diagnosis of individuals who suffer from disorders that typically result in debilitating fibrosis or sclerosis may be readily made by those having ordinary skill in the art using well-established criteria and methods.

The phrase "at risk of" such a disorder means that the subject has a possibility of developing a disorder as described above, e.g., a fibrotic, sclerotic or T cell-mediated disorder, at some point during the subject's life. In particular, the subject has a known risk factor, e.g., a risk factor of genetic, congenital, environmental, acquired, or occupational origin, for developing the disorder. The phrase also includes risks for disease progression from localized or circumscribed forms of the disease to forms of the disorder involving visceral involvement. For example, the presence of lung inflammation on bronchoalveolar lavage (BAL) cell differential (e.g., neutrophilia >3% and/or eosinophilia >2.2%) identifies a subset of patients at greater risk for developing progressive lung fibrosis.

As used herein, "preventing development" of a disorder, e.g., a fibrotic, sclerotic or T cell-mediated disorder, "in a subject at risk of the disorder" means that at least one symptom of the disorder, (e.g., a sclerotic disorder), remains absent in the subject through the applicable period of clinical treatment and/or monitoring. In one embodiment, the subject is free of a symptom for a therapeutic treatment period of at least twelve weeks. Preferably, the subject remains free of symptoms for at least a period of six months, more preferably, at least twelve months following the therapeutic treatment period.

As used herein, "delaying onset of" a disorder, e.g., a fibrotic, sclerotic or T cell-mediated disorder, "in a subject at risk of the disorder" means that at least one symptom of the disorder, while eventually present in the subject, is delayed in its appearance, e.g., it remains absent in the subject for a medically significant period of time beyond that at which the symptom would be expected to arise during the natural history of the disorder in the absent of treatment.

A "medically significant period of time" thus depends on the nature of the disorder. For example, a delay in the onset of restrictive lung disease for more than 3-5 years beyond diagnosis would be medically significant.

As used herein, "inhibiting development" of a disorder, e.g., a fibrotic, sclerotic or T cell-mediated disorder, "in a subject afflicted with or at risk of the disorder" means that at least one symptom indicating disease progression remains absent in the subject over a therapeutic treatment period of twelve weeks. Preferably, the subject remains free of symptoms of disease progression for at least a period of six months, more preferably at least twelve months following the therapeutic treatment period.

As used herein, "attenuating the severity of" a disorder, e.g., a fibrotic, sclerotic or T cell-mediated disorder, "in a subject afflicted with or at risk of the disorder" means that at least one symptom of the sclerotic disorder is attenuated or reduced, compared to what would be present in the absence of treatment (i.e., in the natural history of the untreated disorder). "Attenuate" refers to situations in which a symptom is reduced but not necessarily entirely eliminated.

As used herein, "suppressing the deleterious effects of" a disorder, e.g., a fibrotic, sclerotic or T cell-mediated disorder, "in a subject afflicted with or at risk of the disorder" means that a deleterious or negative effect associated with such disorder is decreased as compared to that in an untreated subject. In other words, a palliative effect is obtained.

As used herein, "reversing" a disorder, e.g., a fibrotic, sclerotic or T cell-mediated disorder, "in a subject afflicted with the disorder" means that a symptom or deleterious effect associated with a such disorder is reduced or the patient's condition is changed so as to restore the subject to a clinical status equivalent to an earlier stage of the disorder, optionally, up to and including a status equivalent to a subclinical stage of the disorder at which the subject is able to resume normal activities.

The term "symptom(s)" as used herein refers to a clinical manifestation of a disorder, e.g., a fibrotic, sclerotic or T cell-mediated disorder, in a subject. Examples of such symptoms include abnormal fibrosis in response to injury or tissue damage, or in response to a disorder as described herein. In the case of scleroderma, examples of such symptoms include one or more of diffuse fibrosis, accumulation of fibrotic tissue, increased in the number or activity of T cells (e.g., CD8+ T cells), degenerative abnormalities, and/or abnormalities in the skin (scleroderma), articular structures, or internal organs (e.g., lungs, heart, kidneys, esophagus, and GI tract. In the case of ankylosing spondylitis, such symptoms can include a reduction in back and joint pain. In the case of sarcoidosis, the symptoms can include a reduction in granuloma formation, e.g., decreased multiple noncaseating epitheloid granulomas in, e.g., the lymph nodes, lungs, liver, eyes, skin, CNS, spleen, bones, among other organs.

The term "deleterious effects" as used herein includes the physical consequences of the symptoms, which may result in discomfort, pain, or endanger the life of the subject. Examples of such deleterious effects include accumulation of fibrotic tissue in response to injury or tissue damage, or in response to a disorder (e.g., a sclerotic disorder) as described herein. In the case of scleroderma, examples of such deleterious effects include one or more of accumulation of fibrotic tissue, increased in the number or activity of T cells (e.g., $CD8^+$ T cells), degenerative abnormalities; and/or vascular abnormalities in the skin (scleroderma), articular structures, or internal organs (e.g., the lungs, heart, kidneys, esophagus, and GI tract).

As used herein, "preserving function of a visceral organ in a subject afflicted with or at risk of developing a disorder, e.g., a sclerotic disorder," means that at least one parameter correlated with function of the visceral organ remains stable relative to the expected decline of function of the organ in the untreated natural history of the disorder. E.g., in the case of the lungs, the BAL fluids from sclerodema patients show a decrease in an inflammatory marker, e.g., $CD8^+T$ cells, HLA-$DR^+$, IL-$2R^+$ cells, compared to the subject prior to treatment. Alternatively, an improvement in pulmonary function tests (PFTs) such as forced vital capacity (FVC) and diffusing capacity for carbon monoxide (DLco) (% predicted) can also be measured.

As used herein, "restoring function of a visceral organ in a subject afflicted with" a disorder, e.g., a sclerotic disorder, means that at least one parameter correlated with function of the visceral organ is improved relative to the level of function of the organ at the same stage of the untreated natural history of the disorder. E.g., where a desired function is reduced or lost at the onset of treatment that function is increased in a medically significant way after treatment is begun up to and including an increase to a function level equivalent to that seen at a subclinical stage of the disorder, where impaired organ function does not adversely affect the subject's normal activities. E.g., in the case of the lungs, the BAL fluids from sclerodema patients show a decrease in an inflammatory marker, e.g., $CD8^+T$ cells, HLA-$DR^+$, IL-$2R^+$ cells, compared to the subject prior to treatment. Alternatively, an improvement in pulmonary function tests (PFT's) such as forced vital capacity (FVC) and diffusing capacity for carbon monoxide (DLco) (% predicted) can also be measured.

As used herein, "CD2" means a CD2 polypeptide that interacts with (e.g., binds to) the extracellular portion of a naturally occurring LFA-3 polypeptide and which is homologous (e.g., at least about 85%, 95%, 96% or 100% homology) to an amino acid sequence as shown in SEQ ID NO:5 of U.S. Pat. No. 6,162,432, which is hereby incorporated by reference; or which is encoded by (a) a naturally occurring mammalian CD2 nucleic acid sequence (e.g., SEQ ID NO:5 of U.S. Pat. No. 6,162,432, which is hereby incorporated by reference); (b) a nucleic acid sequence degenerate to a naturally occurring CD2 nucleic acid sequence; (c) a nucleic acid sequence at least 85% homologous to the naturally occurring mammalian CD2 nucleic acid sequence (e.g., SEQ ID NO:5 of U.S. Pat. No. 6,162,432, which is hereby incorporated by reference); or (d) a nucleic acid sequence that hybridizes to one of the foregoing nucleic acid sequences under conditions equivalent to about 20° C. to 27° C. below $T_m$ and 1 M sodium chloride, e.g., a nucleic acid sequence that hybridizes to one of the foregoing nucleic acid sequences under stringent conditions, e.g., highly stringent conditions.

As used herein, "LFA-3" means an LFA-3 polypeptide that binds to the extracellular portion of a naturally occurring CD2 polypeptide and which has or is homologous (e.g., at least about 85%, 95%, 96% or 100% homology) to an amino acid sequence as shown in SEQ ID NO:1 or 3 of U.S. Pat. No. 6,162,432; or which is encoded by (a) a naturally occurring mammalian LFA-3 nucleic acid sequence (e.g., SEQ ID NO:1 or SEQ ID NO:3 of U.S. Pat. No. 6,162,432, which is hereby incorporated by reference); (b) a nucleic acid sequence degenerate to a naturally occurring LFA-3 nucleic acid sequence; (c) a nucleic acid sequence at least 85% homologous to the naturally occurring mammalian LFA-3 nucleic acid sequence (e.g., SEQ ID NO:1 or SEQ ID NO:3 of U.S. Pat. No. 6,162,432, which is hereby incorporated by reference); or (d) a nucleic acid sequence that hybridizes to one of the foregoing nucleic acid sequences under conditions equivalent to about 20° C. to 27° C. below $T_m$ and 1 M sodium chloride, e.g., a nucleic acid sequence that hybridizes to one of the foregoing nucleic acid sequences under stringent conditions, e.g., highly stringent conditions.

A "CD2-binding agent" is an agent which interacts with (e.g., binds to the extracellular portion of) CD2 and preferably modulates (preferably decreases) the CD2:LFA-3 interaction and/or modulates CD2 signaling. Examples of CD2-binding agents include: soluble CD2-binding fragments of a naturally occurring CD2 ligand, e.g., LFA-3; soluble fusions of LFA-3, or a CD2-binding fragment thereof, to another protein or polypeptide, e.g., an immunoglobulin or a fragment thereof; an LFA-3/CD2 fusion polypeptide; antibodies which bind CD2, e.g., recombinant, monoclonal, chimeric, CDR-grafted, humanized, human, or rodent antibodies; and small molecule or peptidomimetics.

An "LFA-3-binding agent" is an agent which interacts with (e.g., binds to the extracellular portion of) LFA-3 and preferably modulates (preferably decreases) the CD2:LFA-3 interaction and/or modulates LFA-3 signaling. Examples of LFA-3-binding agents include: soluble LFA-3 binding fragments of a naturally occurring LFA-3 ligand, e.g., CD2; soluble fusions of CD2, or an LFA-3 binding fragment thereof, to another protein or polypeptide, e.g., an immunoglobulin or a fragment thereof; an LFA-3/CD2 fusion polypeptide; antibodies which bind LFA-3, e.g., recombinant, monoclonal, chimeric, CDR-grafted, humanized, human, or rodent antibodies; and small molecule or peptidomimetics.

An "LFA-3/IgG" fusion polypeptide is a fusion polypeptide which includes an LFA-3 sequence which binds the extracellular portion of CD2 and all or a portion of an immunoglobulin sequence, e.g., a portion of an immunoglobulin sequence which interacts with an Fc receptor. The LFA-3 sequence can be full length LFA-3 or a CD2-binding fragment thereof. In a preferred embodiment, the LFA-3 sequence is human LFA-3, and preferably a sequence which is identical to one or both alleles of the subject. Other embodiments can include a modified LFA-3 sequence, e.g., one which differs from a human LFA-3 sequence by at least 1, but less than, 3, 4, 5, or 6 residues. (The complete amino acid sequence of a human LFA-3 is found at SEQ ID NO:1 or 3 of U.S. Pat. No. 6,162,432, which is hereby incorporated by reference). A preferred LFA-3/IgG fusion protein is encoded by a nucleic acid having the nucleotide sequence shown in SEQ ID NO:7, and having the amino acid sequence shown in SEQ ID NO:8, of U.S. Pat. No. 6,162,432, which is hereby incorporated by reference.

As used herein, a "soluble LFA-3 polypeptide" or a "soluble CD2 polypeptide" is an LFA-3 or CD2 polypeptide incapable of anchoring itself in a biological membrane. Such soluble polypeptides include, for example, CD2 and LFA-3 polypeptides that lack a sufficient portion of their membrane spanning domain to anchor the polypeptide or are modified such that the membrane spanning domain is non-functional. As used herein soluble LFA-3 polypeptides include full-length or truncated (e.g., with internal deletions) PI-linked LFA-3.

As used herein, an "antibody homolog" is a protein comprising one or more polypeptides selected from immunoglobulin light chains, immunoglobulin heavy chains and antigen-binding fragments thereof which are capable of binding to an antigen. The component polypeptides of an antibody homolog composed of more than one polypeptide may optionally be disulfide-bound or otherwise covalently crosslinked. Accordingly, antibody homologs include intact immunoglobulins of types IgA, IgG, IgE, IgD, IgM (as well as subtypes thereof), wherein the light chains of the immunoglobulin may be of types kappa or lambda. Antibody homologs also include portions of intact immunoglobulins that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. The term includes recombinant antiboides, chimeric, CDR-grafted and humanized antibodies, or other antibodies modified to be less immunogenic in a human.

As used herein, a "humanized recombinant or humanized antibody homolog" is an antibody homolog, produced by recombinant DNA technology, in which some or all of the amino acids of a human immunoglobulin light or heavy chain that are required for antigen binding have been substituted for the corresponding amino acids from a nonhuman mammalian immunoglobulin light or heavy chain.

As used herein, a "chimeric recombinant antibody homolog" is an antibody homolog, produced by recombinant DNA technology, in which all or part of the hinge and constant regions of an immunoglobulin light chain, heavy chain, or both, have been substituted for the corresponding regions from another immunoglobulin light chain or heavy chain.

Sequences similar or homologous (e.g., at least about 85% sequence identity) to the sequences disclosed herein are also part of this application. In some embodiments, the sequence identity can be about 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand.

The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and minor regions of non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homolog"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453 ) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

As used herein, the term "similarity" means that a sequence of interest differs from a reference sequence by the presence of one or more amino acid substitutions (although modest amino acid insertions or deletions may also be present). Presently preferred means of calculating degrees of similarity to a reference sequence are through the use of BLAST and Pfam algorithms available, respectively, through Washington University at http://blast.wustl.edu and http://pfam.wustl.edu, in each case, using the algorithm default or recommended parameters for determining significance of calculated sequence relatedness. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

As used herein, the term "hybridizes under low stringency, medium stringency, high stringency, or very high stringency conditions" describes conditions for nucleic acid hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6×sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the polypeptides of the invention may have additional conservative or non-essential amino acid substitutions, which do not have a substantial effect on the polypeptide function. Whether or not a particular substitution will be tolerated, i.e., will not adversely affect desired biological properties, such as binding activity can be determined as described in Bowie, J U et al. (1990) *Science* 247:1306-1310.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of a hybrid antibody, without abolishing or more preferably, without substantially altering a biological activity, whereas an "essential" amino acid residue results in such a change.

Disorders

The methods of this invention are useful to prevent or treat mammalian, e.g., primate, or human, fibrotic or sclerotic conditions characterized by increased T cell activation. Stimulation of fibroblast activity is involved in the development of fibrotic or sclerotic disorders, including spontaneous and induced conditions. Abnormal accumulation of collagen in the extracellular matrix, resulting from excessive fibroblast proliferation and/or collagen production, can cause fibrosis of a number of tissues including the skin. Many common debilitating diseases, such as liver cirrhosis and pulmonary fibrosis, involve the proliferation of fibrous tissue as do certain diseases of the skin and/or connective tissue such as scleroderma, and the formation of adhesions, keloids, and hypertrophic scars.

The present invention provides a method of treating or preventing diseases characterized by acute and chronic inflammation and progressive fibrosis or sclerosis, dermal fibrosing disorders, fibrosis of internal organs, skeletal muscle fibrosis, cardiovascular fibrotic disorders, or fibrotic ocular disorders in subjects, preferably mammals, in need of such treatment, or at risk of such a disorder. The method is effective for reducing the extent of, or preventing the progression of, such disorders in the subject.

Dermal fibrosing disorders include, but are not limited to, scleroderma as described above, morphea, keloids, hypertrophic scars, familial cutaneous collagenoma, and connective tissue nevi of the collagen type.

Fibrosis of internal organs (e.g., liver, lung, kidney, heart, blood vessels, gastrointestinal tract as described above), occurs in disorders such as pulmonary fibrosis, liver cirrhosis, and scar formation. Scleroderma also frequently progresses to include fibrosis of internal organs. For example, fibrosis of the lungs is particularly amenable for treatment. Impairments in lung function can be detected by examining T cell population in the bronchoalveolar lavage (BAL) fluids from scleroderma patients, especially in patients with lung inflammation, e.g., by detecting the number and degree of activation of $CD8^+T$ cells, compared to controls as described herein. The percentage of BAL $CD8^+T$ cells negatively correlates with pulmonary function tests (PFTs) such as forced vital capacity (FVC) and diffusing capacity for carbon monoxide (DLco) (% predicted). An improvement in one or more of the aforesaid symptoms of lung fibrosis is indicative of therapeutic effectiveness of the treatment protocol.

Skeletal muscle fibrosis is a phenomenon which frequently occurs in diseased or damaged muscle. It is characterized by the excessive growth of fibrous tissue, and impairs muscle function. The amount of muscle function loss generally increases with the extent of fibrosis. Disorders which typically result in skeletal muscle fibrosis include, for example, muscular dystrophies, such as Duchenne's muscular dystrophy and Becker's muscular dystrophy; and neuromuscular diseases, such as acute polyneuritis, poliomyelitis, Werdig/Hoffman disease, amyotrophic lateral sclerosis, and progressive bulbar atrophy. Such conditions also include traumatic denervation atrophy induced by either trauma or by neuromuscular disorders. Skeletal muscle fibrosis is often progressive.

Cardiovascular disease states involving fibrosis that can be treated by the methods of the present invention include left ventricular hypertrophy secondary to hypertension; and fibrosis associated with myocardial infarction, myocarditis, with ischemia-reperfusion injury to the heart, or arteriosclerotic changes in coronary arteries.

Fibrotic conditions of the eye include conditions such as diabetic retinopathy, postsurgical scarring (for example, after glaucoma filtering surgery), and proliferative vitreoretinopathy.

Diseases characterized by acute and chronic inflammation and progressive fibrosis or sclerosis which can be treated or prevented by the methods of the invention include autoimmune diseases (e.g., scleroderma, glomerulonephritis, and progressive systemic sclerosis); irradiation induced fibrosis; fibrosis of the heart following myocardial infarction or ischemia-reperfusion injury; fibrosis of the lung associated with adult respiratory distress syndrome, irradiation injury, immune-complex disease, inhalation of chronic irritants, or chemotherapeutic agents; cirrhosis of the liver; chronic graft rejection of transplanted organs; fibrosis of the skin following thermal exposure; gingival periodontal fibrosis; cataract formation; keloid and adhesion formation following surgery and trauma; and arteriosclerosis/atherosclerosis (Okada, Acta Pathologica Japonica 43:160 (1993); Nishi Br J Ophthalmology 80:63 (1996); Kuroki Br J Rheumatology 34:31 (1995); Nakao J Dental Res 74:1072 (1995); Herman Clinical Nephrology 46:34 (1996); Thornton Clin Exp Immunology 103:67 (1996); Garner J Investigative Dermatology 101:875 (1993); Salmon-Her Archives of Dermatology 132:802 (1996); Liao J Lab Clin Med 128:452 (1996)).

Subjects for Treatment

The methods of the invention may be practiced on any subject, e.g., a mammal, preferably on humans. As used herein, the term "subject" is intended to include human and non-human animals. The term "non-human animals" of the invention includes all vertebrates, preferably, mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc.

Preferred human subjects include a human patient having any condition characterized by increased fibrotic activity and T cell activation, such as any of the above-described disorders. In one embodiment, the subject is a patient having, or at risk of, scleroderma, e.g., systemic or circumscribed scleroderma. In other preferred embodiments, the subject is a patient at risk for, or having, fibrosis of the skin, or fibrosis of a visceral organ, e.g., lung, kidney, heart or gastrointestinal tract. Preferably, the subject has or is at risk for a disorder characterized by aberrant interstitial fibrosis, e.g., interstitial lung disease (e.g., a lung fibrotic condition chosen from fibrosing alveolitis associated with systemic sclerosis (FASSc), or pulmonary hypertension caused by vascular disease of the lung. For example, the subject can have a mean alveolar wall thickness of less than about 20 microns, between about 20 to 40 microns, or greater than about 40 microns. In other embodiments, the subject has a bronchoalveolar lavage (BAL) cell differential of at least (i.e., greater than or equal to) 3% neutrophils, or at least (i.e., greater than or equal to) 2.2% eosinophils. In yet other embodiments, the subject has one or more of: an elevated number of memory CD8+ cells in the BAL fluids from said subject, altered cytokine or chemokine gene expression in BAL cells, or abnormal T cell repertoire. In yet other embodiments, the subject has impaired vital organ function, e.g., decreased lung, kidney, or liver function. For example, the subject has abnormal pulmonary function tests (PFTs) scores, including spirometry, lung volume and diffusion capacity for carbon monoxide. In other embodiments, the subject has abnormal Raynaud's activity score.

Examples of symptoms characteristic of scleroderma include one or more of: diffuse fibrosis, accumulation of fibrotic tissue, increased in the number or activity of T cells (e.g., CD8+ T cells), degenerative abnormalities, and/or abnormalities in the skin (scleroderma), articular structures, or internal organs (e.g., lungs, heart, kidneys, liver, esophagus, and GI tract.

The identification of any of the aforesaid symptoms in a subject is indicative that treatment will be appropriate.

Inhibitors Of The CD2:LFA-3 Interaction

Any inhibitor of the CD2:LFA-3 interaction is useful in the methods of this invention. Such inhibitors include anti-LFA-3 antibody homologs, anti-CD2 antibody homologs, soluble LFA-3 polypeptides, soluble CD2 polypeptides, small molecules, e.g., (e.g., a chemical agent having a molecular weight of less than 2500 Da, preferably, less than 1500 Da, a chemical, e.g., a small organic molecule, e.g., a product of a combinatorial library), LFA-3 and CD2 mimetic agents and derivatives thereof. Preferred inhibitors are soluble LFA-3 polypeptides and anti-LFA-3 antibody homologs.

The utility in the methods of this invention of specific soluble CD2 polypeptides, soluble LFA-3 polypeptides, anti-LFA-3 antibody homologs, anti-CD2 antibody homologs or CD2 and LFA-3 mimetic agents may easily be determined by assaying their ability to inhibit the LFA-3/CD2 interaction.

This ability may be assayed, for example, using a simple cell binding assay that permits visual (under magnification) evaluation of the ability of the putative inhibitor to inhibit the interaction between LFA-3 and CD2 on cells bearing these molecules. Jurkat cells are preferred as the CD2$^+$ substrate and sheep red blood cells or human JY cells are preferred as the LFA-3$^+$ substrate. The binding characteristics of soluble polypeptides, antibody homologs and mimetic agents useful in this invention may be assayed in several known ways, such as by radiolabeling the antibody homolog, polypeptide or agent (e.g., $^{35}$S or $^{125}$I) and then contacting the labeled polypeptide, mimetic agent or antibody homolog with CD2$^+$ of LFA-3$^+$ cells, as appropriate. Binding characteristics may also be assayed using an appropriate enzymatically labelled secondary antibody. Rosetting competition assays such as those described by Seed et al. (*Proc. Natl. Acad. Sci. USA*, 84, pp. 3365-69 (1987)) may also be used.

Soluble CD2 and LFA-3 Polypeptides

Soluble LFA-3 polypeptides or soluble CD2 polypeptides that inhibit the interaction of LFA-3 and CD2 are useful in the methods of the present invention. Soluble LFA-3 polypeptides are preferred.

Soluble LFA-3 polypeptides may be derived from the transmembrane form of LFA-3, particularly the extracellular domain (e.g., $AA_1$-$AA_{187}$ of SEQ ID NO:2 of U.S. Pat. No. 6,162,432, which is hereby incorporated by reference). Such polypeptides are described in U.S. Pat. No. 4,956,281 and co-pending U.S. patent application Ser. No. 07/667,971 (which shares a common assignee with the present application), which are herein incorporated by reference. Preferred soluble LFA-3 polypeptides include polypeptides consisting of $AA_1$-$AA_{92}$ of SEQ ID NO:2, $AA_1$-$AA_{80}$ of SEQ ID NO:2, $AA_{50}$-$AA_{65}$ of SEQ ID NO:2 and $AA_{20}$-$AA_{80}$ of SEQ ID NO:2, wherein SEQ ID NO:2 is shown in U.S. Pat. No. 6,162,432, which is hereby incorporated by reference. A vector comprising a DNA sequence encoding SEQ ID NO:2 (i.e., SEQ ID NO: 1) is deposited with the American Type Culture Collection, Rockville, Md. under Accession No. 75107, wherein of SEQ ID NO:1 and 2 are shown in U.S. Pat. No. 6,162,432, which are hereby incorporated by reference.

Soluble LFA-3 polypeptides may also be derived from the PI-linked form of LFA-3, such as those described in PCT patent application Ser. No. WO 90/02181. A vector comprising a DNA sequence encoding PI-linked LFA-3 (i.e., SEQ ID NO:3) is deposited with the American Type Culture Collection, Rockville, Md. under Accession No. 68788. It is to be understood that the PI-linked form of LFA-3 and the transmembrane form of LFA-3 have identical amino acid sequences through the entire extracellular domain. Accordingly, the preferred PI-linked LFA-3 polypeptides are the same as for the transmembrane form of LFA-3.

The most preferred fusion proteins for use in the present invention contain the amino terminal 92 amino acids of mature LFA-3, the C-terminal 10 amino acids of a human IgG1 hinge region containing the two cysteine residues thought to participate in interchain disulfide bonding, and the $C_H2$ and $C_H3$ regions of a human IgG$_1$ heavy chain constant domain (e.g., SEQ ID NO:8). This fusion protein is referred to herein as "LFA-3TIP" or "Alefacept."

Alefacept is a fusion protein that includes the first extracellular domain of human LFA-3 (CD58) fused to an Fc portion of human IgG1 (specifically, the hinge CH2 and CH3 domains). The protein is a glycosylated, disulfide linked dimer with a molecular weight of about 112 kD under PAGE nonreducing conditions. The constant region of alefacept has C-terminal variability which corresponds to a splice variant form of the full length fusion polypeptide.

The nucleotide sequence of the pSAB152 insert is SEQ ID NO:7. SEQ ID NO:7 and 8 are shown in U.S. Pat. No. 6,162,432, which are hereby incorporated by reference. A plasmid, pSAB152, encoding an exemplary LFA-3TIP is deposited with American Type Culture Collection, Rockville, Md., under the accession number ATCC 68720. The amino acid sequence of a longer splice variant of LFA-3TIP than the one shown in U.S. Pat. No. 6,162,432 differs from the shorter variant by having six amino acids added to the C-terminal end.

pMDR(92)Ig-3 is an example of an expression vector that can be used to produce alefacept. pMDR(92)Ig-3 includes the following elements: (a) A segment of pBR322 containing the ColE1 origen and beta lactamase expression cassette (GenBank Accession No. J01749); (b) DHFR expression cassette consisting of: SV40 early promoter with the enhancer deleted (a portion of GenBank Accession No. J02400), murine DHFR cDNA (GenBank Accession No. L26316), SV40 poly A site and small t intron (portions of GenBank Accession No. J02400), and human gastrin transcription terminator sequence, 3'UTR (Sato et al. (1986) *Mol Cell Biol* 6:1032-1043); (c) an alefacept expression cassette including, preferably in the following order: The SV40 early promoter/enhancer (GenBank Accession No. J02400), Adenovirus Major Late Promoter and tripartite leader, including a splice donor and intron sequence (a portion of GenBank Accession No. J01917), murine Ig heavy chain variable region intron sequence and splice acceptor (Kaufman and Sharp (1982) Mol Cell Biol. 2: 1304-1319, (optionally) cloning linkers, the first 92 amino acids of LFA-3 gene as isolated from a human tonsil cDNA library, fused in frame to a nucleic acid encoding the hinge CH2 and CH3 regions of a human IgG1 gene as isolated from a human fibroblastic genomic DNA library, cloning linkers (optionally), MIS 3' UT region including poly A site (GenBank Accession No. K03474), and SV40 polyA site and small t intron (GenBank Accession No. J02400); and a segment of pBR327 (GenBank Accession No. L08856).

Host cell lines that can be used to produce alefacept can be derived from CHO-DUkX-B 1 cells. In one embodiment, a DHFR(−) mutant of this cell line can be transfected with the vector pMDR(92)Ig-3, and DHFR(+) transformants can be cultured in selective medium (e.g., containing 25 nM of methotrexate (MTX)). Positive transformants can be subjected to increasing concentrations of MTX (e.g., 50 nM), and colonies producing high levels of alefacept can then be selected.

Production of alefacept can be carried out as follows: CHO host cells are thawed, scaled up to a culture of 2000 L, maintained in culture for 6-7 days with pH control and nutrient feed (at 48 hrs., 96 hrs., and 120 hrs.), after which conditioned medium is harvested through microfiltration. MTX is preferably present in the culture medium. Alefacept can be recovered from the conditioned medium by carrying out the following steps: (i) Protein A chromatography, (ii) ceramic hydroxyapatite chromatography, (iii) viral inactivation at low pH, (iv) hydrophobic interaction chromatography, (v) followed by concentration, diafiltration, viral filtration, and a second concentration step which yields fusion product.

Another way of producing alefacept for use in the methods of this invention is described in co-pending, commonly assigned U.S. patent application Ser. No. 07/770,967. Generally, conditioned culture medium of COS7 or CHO cells transfected with pSAB152 was concentrated using an AMICON S1Y30 spiral cartridge system (AMICON, Danvers, Mass.) and subjected to Protein A-Sepharose 4B (Sigma, St. Louis, Mo.) chromatography. The bound proteins were eluted and subjected to Superose-12 (Pharmacia/LKB, Piscataway, N.J.) gel filtration chromatography.

Superose-12 fractions containing alefacept with the least amount of contaminating proteins, as determined on SDS-PAGE gels and by Western blot analysis, (see, e.g., Towbin et al., *Proc. Natl. Acad. Sci. USA*, 74, pp. 4350-54 (1979); *Antibodies: A Laboratory Manual*, pp. 474-510 (Cold Spring Harbor Laboratory (1988)), were pooled and concentrated in a YM30 Centricon (AMICON). Alefacept was detected on Western blots using a rabbit anti-LFA-3 polyclonal antiserum, followed by detectably labeled goat anti-rabbit IgG. The purified alefacept of COS7 or CHO cells was a dimer of two monomeric LFA-3-Ig fusion proteins, connected by disulfide bonds.

LFA-3-Ig fusion activity can be tested using the following bioassays: (1) a CD32/64 (Fc gamma RI/RII) U937 cell bridging assay, and (2) a CD16 (Fc gamma RIII) Jurkat cell bridging assay. Both assays test the ability of alefacept to bridge CHO cells displaying cell surface CD2 to cells expressing Fc-gamma receptors. The latter assay, assay (2), involves culturing adherent CHO-CD2 cells to form a monolayer in 96-well plates; adding alefacept controls and samples; adding fluorescently labeled Jurkat-CD16(+); and measuring fluorescence intensity.

Binding of LFA-3-Ig fusion to CD2 immobilized onto a substrate, e.g., a chip, can also be used to test the fusion proteins.

Soluble CD2 polypeptides may be derived from full length CD2, particularly the extracellular domain (e.g., $AA_1$-$AA_{185}$ of SEQ ID NO:6). Such polypeptides may comprise all or part of the extracellular domain of CD2. Exemplary soluble CD2 polypeptides are described in PCT WO 90/08187, which is herein incorporated by reference.

The production of the soluble polypeptides useful in this invention may be achieved by a variety of methods known in the art. For example, the polypeptides may be derived from intact transmembrane LFA-3 or CD2 molecules or an intact PI-linked LFA-3 molecule by proteolysis using specific endopeptidases in combination with exopeptidases, Edman degradation, or both. The intact LFA-3 molecule or the intact CD2 molecule, in turn, may be purified from its natural source using conventional methods. Alternatively, the intact LFA-3 or CD2 may be produced by known recombinant DNA techniques using cDNAs (see, e.g., U.S. Pat. No. 4,956,281 to Wallner et al.; Aruffo and Seed, *Proc. Natl. Acad. Sci.*, 84, pp. 2941-45 (1987); Sayre et al., *Proc. Natl. Acad. Sci. USA*, 84, pp.2941-45 (1987)).

Preferably, the soluble polypeptides useful in the present invention are produced directly, thus eliminating the need for an entire LFA-3 molecule or an entire CD2 molecule as a starting material. This may be achieved by conventional chemical synthesis techniques or by well-known recombinant DNA techniques wherein only those DNA sequences which encode the desired peptides are expressed in transformed hosts. For example, a gene which encodes the desired soluble LFA-3 polypeptide or soluble CD2 polypeptide may be synthesized by chemical means using an oligonucleotide synthesizer. Such oligonucleotides are designed based on the amino acid sequence of the desired soluble LFA-3 polypeptide or soluble CD2 polypeptide. Specific DNA sequences coding for the desired peptide also can be derived from the full length DNA sequence by isolation of specific restriction endonuclease fragments or by PCR synthesis of the specified region.

Standard methods may be applied to synthesize a gene encoding a soluble LFA-3 polypeptide or a soluble CD2 polypeptide that is useful in this invention. For example, the complete amino acid sequence may be used to construct a back-translated gene. A DNA oligomer containing a nucleotide sequence coding for a soluble LFA-3 polypeptide or a soluble CD2 polypeptide useful in this invention may be synthesized in a single step. Alternatively, several smaller oligonucleotides coding for portions of the desired polypeptide may be synthesized and then ligated. Preferably, a soluble LFA-3 polypeptide or a soluble CD2 polypeptide useful in this invention will be synthesized as several separate oligonucleotides which are subsequently linked together. The individual oligonucleotides typically contain 5' or 3' overhangs for complementary assembly.

Once assembled, preferred genes will be characterized by sequences that are recognized by restriction endonucleases (including unique restriction sites for direct assembly into a cloning or an expression vector), preferred codons taking into consideration the host expression system to be used, and a sequence which, when transcribed, produces a stable, efficiently translated mRNA. Proper assembly may be confirmed by nucleotide sequencing, restriction mapping, and expression of a biologically active polypeptide in a suitable host.

It will be appreciated by those of skill in the art that, due to the degeneracy of the genetic code, DNA molecules comprising many other nucleotide sequences will also be capable of encoding the soluble LFA-3 and CD2 polypeptides encoded by the specific DNA sequences described above. These degenerate sequences also code for polypeptides that are useful in this invention.

The DNA sequences may be expressed in unicellular hosts, or preferably in isolated mammalian host cells. As is well known in the art, in order to obtain high expression levels of a transfected gene in a host, the gene must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an additional expression marker useful in the expression host.

The DNA sequences encoding the desired soluble polypeptides may or may not encode a signal sequence. If the expression host is prokaryotic, it generally is preferred that the DNA sequence not encode a signal sequence. If the expression host is eukaryotic, it generally is preferred that a signal sequence be encoded.

An amino terminal methionine may or may not be present on the expressed product. If the terminal methionine is not cleaved by the expression host, it may, if desired, be chemically removed by standard techniques.

A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2µ plasmid and derivatives thereof. Useful vectors for insect cells include pVL 941.

In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

A wide variety of host cells are useful. Host cells can be a unicellular organism, or can be obtained from a multicellular organism, e.g., isolated cells from a multicellular host. These hosts may include well known eukaryotic and prokaryotic hosts, such as strains of *E. coli, Pseudomonas, Bacillus, Streptomyces*, fungi, yeast, insect cells such as *Spodoptera frugiperda* (SF9), animal cells such as CHO and mouse cells, African green monkey cells such as COS 1, COS 7, BSC 1, BSC 40, and BMT 10, and human cells, as well as plant cells in tissue culture. For animal cell expression, CHO cells and COS 7 cells are preferred.

It should be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with the DNA sequences discussed herein, particularly as regards potential secondary structures. Unicellular hosts should be selected by consideration of their compatibility with the chosen vector, the toxicity of the product coded for by the DNA sequences, their secretion characteristics, their ability to fold the soluble polypeptides correctly, their fermentation or culture requirements, and the ease of purification of the products coded for by the DNA sequences.

Within these parameters, one of skill in the art may select various vector/expression control sequence/host combinations that will express the desired DNA sequences on fermentation or in large scale animal culture, for example with CHO cells or COS 7 cells.

The soluble LFA-3 and CD2 polypeptides may be isolated from the fermentation or cell culture and purified using any of a variety of conventional methods. One of skill in the art may select the most appropriate isolation and purification techniques.

While recombinant DNA techniques are the preferred method of producing useful soluble CD2 polypeptides or soluble LFA-3 polypeptides having a sequence of more than 20 amino acids, shorter CD2 or LFA-3 polypeptides having less than about 20 amino acids are preferably produced by conventional chemical synthesis techniques. Synthetically produced polypeptides useful in this invention can advantageously be produced in extremely high yields and can be easily purified.

Preferably, such soluble CD2 polypeptides or soluble LFA-3 polypeptides are synthesized by solution phase or solid phase polypeptide synthesis and, optionally, digested with carboxypeptidase (to remove C-terminal amino acids) or degraded by manual Edman degradation (to remove N-terminal amino acids). The use of solution phase synthesis advantageously allows for the direct addition of certain derivatized amino acids to the growing polypeptide chain, such as the O-sulfate ester of tyrosine. This obviates the need for a subsequent derivatization step to modify any residue of the polypeptides useful in this invention.

Proper folding of the polypeptides may be achieved under oxidative conditions which favor disulfide bridge formation as described by Kent, "Chemical Synthesis of Polypeptides and Proteins", *Ann. Rev. Biochem.*, 57, pp. 957-89 (1988). Polypeptides produced in this way may then be purified by separation techniques widely known in the art.

Anti-LFA-3 And Anti-CD2 Antibody Homologs

Many types of anti-LFA-3 or anti-CD2 antibody homologs are useful in the methods of this invention. These include monoclonal antibodies, recombinant antibodies, chimeric recombinant antibodies, humanized recombinant antibodies, as well as antigen-binding portions of the foregoing.

Among the anti-LFA-3 antibody homologs, it is preferable to use monoclonal anti-LFA-3 antibodies. It is more preferable to use a monoclonal anti-LFA-3 antibody produced by a hybridoma selected from the group of hybridomas having Accession Nos. ATCC HB 10693 (1E6), ATCC HB 10694 (HC-1B11), ATCC HB 10695 (7A6), and ATCC HB 10696 (8B8), or the monoclonal antibody known as TS2/9 (Sanchez-Madrid et al., "Three Distinct Antigens Associated with Human T-Lymphocyte-Mediated Cytolysis: LFA-1, LFA-2 and LFA-3", *Proc. Natl. Acad. Sci. USA*, 79, pp. 7489-93 (1982)). Most preferably, the monoclonal anti-LFA-3 antibody is produced by a hybridoma selected from the group of hybridomas having Accession Nos. ATCC HB 10695 (7A6) and ATCC HB 10693 (1E6).

Among the anti-CD2 antibody homologs, it is preferable to use monoclonal anti-CD2 antibodies, such as the anti-CD2 monoclonal antibodies known as the $T11_1$ epitope antibodies, including TS2/18 (Sanchez-Madrid et al., "Three Distinct Antigens Associated with Human T-Lymphocyte-Mediated Cytolysis: LFA-1, LFA-2 and LFA-3", *Proc. Natl. Acad. Sci. USA*, 79, pp. 7489-93 (1982)).

The technology for producing monoclonal antibodies is well known. See generally, Harlow, E. and Lane, D. (1988) *Antibodies: A Laboratory Manual*, Cold Spring Harbor Laboratory Press, Cold Spring Harbor, N.Y.; Kohler et al., *Nature*, "Continuous Cultures of Fused Cells Secreting Antibody of Predefined Specificity", 256, pp. 495-97 (1975). Useful immunogens for the purpose of this invention include CD2- or LFA-3-bearing cells, as well as cell free preparations containing LFA-3, CD2 or counter receptor-binding fragments thereof (e.g., CD2 fragments that bind to LFA-3 or LFA-3 fragments that bind to CD2).

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, useful anti-LFA-3 or anti-CD2 antibodies may be identified by testing the ability of the immune serum to block sheep red blood cell rosetting of Jurkat cells, which results from the presence of LFA-3 and CD2 on the respective surfaces of these cells. The lymphocytes used in the production of hybridoma cells typically are isolated from immunized mammals whose sera have already tested positive for the presence of the desired antibodies using such screening assays.

Anti-CD2 and anti-LFA-3 antibody homologs useful in the present invention may also be recombinant antibodies produced by host cells transformed with DNA encoding immunoglobulin light and heavy chains of a desired antibody. Recombinant antibodies may be produced by well known genetic engineering techniques. See, e.g., U.S. Pat. No. 4,816,397, which is incorporated herein by reference. For example, recombinant antibodies may be produced by cloning cDNA or genomic DNA encoding the immunoglobulin light and heavy chains of the desired antibody from a hybridoma cell that produces an antibody homolog useful in this invention. The cDNA or genomic DNA encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector.

Prokaryotic or eukaryotic host cells may be used. Expression in eukaryotic host cell is preferred because such cells are more likely than prokaryotic cells to assemble and secrete a properly folded and immunologically active antibody. It is possible that the host cells will produce portions of intact antibodies, such as light chain dimers or heavy chain dimers, which also are antibody homologs according to the present invention.

It will be understood that variations on the above procedure are useful in the present invention. For example, it may be desired to transform a host cell with DNA encoding either the light chain or the heavy chain (but not both) of an antibody homolog. Recombinant DNA technology may also be used to remove some or all of the DNA encoding either or both of the light and heavy chains that is not necessary for CD2 or LFA-3 counter receptor binding. The molecules expressed from such truncated DNA molecules are useful in the methods of this invention. In addition, bifunctional antibodies may be produced in which one heavy and one light chain are anti-CD2 or anti-LFA-3 antibody homologs and the other heavy and light chain are specific for an antigen other than CD2 or LFA-3, or another epitope of CD2 or LFA-3.

Chimeric recombinant anti-LFA-3 or anti-CD2 antibody homologs may be produced by transforming a host cell with a suitable expression vector comprising DNA encoding the desired immunoglobulin light and heavy chains in which all or some of the DNA encoding the hinge and constant regions of the heavy and/or the light chain have been substituted with DNA from the corresponding region of an immunoglobulin light or heavy chain of a different species. When the original recombinant antibody is nonhuman, and the inhibitor is to be administered to a human, substitution of corresponding human sequences is preferred. An exemplary chimeric recombinant antibody has mouse variable regions and human hinge and constant regions. See generally, U.S. Pat. No. 4,816,397; Morrison et al., "Chimeric Human Antibody Molecules: Mouse Antigen-Binding Domains With Human Constant Region Domains", *Proc. Natl. Acad. Sci. USA*, 81, pp. 6851-55 (1984); Robinson et al., International Patent Publication PCT/US86/02269; Akira, et al., European Patent Application 184,187; Taniguchi, M., European Patent Application 171,496; Neuberger et al., International Application WO 86/01533; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

Humanized recombinant anti-LFA-3 or anti-CD2 antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an anti-LFA-3 or anti-CD2 antibody. Nucleic acids encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDR's of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDR's of a particular human antibody may be replaced with at least a portion of a non-human CDR or only some of the CDR's may be replaced with non-human CDR's. It is only necessary to replace the number of CDR's required for binding of the humanized antibody to a predetermined antigen, e.g., LFA-3 or CD2.

Also within the scope of the invention are humanized antibodies, including immunoglobulins, in which specific amino acids have been substituted, deleted or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the contents of which are hereby incorporated by reference. Other techniques for humanizing immunoglobulin chains, including antibodies, are described in Padlan et al. EP 519596 A1, published on Dec. 23, 1992.

Human monoclonal antibodies (mAbs) directed against human LFA-3 or CD2 can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855;

Bruggeman et al. 1993 *Year Immunol* 7:33-40; Tuaillon et al. 1993 *PNAS* 90:3720-3724; Bruggeman et al. 1991 *Eur J Immunol* 21:1323-1326).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR (Larrick et al.,1991, *Biotechniques* 11:152-156; Larrick et al., 1991, *Methods: Companion to Methods in Enzymology* 2:106-110).

Examples of methods and reagents particularly amenable for use in generating a variegated antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982. Kits for generating phage display libraries are commercially available (e.g., the Pharmacia Recombinant Phage Antibody System, catalog no. 27-9400-01; and the Stratagene SurfZAPTM phage display kit, catalog no. 240612).

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552-554, complete VH and VL domains of an antibody, joined by a flexible (Gly4-Ser)3 linker can be used to produce a single chain antibody which can render the display package separable based on antigen affinity. Isolated scFV antibodies immunoreactive with the antigen can subsequently be formulated into a pharmaceutical preparation for use in the subject method.

Specific antibodies with high affinities for a surface protein can be made according to methods known to those in the art, e.g, methods involving screening of libraries (Ladner, R. C., et al., U.S. Pat. No. 5,233,409; Ladner, R. C., et al., U.S. Pat. No. 5,403,484). Further, the methods of these libraries can be used in screens to obtain binding determinants that are mimetics of the structural determinants of antibodies. See for example Bajorath, J. and S. Sheriff, 1996, Proteins: Struct., Funct., and Genet. 24 (2), 152-157; Webster, D. M. and A. R. Rees, 1995, "Molecular modeling of antibody-combining sites," in S. Paul, Ed., Methods in Molecular Biol. 51, Antibody Engineering Protocols, Humana Press, Totowa, N.J., pp 17-49; and Johnson, G., Wu, T. T. and E. A. Kabat, 1995, "Seqhunt: A program to screen aligned nucleotide and amino acid sequences," in Methods in Molecular Biol.51, op. cit., pp 1-15.

Anti-CD2 and anti-LFA-3 antibody homologs that are not intact antibodies are also useful in this invention. Such homologs may be derived from any of the antibody homologs described above. For example, antigen-binding fragments, as well as full-length monomeric, dimeric or trimeric polypeptides derived from the above-described antibodies are themselves useful. Useful antibody homologs of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. Anti-LFA-3 heavy chains are preferred anti-LFA-3 antibody fragments.

Antibody fragments may also be produced by chemical methods, e.g., by cleaving an intact antibody with a protease, such as pepsin or papain, and optionally treating the cleaved product with a reducing agent. Alternatively, useful fragments may be produced by using host cells transformed with truncated heavy and/or light chain genes. Heavy and light chain monomers may be produced by treating an intact antibody with a reducing agent, such as dithiothreitol, followed by purification to separate the chains. Heavy and light chain monomers may also be produced by host cells transformed with DNA encoding either the desired heavy chain or light chain, but not both. See, e.g., Ward et al., "Binding Activities of a Repertoire of Single Immunoglebulin Variable Domains Secreted from *Escherichia coli*", Nature, 341, pp. 544-46 (1989); Sastry et al., "Cloning of the Immunological Repertoire in *Escherichia coli* for Generation of Monoclonal Catalytic Antibodies: Construction of a Heavy Chain Variable Region-Specific cDNA Library", *Proc. Natl. Acad. Sci. USA,* 86, pp. 5728-32 (1989).

LFA-3 And CD2 Mimetic or Small Molecule Agents

Also useful in the methods of this invention are LFA-3 and CD2 mimetic agents. These agents which may be peptides, semi-peptidic compounds or non-peptidic compounds (e.g., small organic molecules), are inhibitors of the CD2:LFA-3 interaction. A preferred CD2 and LFA-3 mimetic agents will inhibit the CD2:LFA-3 interaction at least as well as anti-LFA-3 monoclonal antibody 7A6 or anti-CD2 monoclonal antibody TS2/18 (described supra).

In preferred embodiments, the test agent is a member of a combinatorial library, e.g., a peptide or organic combinatorial library, or a natural product library. In a preferred embodiment, the plurality of test compounds, e.g., library members, includes at least 10, $10^2$, $10^3$, $10^4$, $10^5$, $10^6$, $10^7$, or $10^8$ compounds. In a preferred embodiment, the plurality of test compounds, e.g., library members, share a structural or functional characteristic.

In one embodiment, the invention provides libraries of LFA-3 and/or CD2 inhibitors. The synthesis of combinatorial libraries is well known in the art and has been reviewed (see, e.g., E. M. Gordon et al., *J. Med. Chem.* (1994) 37:1385-1401; DeWitt, S. H.; Czamik, A. W. *Acc. Chem. Res.* (1996) 29:114; Arnstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds of the invention can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads is added a solution of a different activated amino acid, and the reactions are allow to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" linrary, e.g., a library in which certain portions of the inhibitor are selected non-randomly, e.g., to provide an inhibitor having known structural similarity or homology to a known peptide capable of interacting with an antibody, e.g., the an antiidiotypic antibody antigen binding site. It will be appriciated that a wide variety of peptide, peptidomimetic, or non-peptide compounds can be readily generated in this way The "split-pool" strategy results in a library of peptides, e.g., inhibitors, which can be used to prepare a library of test compounds of the invention. In another illustrative synthesis, a "diversomer library" is created by the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., *Nature* 354:84-86 (1991)) can also be used to synthesize libraries of compounds according to the subject invention.

Libraries of compounds can be screened to determine whether any members of the library have a desired activity, and, if so, to identify the active species. Methods of screening combinatorial libraries have been described (see, e.g., Gordon et al., *J Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are described below.

In one embodiment, compounds of the invention can be screened for the ability to interact with a CD2 or LFA-3 polypeptide by assaying the activity of each compound to bind directly to the polypeptide or to inhibit a CD2:LFA-3 interaction, e.g., by incubating the test compound with a CD2 or LFA-3 polypeptide and a lysate, e.g., a T or APC cell lysate, e.g., in one well of a multiwell plate, such as a standard 96-well microtiter plate. In this embodiment, the activity of each individual compound can be determined. A well or wells having no test compound can be used as a control. After incubation, the activity of each test compound can be determined by assaying each well. Thus, the activities of a plurality of test compounds can be determined in parallel.

In still another embodiment, large numbers of test compounds can be simultaneously tested for binding activity. For example, test compounds can be synthesized on solid resin beads in a "one bead-one compound" synthesis; the compounds can be immobilized on the resin support through a photolabile linker. A plurality of beads (e.g., as many as 100,000 beads or more) can then be combined with yeast cells and sprayed into a plurality of "nano-droplets", in which each droplet includes a single bead (and, therefore, a single test compound). Exposure of the nano-droplets to UV light then results in cleavage of the compounds from the beads. It will be appreciated that this assay format allows the screening of large libraries of test compounds in a rapid format.

Combinatorial libraries of compounds can be synthesized with "tags" to encode the identity of each member of the library (see, e.g., W. C. Still et al., U.S. Pat. No. 5,565,324 and PCT Publication Nos. WO 94/08051 and WO 95/28640). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels. Such a tagging scheme can be useful, e.g., in the "nano-droplet" screening assay described above, to identify compounds released from the beads.

In preferred embodiments, the libraries of compounds of the invention contain at least 30 compounds, more preferably at least 100 compounds, and still more preferably at least 500 compounds. In preferred embodiments, the libraries of compounds of the invention contain fewer than $10^9$ compounds, more preferably fewer than $10^8$ compounds, and still more preferably fewer than $10^7$ compounds.

Derivatized Inhibitors

Also useful in the methods of this invention are derivatized inhibitors of the CD2:LFA-3 interaction in which, for example, any of the antibody homologs, soluble CD2 and LFA-3 polypeptides, or CD2 and LFA-3 mimetic agents described herein are functionally linked (by chemical coupling, genetic fusion or otherwise) to one or more members independently selected from the group consisting of anti-LFA-3 and anti-CD2 antibody homologs, soluble LFA-3 and CD2 polypeptides, CD2 and LFA-3 mimetic agents, cytotoxic agents and pharmaceutical agents.

One type of derivatized inhibitor is produced by crosslinking two or more inhibitors (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Another possibility for cross-linking takes advantage of the PI linkage signal sequence in PI-linked LFA-3, or fragments thereof. Specifically, DNA encoding the PI-linkage signal sequence (e.g., $AA_{162}$-$AA_{212}$ of SEQ ID NO:4) is ligated downstream of DNA encoding a desired polypeptide, preferably a soluble LFA-3 polypeptide. If this construct is expressed in an appropriate eukaryotic cell, the cell will recognize the PI linkage signal sequence and will covalently link PI to the polypeptide. The hydrophobic property of the PI may then be exploited to form micellar aggregates of the polypeptides.

Also useful are inhibitors linked to one or more cytotoxic or pharmaceutical agents. Useful pharmaceutical agents include biologically active peptides, polypeptides and proteins, such as antibody homologs specific for a human polypeptide other than CD2 or LFA-3, or portions thereof. Useful pharmaceutical agents and cytotoxic agents also include cyclosporin A, prednisone, FK506, methotrexate, steroids, retinoids, interferon, and nitrogen mustard.

Preferred inhibitors derivatized with a pharmaceutical agent include recombinantly-produced polypeptides in which a soluble LFA-3 polypeptide, soluble CD2 polypeptide, or a peptidyl CD2 or peptidyl LFA-3 mimetic agent is fused to all or part of an immunoglobulin heavy chain hinge region and all or part of a heavy chain constant region. Preferred polypeptides for preparing such fusion proteins are soluble LFA-3 polypeptides. Most preferred are fusion proteins containing $AA_1$-$AA_{92}$ of LFA-3 (e.g., SEQ ID NO:2) fused to a portion of a human $IgG_1$ hinge region (including the C-terminal ten amino acids of the hinge region containing two cysteine residues thought to participate in interchain disulfide bonding) and the $C_H2$ and $C_H3$ regions of an $IgG_1$ heavy chain constant domain. Such fusion proteins are expected to exhibit prolonged serum half-lives and enable inhibitor dimerization.

Combination Therapy

The binding agents, e.g., CD2-or LFA-3 binding agents, may be used in combination with other therapies, e.g., other agents. The other agent(s) are referred to herein as "second agent(s)" and include one or more of: a cytokine binding agent, (e.g., type 2 cytokine binding agent, e.g., an IL-2- or IL-8-binding agent, e.g., an anti-IL-2 or IL-8 monoclonal antibody (Abgenix)); an inhibitor of an ICAM/LFA-1 interaction, e.g., an ICAM-binding agent (e.g., an antibody, e.g., a monoclonal antibody) against ICAM-1 (e.g., a humanized, chimeric, or human anti-ICAM-1 antibody); or an LFA-1 (also known as CD11a) binding agent (e.g., an antibody, e.g., a monoclonal antibody) against LFA-1 (e.g., a humanized, chimeric, or human anti-LFA-1 antibody, e.g., Xanelim (Genentech/Xoma)); a costimulatory molecule binding agent, e.g., a B7-1 (CD80) binding agent (e.g., an anti-B7-1 monoclonal antibody (IDEC); a vasodilator (e.g., an ACE inhibitor or minoxidil); an immunosuppressant (e.g., methotrexate, cyclosphorin, or chlorambucil); cyclophosphamide; a corticosteroid or penicillamine. In one embodiment, the agent, e.g., an inhibitor of the CD2:LFA-3 interaction, is administered in combination with one or more inhibitors of interleukin-1 (IL-1), IL-2, IL-4, IL-6, IL-8, TNF-.alpha., TGF-.beta., PDGF, granzyme A or leukotriene B4. Such combination therapy may advantageously utilize lower dosages of the therapeutic or prophylactic agents.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. E.g., the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder, e.g., reduction in T cell level or activity, is greater than what would be observed with one treatment delivered in the absence of the other. The effect of the two treatments can be partially additive, wholly additive, or greater than additive. The delivery can be such that an effect of the first treatment delivered is still detectable when the second is delivered, e.g., when the CD2- or LFA-3 binding agent is delivered first, a reduction in T cell level or activity is still detectable when second agent is delivered. In a preferred embodiment, a delivery of the first treatment and a delivery of the second treatment occur within 1, 2, 5, 10, 15, or 30 days of one another.

In a preferred embodiment, the CD2-binding agent (e.g., LFA-3/Ig fusion), the second agent (or both) or a pharmaceutical composition containing the same is administered systemically, e.g., intravenously, intramuscularly, subcutaneously, intra-articularly, transdermally, intrathecally, periostally, intratumorally, intralesionally, perilesionally by infusion (e.g., using an infusion device), orally, topically or by inhalation. Preferably, the CD2-binding agent is administered intramuscularly or intravenously. In other embodiment, the CD2-binding agent is administered locally, e.g., topically or by needleless injection, to an affected area.

The parenteral administration of the CD2-binding agent (e.g., LFA-3/Ig fusion), the second agent (or both) or a pharmaceutical composition containing the same can be effected using a needle or a needleless syringe by procedures known in the art. Examples of needleless syringe systems and modes of administration are described in U.S. Pat. Nos. 6,132,395, 6,096,002, 5,993,412, 5,893,397, 5,520,639, 5,503,627, 5,399,163, 5,383,851, 5,312,577, 5,312,335, the contents of all of which are hereby incorporated by reference.

Pharmaceutical Compositions

This invention provides a method for preventing or treating the above-mentioned skin conditions in a subject by administering to the mammal one or more CD2-binding agents, e.g., inhibitors of the CD2:LFA-3 interaction, or derivatized form(s) thereof, in combination with a second agent.

Preferably, an effective amount of the CD2-binding agents or derivatized form thereof is administered. By "effective amount" is meant an amount capable of lessening the spread or severity of the fibrotic and/or sclerotic conditions described herein. In therapeutic embodiments, an effective amount of a CD2- or LFA-3 binding agent refers to an amount of an agent which is effective, upon single or multiple dose administration to the subject, at inhibiting, reducing, or ameliorating the fibrotic or sclerotic disorder (e.g., inhibit fibrosis, attenuate the severity of, suppress the deleterious effects of, or reverse, a sclerotic or fibrotic disorder, e.g., a disorder as described herein, or preserve or restore function of a visceral organ), or in prolonging the survival of the patient with such disorders beyond that expected in the absence of such treatment. The amelioration of fibrosis is predicted to lead to improved quality of life, as assessed, e.g., by the SF-36 health questionnaire developed by RAND Health, a division of the RAND Corporation (Santa Monica, Calif.). For example, in cases of lung sclerotic disorders, an improvement in lung capacity, reduced respiratory distress (e.g., reduced dyspnea) is predicted. An effective amount does not necessarily indicate a total elimination of the disorder. In prophylactic embodiments, an effective amount of a CD2- or LFA-3 binding agent refers to an amount of an agent which is effective, upon single- or multiple-dose administration to the subject, in preventing or delaying the occurrence of the onset or recurrence of the disorder.

It will be apparent to those of skill in the art that the effective amount of agent will depend, inter alia, upon the disorder treated (e.g., fibrotic, sclerotic or T cell mediated disorder), administration schedule, the unit dose administered, whether the agent is administered in combination with other therapeutic agents, the immune status and health of the patient, the therapeutic or prophylactic activity of the particular agent administered and the serum half-life. Depending on the disorder to be treated the agent may be packaged differently.

Preferably, the CD2-binding agent is administered at a dose between about 0.001 and about 50 mg of the agent per kg body weight, more preferably, between about 0.01 and about 10 mg of the agent per kg body weight, most preferably between about 0.1 and about 4 mg of the agent per kg body weight.

Unit doses should be administered until an effect is observed. The effect may be measured by a variety of methods, including, in vitro T cell activity assays and clearing or improvement of affected skin areas, or improvement in other affected body areas as may be relevant to the particular fibrotic/sclerotic disorder. Preferably, the unit dose is administered at regular intervals, such as once a week. More preferably, it is administered at regular intervals, e.g., at weekly intervals for a therapeutic treatment period of several weeks, e.g., twelve weeks. More frequent administrations, e.g., two or three times per week are also envisioned and may be adapted if the subject's sclerotic disorder is severe or if urgent intervention is indicated. Less frequent administrations, e.g., once or twice per month, are also envisioned and may be adopted if the subject responds well to therapy such that maintenance dosing is appropriate. It will be recognized, however, that lower or higher dosages and other administration schedules may be employed.

The CD2-binding agent(s) or derivatized form(s) thereof are also preferably administered in a composition including a pharmaceutically acceptable carrier. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the agent.

Formulations, e.g., pharmaceutical formulations, of the CD2-binding agent(s) can be prepared in aqueous or non-aqueous, e.g., lyophilized, forms. Preferred pharmaceutical formulations are suitable for injection. An example of an aqueous formalation encompassed by the present invention includes phosphate buffered saline (PBS) frozen liquid formulation. An example of a lyophilized formulation includes one or more of: citrate, glycine and sucrose, preferably 2.5% sucrose, and 0.5% to 2% glycine, preferably 1% glycine, in sodium citrate-citric buffer (at least 10 mM, preferably 25 mM) buffered to a pH of at least about 4, preferably, 5, more preferably 6 (or even more preferably, 6.8).

The second agent may be administered in a single dosage form with the CD2-binding agent(s) (i.e., as part of the same pharmaceutical composition), a multiple dosage form, seperately from the CD2-binding agent(s) but concurrently, or a multiple dosage form wherein the two componets are administered separately and sequentially. Alternatively, the CD2-binding agent and the other active agent may be in the form of a single conjugated molecule. Conjugation of the two components may be achieved by standard cross-linking techniques well known in the art. A single molecule may also take the form of a recombinant fusion protein. In addition, a pharmaceutical composition useful in the present invention may be used in combination with other therapies such as PUVA, chemotherapy and UV light. Such combination therapies may advantageously utilize lower dosages of the therapeutic or prophylactic agents.

The CD2-binding agent, or pharmaceutical composition, may be in a variety of forms. These include, for example, solid, semi-solid and liquid dosage forms, such as tablets, pills, powders, liquid solutions, dispersions or suspensions, liposomes, suppositories, injectable, infusible, and topical preparations. The preferred form depends on the intended mode of administration and therapeutic application. The preferred forms are injectable or infusible solutions.

The invention includes formulations suitable for use as topically applied sunscreens or UV-protectants. Preferred embodiments include alefacept preparations. The active ingredient can be formulated in a liposome. The product can be applied before, during, or after UV exposure, or before, during, or after the development of redness.

Pharmacogenomics

This invention further provides a method for preventing or treating the above-mentioned conditions in a subject by administering to the mammal a pharmaceutical composition consisting of one or more CD2-binding agents, e.g., inhibitors of the CD2:LFA-3 interaction, or derivatized form(s) thereof, and optionally a second agent, wherein the genotype of the subject is determined at one or more genetic loci prior to administration of the pharmaceutical composition.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983-985 and Linder, M. W. et al. (1997) *Clin. Chem.* 43:254-266. Differences in metabolism of therapeutics can lead to severe toxicity or therapeutic failure by altering the relation between dose and blood concentration of the pharmacologically active drug. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms.

Information generated from pharmacogenomic research can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition, e.g., a composition consisting of one or more CD2-binding agents, e.g., inhibitors of the CD2:LFA-3 interaction, or derivatized form(s) thereof, to a patient, as a means of treating a disorder, e.g., a fibrotic disorder, e.g., a scelerotic disorder, e.g., scleroderma.

In one embodiment, a physician or clinician may consider applying knowledge obtained in relevant pharmacogenomics studies when determining whether to administer a pharmaceutical composition, e.g., a composition consisting of one or more CD2-binding agents, e.g., inhibitors of the CD2:LFA-3 interaction, or derivatized form(s) thereof, and optionally a second agent, to a subject. In another embodiment, a physician or clinician may consider applying such knowledge when determining the dosage, e.g., amount per treatment or frequency of treatments, of a pharmaceutical composition, e.g., a composition consisting of one or more CD2-binding agents, e.g., inhibitors of the CD2:LFA-3 interaction, or derivatized form(s) thereof, and optionally a second agent, administered to a patient.

In yet another embodiment, a physician or clinician may determine the genotypes, at one or more genetic loci, of a group of subjects participating in a clinical trial, wherein the subjects display a fibrotic disorder, e.g., a sclerotic disorder, e.g., scleroderma, and the clinical trial is designed to test the efficacy of a pharmaceutical composition, e.g., a composition consisting of one or more CD2-binding agents, e.g., inhibitors of the CD2:LFA-3 interaction, or derivatized form(s) thereof, and optionally a second agent, and wherein the physician or clinician attempts to correlate the genotypes of the subjects with their response to the pharmaceutical composition.

Kits

In another aspect, the invention provides kits which include one or more of: (i) a CD2-binding agent, an LFA-3-binding agent, or an inhibitor of the CD2:LFA-3 interaction, e.g., a CD2-binding agent or LFA-3 binding agent which inhibits the CD2:LFA-3 interaction, e.g., an agent described herein; (ii) a second agent, e.g., a second agent as described herein; and (iii) instructions on how to use the agent to treat a disorder described herein.

In a preferred embodiment, the CD2-binding agent is an LFA-3/Ig fusion polypeptide. Preferably, the LFA-3/Ig fusion polypeptide is lyophilized.

The following invention is further illustrated by the following examples, which should not be construed as further limiting. The contents of all references, pending patent applications and published patents, cited throughout this application are hereby expressly incorporated by reference.

EXAMPLES

Example I

Treatment Protocol

This example provides a protocol to test the clinical effects and tissue response of an inhibitor of the CD2:LFA-3 interaction (e.g., alefacept, human LFA-3/IgG1 fusion protein, formerly known as LFA-3TIP, in patients with scleroderma.

The primary outcome variable will be the number of memory $CD8^+$ T cells per ml BAL (bronchoalveolar lavage) fluid. The secondary study objectives are as follows: number of activated $CD8^+$ T cells in BAL fluid; number of memory and activated $CD4^+$ T cells in BAL fluids; chemokine gene expression; cytokine gene expression; the presence of lung inflammation, as assessed by BAL cell differential; (% neutrophils and % eosinophils); forced vital capacity (FVC) and diffusing capacity for carbon monoxide (DLco) dyspnea score; skin score; patient and physician global assessments; modified Health Assessment Questionnaire (HAQ); Quality of Life questionnaire; scleroderma disease severity score; organ-specific scores; and Raynaud's activity score.

Eligible subjects will receive a 12 week-course of therapy which will consist of an 7.5 mg IV bolus of alefacept once a week for 12 weeks. Each subject will then be followed 12 weeks after receiving the last dose of alefacept.

All subjects will be followed in monthly Post Study Visits until their lymphocyte counts return to within 75% of their baseline value (Visit 1).

Candidates will be eligible for entry into this study if all of the following inclusion criteria are met within 28 days prior to study drug administration (Visit 1): Must be at least 18 years of age; Must have diagnosis of diffuse or limited cutaneous systemic sclerosis; Must have high clinical suspicion of lung inflammation, restrictive lung disease on PFTs (for example, new or worsening dypsnea, worsening PFTs, anti-topoisomerase I antibody positive, or African American); Must have lung inflammation on screening BAL cell differential, with 2-3% neutrophils or 2-2.2% eosinophils; If on Prednisone for indications other than lung disease, must be on a stable dose which will remain unchanged during the course of the study. This dose should not exceed 10 mg/day; CD4+ lymphocyte counts must be above the lower limit of normal of Covance Central Laboratory value; Must give written informed consent.

Candidates will be excluded from study entry if they have received cyclophosphamide or other potential disease modifying therapy within the past six weeks prior to BAL or if any of the following criteria exist within 28 days prior to enrollment: history of patient non-compliance; continuing alcoholism or drug abuse; other known cause of restrictive lung disease; cigarette smoking within the last 6 months; abnormal hematology values for: hematocrit, hemoglobin, white blood cell count, or platelets that are felt by the investigator to negate their participation in the study; abnormal blood chemistry values that are felt by the investigator to negate their participation in the study; abnormal urinalysis that is felt by the investigator to negate their participation in the study; serious local infection (e.g., cellulitis, abscess)or systemic infection (e.g., pneumonia, septicemia)within the 3 months prior to the first dose of study drug; positive for hepatitis C antibody with an ALT or AST greater than three times upper limit of normal or positive for hepatitis B surface antigen (HBsAg)with an ALT or AST greater than three times upper limit of normal; positive for HIV antibody.

(It is recognized that HIV testing may not be permitted at all sites); history of malignancy other than basal cell carcinomas or fewer than 3 squamous cell carcinomas; treatment with another investigational drug or approved therapy for investigational use within 4 weeks prior to study drug administration.

Female subjects who are not postmenopausal for at least 1 year, surgically sterile, or willing to practice effective contraception during the study, nursing mothers, pregnant women and women planning to become pregnant while on study or with previous participation in any alefacept study are to be excluded.

The drug, alefacept, must be stored in a secure location. Alefacept is supplied as a lyophilized powder which upon reconstitution with 0.65 mL Sterile Water for Injection produces a concentration of 30 mg/mL. Excipient materials (citrate, glycine and sucrose) are also present in the composition. Alefacept dosage units are to be stored at 2-8° C. (36-46° F.).

In order for a subject to receive a dose of study drug, the following must occur: administration of each dose of study drug must be separated by an interval of 7 days (+−2 days); no clinical evidence of significant viral, bacterial, or fungal infection.

Dosing will be according to the schedule provided unless there is evidence of clinically significant infection (as determined by the investigator) or reduction in absolute CD4+ lymphocyte counts as described below. Dosing must be withheld for 2 weeks in the case of fever (body temperature >38° C.) or evidence of clinically significant infection (including upper respiratory infection). If the CD4+lymphocyte count from the previous week is below 250 cells/mm$^3$ as measured by Covance Central Laboratory Services, the subject will have their scheduled dose withheld. If any subject experiences a reduction in number of CD4+lymphocytes below 250 cells/mm$^3$ as measured by Covance Central Laboratory Services for 4 or more consecutive visits, study drug will be permanently withheld and the subject should remain in the study and continue the protocol-specified follow-up evaluations.

All subjects should be followed until their CD4$^+$ lymphocyte counts return to within normal limits as defined by the central laboratory being used for this study.

Subjects who prematurely discontinue study drug should remain in the study and continue the protocol-specified follow-up evaluations. Unless otherwise indicated, a subject must permanently discontinue study drug treatment for any of the following reasons: the subject becomes pregnant; the subject desires to discontinue study drug treatment under this protocol; the subject experiences a medical emergency that necessitates permanent discontinuation of study drug treatment. A subject may have study drug treatment permanently discontinued: at the discretion of the investigator for medical reasons such as flare in disease activity that is felt to require permanent discontinuation of therapy or for noncompliance.

Every effort should be made to continue follow-up on subjects who discontinue study drug prematurely. These evaluations should continue as scheduled under the protocol. The reasons for discontinuation of the study drug must be recorded in the subject's study record. If a subject discontinues study drug, it is recommended that other systemic medications (e.g., methotrexate, cyclophsophamide, etc.) should not be initiated until 4 weeks after the last dose of study drug, or until the CD4 count returns to normal, whichever is the later.

Subjects must be withdrawn from the study if the subject desires to discontinue participation in this study; or is unwilling or unable to comply with the protocol. Subjects who prematurely withdraw from the study may not be replaced. The reasons for withdrawal must be recorded in the subject's study record. If a subject prematurely withdraws from the study between Visits 2 and 14, the tests and evaluations required at Visit 15 should be performed, as described in Section 8, regardless of the reason for study withdrawal.

Compliance with study drug dosing will be monitored and recorded by study personnel.

For subjects on any prescription medication, every attempt should be made to keep the subject on stable doses of that medication for at least 14 days prior to the first dose of study drug. Any medication and any non-drug procedure or therapy utilized from screening until Visit 15 must be recorded in the subject's CRF. All other concomitant medications are allowed, except as outlined in disallowed concomitant therapy. The usual standard of care for all other organ involvement in scleroderma will be provided. Prednisone is allowed at a stable dose not to exceed 10 mg/day. At any time during study participation, subjects may not receive treatment with: live vaccines or live attenuated vaccines (subjects may receive flu vaccines); methotrexate, cyclosporine, azathioprine, or other systemic immunosuppressant and immunomodulatory agents, another investigational drug or approved therapy for investigational use.

For Visits 1 through 12, the tests and evaluations must be performed prior to study drug administration. Subjects will have the tests and evaluations scheduled for each visit irrespective of receiving study drug. All blood samples for hematology and lymphocyte subset analysis should be collected at the same time of the day in order to prevent artifact of diurnal variation.

Following informed consent a screening visit will be conducted. The tests and evaluations described below must be performed within 28 days prior to administration of the first dose of study drug in order to determine subject eligibility and/or baseline values: a complete medical history; a complete physical examination including measurement of vital signs and body weight; urinalysis; blood chemistries; hematology; analysis of peripheral lymphocyte subsets; pregnancy (blood)test for women; tests for hepatitis C antibody and hepatitis B surface antigen (HBsAg); HIV antibody will be determined at sites where permitted; bronchoscopy to obtain BAL fluid and cells; modified Rodnan skin score; patient Global Assessment; physician Global Assessment; UCSD Dyspnea score; pulmonary Function Tests (PFTs) including spirometry, lung volumes and diffusion capacity for carbon monoxide; modified HAQ; Quality of Life questionnaire; scleroderma disease severity score; organ-specific scores; Raynaud's activity score.

Visit 1 (Day 1) will include a complete physical examination including measurement of vital signs and body weight; urinalysis; blood chemistries; hematology (to be obtained prior to study drug administration; analysis of peripheral lymphocyte subsets (to be obtained prior to study drug administration; modified Rodnan skin score*; patient Global Assessment*; physician Global Assessment*; UCSD Dyspnea score*; collection of blood for determination of antibodies to alefacept (to be obtained prior to study drug administration); collection of blood for alefacept pharmacokinetic assay (to be obtained prior to study drug administration); assessment of any new or ongoing viral, bacterial, or fungal infections. modified HAQ*; Quality of Life questionnaire*; scleroderma disease severity score*; organ-specific scores*; Raynaud's activity score*; and administration of alefacept. An asterick "*" indicates that if evaluations at Visit 1 are within 14 days of screening visit it is not necessary to repeat.

Visits 2 (day 8+/−2 days), 3 (day 15+/−2 days), 4, (day 20+/−2 days), 5 (day 29+/−2 days), 6 (day 36+/−2 days),8 (day 50+/−2 days), 9 day (day 57+/−2 days), 10 (day 71+/−2 days), 11 (day 71+/−2 days), 12 (day 78+/−2 days), will include: hematology (to be obtained prior to study drug administration); analysis of peripheral lymphocyte subsets (to be obtained prior to study drug administration); assessment of any new or ongoing viral, bacterial, or fungal infections; and administration of alefacept.

Visit 7 (Day 43+/−2 days) will include: a complete physical examination; hematology (to be obtained prior to study drug administration); analysis of peripheral lymphocyte subsets (to be obtained prior to study drug administration); pregnancy (blood) test for women (to be obtained prior to study drug administration); collection of blood for alefacept pharmacokinetic assay (to be obtained prior to study drug administration); assessment of any new or ongoing viral, bacterial, or fungal infections; and administration of alefacept.

Visit 13 (Day 92, 2 weeks post-final dose, +/−2 days) will include: a complete physical examination including measurement of vital signs; urinalysis; blood chemistries; hematology; analysis of peripheral lymphocyte subsets; bronchoscopy to obtain BAL fluid and cells (+/−7 days); modified Rodnan skin score; patient Global Assessment; physician Global Assessment; UCSD Dyspnea score; pulmonary Function Tests including spirometry, lung volumes and diffusion capacity for carbon monoxide; collection of blood for determination of antibodies to alefacept; collection of blood for alefacept pharmacokinetic assay; assessment of any new or ongoing viral, bacterial, or fungal infections; modified HAQ; Quality of Life questionnaire; scleroderma disease severity score; organ-specific scores; and Raynaud's activity score.

Visit 14 (Day 134, six weeks post-final dose, +/−7 days) will include: hematology, analysis of peripheral lymphocyte subsets; collection of blood for alefacept pharmacokinetic assay; and assessment of any new or ongoing viral, bacterial, or fungal infections.

Visit 15 (Day 176, 14 weeks post-final dose, +/−7 days) will include: a complete physical examination; hematology; analysis of peripheral lymphocyte subsets; bronchoscopy to obtain BAL fluid; modified Rodnan skin score; patient Global Assessment; physician Global Assessment; UCSD Dyspnea score; pulmonary Function Tests (PFrs) including spirometry, lung volumes and diffusion capacity for carbon monoxide; skin score; collection of blood for determination of antibodies to alefacept; collection of blood for alefacept pharmacokinetic assay; assessment of any new or ongoing viral, bacterial, or fungal infections; modified HAQ; Quality of Life questionnaire; scleroderma disease severity score; organ-specific scores; and Raynaud's activity score.

For subjects on any prescription medication, every attempt should be made to keep the subject on stable doses of that medication for at least 14 days prior to the first dose of study drug. If a subject discontinues study drug, it is recommended that other systemic medications (e.g., methotrexate, cyclosporine, PUVA, etc.) should not be initiated until 4 weeks after the last dose of study drug, or when CD4 count returns to normal, whichever is the later. Subjects must be instructed not to donate blood during the study and for the 3 months following their last dose of alefacept.

All efficacy assessments are to be performed by the same physician for each subject and should include: Pulmonary Function Tests (FVC and DLco); USCD Dyspnea Score; Modified Rodnan Skin Score; Patient Global Assessment; Physician Global Assessment; Modified HAQ; Quality of Life questionnaire; Scleroderma disease severity score; Scleroderma organ-specific scores; Raynaud's activity score.

For a subject with scleroderma that undergoes the treatment protocol, the disease-associated values of the subject are expected to stabilize and/or exhibit a trend toward normal, non-symptomatic values. Such disease-associated values include one or more of the following: the number of memory CD8+ T cells per ml BAL (bronchoalveolar lavage) fluid; the number of activated CD8+ T cells in BAL fluid; the number of memory and activated CD4+ T cells in BAL fluids; chemokine gene expression; cytokine gene expression; the presence of lung inflammation, as assessed by BAL cell differential; (% neutrophils and % eosinophils); forced vital capacity (FVC) and diffusing capacity for carbon monoxide (DLco) dyspnea score; skin score; patient and physician global assessments; modified Health Assessment Questionnaire (HAQ); Quality of Life questionnaire; scleroderma disease severity score; organ-specific scores; and Raynaud's activity score Those skilled in the art will appreciate that the foregoing specific protocol can be modified or adapted routinely, e.g., to demonstrate use of the invention with another fibrotic or sclerotic disorder. For example, the protocol can be adapted to the treatment of hepatic fibrosis, wherein standard tests of liver function, e.g., standard blood tests or liver biopsies, are used as indicators of hepatic fibrosis. Alternatively, the protocol can be adapted to the treatment of renal fibrosis, wherein standard tests of kidney function, e.g., the levels of urea or creatine in the blood or kidney biopsies, are used as indicators of renal fibrosis.

Example II

Treatment of Scleroderma in Human Patients

This example describes an open label pilot trial that confirmed the ability of human LFA-3/IgG1 fusion protein (also referred to herein as "alefacept" (Biogen, Cambridge, Mass.)) to reduce T cells, including $CD8^+$ T cells, in the lungs of scleroderma patients with lung inflammation. The reduction in T cells was associated with a decrease in non-specific lung inflammation, as measured by alveolar macrophages and neutrophils. Without being bound by theory, it is believed that alefacept can serve as a molecular bridge between $CD2^+$ cells (largely T cells, especially activated and $CD8^+$ cells) and $Fc\gamma RIII^+$ cells (mostly NK cells), leading to Ig-dependent cellular cytotoxicity of the $CD2^+$ T cell targets.

Eight scleroderma patients with lung inflammation were treated with 12 weekly intravenous infusions of 7.5 mg alefacept, with bronchoalveolar lavage (BAL) done at time 0, 14 weeks (2 weeks after the end of therapy), and 26 weeks (3 months after the end of therapy). Seven patients have thus far finished the entire follow up period. There were 5 women, 3 men, 6 Caucasians, and 2 African Americans, with median age 46 years (range 36-72 years). Seven patients had diffuse disease.

Alefacept was well tolerated, with only one serious adverse event related to protocol, which was hospitalization for transient fever after bronchoscopy, with no infection found. Studies of T cells in the blood and lungs were done. Table 1 shows the change in immune cells and clinical parameters, given as median ($25^{th}$, $75^{th}$ percentile) change from time 0, with negative values indicating decreases from baseline. Patients had depletion of $CD3^+$, $CD4^+$, and $CD8^+$ T cells in both peripheral blood and BAL fluids by week 14, with recovery underway by week 26. There was greater depletion of memory ($CD45RO^+$) than naïve ($CD45RA^+$) T cells in the blood, and reduction in both lungs, with relatively few $CD45RA^+$ T cells in the lungs at baseline. A reduction in alveolar macrophages and BAL neutrophils accompanied the decrease in BAL T cells. During this 26 week period, forced vital capacity (FVC) and diffusing capacity for carbon monoxide (Dlco) were stable, with little over all change in patient and physician global assessment scores (0-10 scale).

This example shows the feasibility of depleting T cells from scleroderma patients, including from both the blood and lungs. The data suggest that, at least in part, T cells may drive the non-specific inflammatory response in the lungs of these patients.

TABLE 1

Change in Immune Cells and Clinical Parameters

| Parameter | Blood (14 weeks) | Blood (26 weeks) | BAL (14 weeks) | BAL (26 weeks) |
|---|---|---|---|---|
| CD3+ T cells/ml | −29% (−42, −21) | 1% (−4, 4) | −36% (−60, −4) | −7% (−41, 80) |
| CD4+ T cells/ml | −24% (−40, −14) | 2% (−6, 7) | −41% (−61, −6) | −37% (−45, 100) |
| CD8+ T cells/ml | −40% (−50, −33) | −10% (−25, −1) | −24% (−59, −4) | 11% (−45, 83) |
| CD4CD45RO+ T cells/ml | −46% (−49, −37) | −16% (−25, −3) | | |
| CD4CD45RA+ T cells/ml | 10% (2, 15) | 43% (25, 89) | | |
| CD8CDRO+ T cells/ml | −51% (−64, −31) | −27% (−48, −10) | | |
| CD8CDRA+ T cells/ml | −7% (−10, −2) | 25% (7, 43) | | |
| Monos/macs/ml | −13% (−36, 9) | −5% (25, 89) | −42% (−47, 2) | −19% (−25, 17) |
| Neutrophils/ml | −6% (−14, 0) | −10% (25, 89) | −40% (−59, −7) | 32% (−41, 119) |
| FVC, % | | | −2% (−8, 0) | 1% (−11, 6) |
| DLco, % | | | −5% (−11, 0) | −6% (−10, 3) |
| Physician Global | | | −7% (−38, −3) | −7% (−44, −6) |
| Patient Global | | | −4% (−17, 0) | −4% (−16, 0) |

Deposits

Murine hybridoma cells and anti-LFA-3 antibodies useful in the present invention are exemplified by cultures deposited under the Budapest Treaty with American Type Culture Collection, Rockville, Md., U.S.A., on Mar. 5, 1991, and identified as:

| Designation | ATCC Accession No. |
|---|---|
| 1E6 | HB 10693 |
| HC-1B11 | HB 10694 |
| 7A6 | HB 10695 |
| 8B8 | HB 10696 |

A bacteriophage carrying a plasmid encoding transmembrane LFA-3 was deposited under the Budapest Treaty with In Vitro International, Inc., Linthicum, Md., U.S.A., on May 28, 1987 under Accession No. IVI-10133. This deposit was transferred to American Type Culture Collection on Jun. 20, 1991 and identified as:

| Designation | ATCC Accession No. |
|---|---|
| λHT16[λgt10/LFA-3] | 75107 |

*E. coli* transformed with a plasmid encoding PI-linked LFA-3 was deposited under the Budapest Treaty with In Vitro International, Inc. on Jul. 22, 1988 under Accession No. IVI-10180. This deposit was transferred to American Type Culture Collection on Jun. 20, 1991 and identified as:

| Designation | ATCC Accession No. |
|---|---|
| p24 | 68788 |

Sequences

The following is a summary of the sequences described in U.S. Pat. No. 6,162,432 and referred to throughout the application:

| | |
|---|---|
| SEQ ID NO: 1 | DNA sequence of transmembrane LFA-3 |
| SEQ ID NO: 2 | Amino acid sequence of transmembrane LFA-3 |
| SEQ ID NO: 3 | DNA sequence of PI-linked LFA-3 |
| SEQ ID NO: 4 | Amino acid sequence of PI-linked LFA-3 |
| SEQ ID NO: 5 | DNA sequence of CD2 |
| SEQ ID NO: 6 | Amino acid sequence of CD2 |
| SEQ ID NO: 7 | DNA sequence of LFA-3TIP |
| SEQ ID NO: 8 | Amino acid sequence of LFA-3TIP |

Equivalents

Those skilled in the art will recognize, or be able to ascertain using no more than routine experimentation, many equivalents of the specific embodiments of the invention described herein. Such equivalents are intended to be encompassed by the following claims.

Other embodiments are within the following claims.

What is claimed is:

1. A method of treating a subject having scleroderma comprising administering to the subject a CD2-binding agent comprising a CD2-binding fragment of LFA-3 fused to all or part of an immunoglobulin hinge and further fused to the CH2 and CH3 regions of a human IgG1 heavy chain constant domain, in an amount sufficient to do one or more of:
   (a) attenuate the severity of the disorder,
   (b) suppress the deleterious effects of the disorder, or
   (c) preserve function of a visceral organ in the subject, and optionally further comprising administering an additional agent, wherein the additional agent is not an inhibitor of an ICAM-1/LFA-1 interaction.

2. A method of treating scleroderma in a subject, comprising administering to the subject a CD2-binding agent comprising a CD2-binding fragment of LFA-3 fused to all or part of an immunoglobulin hinge and further fused to the CH2 and CH3 regions of a human IgG1 heavy chain constant domain in an amount effective to treat said disorder, and optionally comprising administering an additional agent, wherein the additional agent is not an inhibitor of an ICAM-1/LFA-1 interaction.

3. The method of claim 2, wherein the disorder is further characterized by aberrant inflammatory and vascular activities.

4. The method of claim 1 or 2, wherein the subject is a mammal.

5. The method of claim 4, wherein the subject is a primate.

6. The method of claim 4, wherein the subject is a human.

7. The method of claim 1 or 2, wherein the scleroderma is systemic or circumscribed scleroderma.

8. The method of claim 7, wherein the scleroderma is characterized by visceral organ involvement.

9. The method of claim 8, wherein the visceral organ involvement affects the gastrointestinal tract, the cardiorespiratory system, the renal system, or the musculoskeletal system.

10. The method of claim 9, wherein the visceral organ involvement affects the lungs, the heart, or kidneys.

11. The method of claim 10, wherein the visceral organ involvement comprises fibrotic impairment of the lungs.

12. The method of claim 10, wherein the visceral organ involvement comprises fibrotic impairment of the heart.

13. The method of claim 10, wherein the visceral organ involvement comprises fibrotic impairment of the kidneys.

14. The method of claim 7, wherein the scleroderma is characterized by fibrosis of the skin.

15. The method of claim 1 or 2, wherein the disorder is characterized by aberrant interstitial fibrosis.

16. The method of claim 1 or 2, wherein the disorder is an interstitial lung disease.

17. The method of claim 16, wherein the disorder is selected from the group consisting of fibrosing alveolitis associated with systemic sclerosis (FASSc) and pulmonary hypertension caused by vascular disease of the lung.

18. The method of claim 1 or 2, wherein the disorder is circumscribed scleroderma.

19. The method of claim 1 or 2, wherein the disorder is cutaneous scleroderma or CREST syndrome (Calcinosis, Raynaud's phenomenon, Esophageal dysfunction, Sclerodactyly, Telagiectasia).

20. The method of claim 1 or 2, wherein the subject has a modified Rodnan skin score of at least about 10.

21. The method of claim 20, wherein the subject has a modified Rodnan skin score of at least about 20.

22. The method of claim 1 or 2, wherein the subject has a mean alveolar wall thickness of less than about 20 microns.

23. The method of claim 1 or 2, wherein the subject has a mean alveolar wall thickness between about 20 to 40 microns.

24. The method of claim 1 or 2, wherein the subject has a mean alveolar wall thickness greater than about 40 microns.

25. The method of claim 1 or 2, wherein the subject has a bronchoalveolar lavage (BAL) cell differential of greater than or equal to 3% neutrophils or greater than or equal to 2.2% eosinophils.

26. The method of claim 1 or 2, wherein the subject has an elevated number of memory CD8+ cells in the BAL fluids from said subject.

27. The method of claim 1 or 2, wherein the CD2-binding agent is administered systemically or parenterally.

28. The method of claim 27, wherein the CD2-binding agent is administered intravenously, intramuscularly, subcutaneously, transdermally, or by inhalation.

29. The method of claim 1 or 2, wherein the CD2-binding agent is administered locally to an area affected by said disorder.

30. The method of claim 1 or 2, wherein the CD2-binding agent further comprises a moiety which binds to an effector cell.

31. The method of claim 1 or 2, wherein the CD2-binding agent is a soluble LFA-3 polypeptide comprising an amino acid sequence that is selected from the group consisting of: (a) amino acid 1 to amino acid 92 of SEQ ID NO: 2; (b) amino acid 1 to amino acid 80 of SEQ ID NO: 2; (c) amino acid 50 to amino acid 65 of SEQ ID NO: 2; and (d) amino acid 20 to amino acid 80 of SEQ ID NO: 2.

32. The method of claim 31, wherein the soluble LFA-3 polypeptide is a fusion protein comprising the amino terminal 92 amino acids of mature LFA-3 and the C-terminal 10 amino acids of a human IgG1 hinge region.

33. The method of claim 1 or 2, wherein the CD2-binding agent is administered in an amount effective to inhibit fibrosis.

34. The method of claim 31, wherein the CD2-binding agent is administered at a dosage ranging from about 0.001 to about 50 mg binding agent per kg body weight.

35. The method of claim 31, wherein the CD2-binding agent is administered systemically.

36. The method of claim 35, wherein the CD2-binding agent is administered to a subject once a week during a therapeutic treatment period of twelve weeks.

37. The method of claim 36, wherein the CD2-binding agent is administered at a dosage ranging from about 0.001 to about 50 mg binding agent per kg body weight.

38. The method of claim 35, wherein the CD2-binding agent is administered at a dosage ranging from 5 to 10 mg IV bolus at least once during said therapeutic treatment period.

39. The method of claim 35, wherein the CD2-binding agent is administered at a dosage of 7.5 mg IV bolus at least once during said therapeutic treatment period.

40. The method of claim 1 or 2, further comprising administering an CD2-binding agent in combination with one or more of: a cytokine inhibitor, a vasodilator, an immunosuppressant, cyclophosphamide, a corticosteroid or penicillamine.

41. The method of claim 40, wherein the cytokine inhibitor is an anti-IL2 antibody.

42. The method of claim 1 or 2, further comprising administering an CD2-binding agent in combination with one or more inhibitors of interleukin-1 (IL-1), IL-2, IL-4, IL-6, IL-8, TNF-α, TGF-α, PDGF, granzyme A or leukotriene B4.

43. The method of claim 40, further comprising administering a CD2-binding agent in combination with a vasodilator.

44. The method of claim 43, wherein the vasodilator is an ACE inhibitor or minoxidil.

45. The method of claim 40, further comprising administering a CD2-binding agent in combination with an immunosuppressant.

46. The method of claim 40, further comprising administering a CD2binding agent in combination with cyclophosphamide.

47. The method of claim 45, wherein the immunosuppressant is methotrexate, cyclosphorin, or chlorambucil.

48. The method of claim 40, further comprising administering a CD2-binding agent in combination with a corticosteroid.

49. The method of claim 40, further comprising administering a CD2-binding agent in combination with penicillamine.

* * * * *

UNITED STATES PATENT AND TRADEMARK OFFICE
CERTIFICATE OF CORRECTION

| | |
|---|---|
| PATENT NO. | : 7,858,095 B2 |
| APPLICATION NO. | : 10/484329 |
| DATED | : December 28, 2010 |
| INVENTOR(S) | : Akshay K. Vaishnaw |

It is certified that error appears in the above-identified patent and that said Letters Patent is hereby corrected as shown below:

In Column 3, at line 3, "intestinal fibrosis" should read --interstitial fibrosis--

In Column 3, at line 3, "intestinal lung disease" should read --interstitial lung disease--

In Column 5, at line 59, "TNF-.alpha, TGF-.beta" should read --TNF-α, TGF-β--

In Column 27, at line 20, "cell" should read --cells--

In Column 30, at line 48, "Immunoglebulin" should read --Immunoglobulin--

In Column 31, at line 9, "Czamik" should read --Czarnik--

In Column 31, at line 10, "Arnstrong" should read --Armstrong--

In Column 31, at line 39, "linrary" should read --library--

In Column 31, at line 43, "appriciated" should read --appreciated--

In Column 33, at line 61, "TNF-.alpha, TGF-.beta" should read --TNF-α, TGF-β--

In Column 39, at line 3, "(+–2 days)" should read --(+/–2 days)--

Signed and Sealed this
Seventh Day of June, 2011

David J. Kappos
*Director of the United States Patent and Trademark Office*